United States Patent
Bley et al.

(10) Patent No.: US 12,390,363 B2
(45) Date of Patent: Aug. 19, 2025

(54) OPHTHALMIC DRUG COMPOSITIONS

(71) Applicant: Oxular Limited, Oxford (GB)

(72) Inventors: Robert Steven Bley, Menlo Park, CA (US); Stanley R. Conston, San Carlos, CA (US); Ronald K. Yamamoto, Oxford (GB); Tien T. Nguyen, Daly City, CA (US); John P. Lunsford, San Carlos, CA (US); Dillon Daniel Martinez, Oakland, CA (US); Loc X. Phan, Santa Clara, CA (US)

(73) Assignee: Oxular Limited, Oxford (GB)

( * ) Notice: Subject to any disclaimer, the term of this patent is extended or adjusted under 35 U.S.C. 154(b) by 224 days.

(21) Appl. No.: 18/073,089

(22) Filed: Dec. 1, 2022

(65) Prior Publication Data

US 2023/0355431 A1 Nov. 9, 2023

Related U.S. Application Data

(63) Continuation of application No. 16/646,688, filed as application No. PCT/GB2018/052641 on Sep. 14, 2018, now Pat. No. 11,564,834.
(Continued)

(51) Int. Cl.
*A61K 9/00* (2006.01)
*A61F 9/00* (2006.01)
(Continued)

(52) U.S. Cl.
CPC .......... *A61F 9/0017* (2013.01); *A61K 9/0024* (2013.01); *A61K 9/0048* (2013.01);
(Continued)

(58) Field of Classification Search
CPC ....... A61K 9/10; A61K 9/0017; A61K 9/0024
See application file for complete search history.

(56) References Cited

U.S. PATENT DOCUMENTS

| 5,384,124 A | 1/1995 | Courteille |
| 5,665,071 A | 9/1997 | Wyrick |

(Continued)

FOREIGN PATENT DOCUMENTS

| CN | 101554364 | 10/2009 |
| CN | 106492284 | 3/2017 |

(Continued)

OTHER PUBLICATIONS

Panyam et al., "Solid-State Solubility Influences Encapsulation and Release of Hydrophobic Drugs from PLGA/PLA Nanoparticles", Journal of Pharmaceutical Sciences, 2004, 93(7), pp. 1804-1814.
(Continued)

*Primary Examiner* — Carlos A Azpuru
(74) *Attorney, Agent, or Firm* — Bookoff McAndrews, PLLC

(57) ABSTRACT

The present invention provides a drug composition comprising particles comprising a biodegradable or bioerodable polymer and a drug, a soluble, biodegradable or bioerodible excipient, a bulking agent and a reconstitution aid. The invention also provides a pharmaceutical formulation and a unit dosage form of the pharmaceutical formulation. The invention provides methods of treatment of a disease or condition accordingly. The invention also provides a drug composition for use in a cannulation device.

26 Claims, 11 Drawing Sheets

Related U.S. Application Data

(60) Provisional application No. 62/559,218, filed on Sep. 15, 2017.

(51) Int. Cl.

| | | |
|---|---|---|
| *A61K 9/10* | (2006.01) | |
| *A61K 9/16* | (2006.01) | |
| *A61K 31/573* | (2006.01) | |
| *A61K 47/54* | (2017.01) | |
| *A61M 5/31* | (2006.01) | |
| *A61M 5/315* | (2006.01) | |
| *A61M 5/32* | (2006.01) | |
| *A61M 25/00* | (2006.01) | |
| *A61M 5/178* | (2006.01) | |

(52) U.S. Cl.
CPC .............. *A61K 9/0051* (2013.01); *A61K 9/10* (2013.01); *A61K 9/1611* (2013.01); *A61K 9/1635* (2013.01); *A61K 9/1647* (2013.01); *A61K 9/1652* (2013.01); *A61K 31/573* (2013.01); *A61K 47/543* (2017.08); *A61M 5/31* (2013.01); *A61M 5/315* (2013.01); *A61M 5/32* (2013.01); *A61M 25/0068* (2013.01); *A61M 5/178* (2013.01); *A61M 5/31511* (2013.01); *A61M 5/31515* (2013.01); *A61M 2005/3201* (2013.01); *A61M 5/3243* (2013.01); *A61M 5/3273* (2013.01); *A61M 2205/0266* (2013.01); *A61M 2205/587* (2013.01); *A61M 2210/0612* (2013.01)

(56) References Cited

U.S. PATENT DOCUMENTS

| | | | |
|---|---|---|---|
| 6,331,313 | B1 | 12/2001 | Wong et al. |
| 6,489,252 | B2 | 12/2002 | Goo et al. |
| 2003/0077297 | A1 | 4/2003 | Chen et al. |
| 2004/0092435 | A1 | 5/2004 | Peyman |
| 2005/0048099 | A1 | 3/2005 | Shiah et al. |
| 2006/0013859 | A1 | 1/2006 | Yamada et al. |
| 2008/0131484 | A1 | 6/2008 | Robinson et al. |
| 2008/0207756 | A1 | 8/2008 | Herweck et al. |
| 2009/0036827 | A1 | 2/2009 | Cazzini |
| 2009/0148527 | A1 | 6/2009 | Robinson et al. |
| 2009/0196905 | A1 | 8/2009 | Spada et al. |
| 2010/0098772 | A1 | 4/2010 | Robinson et al. |
| 2010/0104654 | A1 | 4/2010 | Robinson et al. |
| 2010/0151033 | A1 | 6/2010 | Ahlheim et al. |
| 2011/0238075 | A1 | 9/2011 | Clauson et al. |
| 2013/0096534 | A1 | 4/2013 | Orilla et al. |
| 2013/0216623 | A1 | 8/2013 | Yamamoto et al. |
| 2013/0289467 | A1 | 10/2013 | Haffner et al. |
| 2014/0294986 | A1 | 10/2014 | Liu et al. |
| 2015/0051581 | A1 | 2/2015 | Andino et al. |
| 2017/0056504 | A1 | 3/2017 | Kohn et al. |
| 2017/0224534 | A1 | 8/2017 | Andino et al. |

FOREIGN PATENT DOCUMENTS

| | | |
|---|---|---|
| EP | 2007353 | 12/2008 |
| EP | 2485711 | 8/2012 |
| EP | 2248494 | 6/2013 |
| EP | 2981248 | 2/2016 |
| JP | 2003095955 | 4/2003 |
| JP | 2006257080 | 9/2006 |
| JP | 2008-509727 A | 4/2008 |
| JP | 2009-531298 A | 9/2009 |
| JP | 2012116863 A | 6/2012 |
| JP | 2012-527318 A | 11/2012 |
| JP | 2013-511527 A | 4/2013 |
| JP | 2013-543418 A | 12/2013 |
| WO | 2005107845 | 11/2005 |
| WO | 2008041246 | 4/2008 |
| WO | 2009089409 | 7/2009 |
| WO | 2010/126833 | * 11/2010 |
| WO | 2016042162 | 3/2016 |
| WO | 2016042163 | 3/2016 |
| WO | 2017158365 | 9/2017 |

OTHER PUBLICATIONS

Herrero-Vanrell et al., "The potential of using biodegradable microspheres in retinal diseases and other intraocular pathologies", Progress in Retinal and Eye Research, 2014, 42, pp. 27-43.
Kompella et al., "Nanomedicines for back of the eye drug delivery, gene delivery, and imaging", Progress in Retinal and Eye Research, 2013, 36, pp. 172-198.
Bhardwaj et al., "PLGA/PVA hydrogel composites for long-term inflammation control following s.c. implantation", International Journal of Pharmaceutics, 2010, 384(1-2), pp. 78-86.
Definition of "binder", Accessed online on Aug. 7, 2020 at www.merriam-webster.com, 2020.
Li et al. "High-Yield Fabrication of PLGA Non-Spherical Microarchitectures by Emulsion-Solvent Evaporation Method", Macromol Rapid Commun, 2010, 31, pp. 1981-1986.
Hoeh et al., "Early postoperative safety and surgical outcomes after implantation of a suprachoroidal micro-stent for the treatment of open-angle glaucoma concomitant with cataract surgery", J Cataract Refract Surg, 2013, 39, pp. 431-437.
Lazzeri et al., "Biodegradable hollow microfibres to produce bioactive scaffolds", Polym Int, 2005, 54, pp. 101-107.
Mack et al., "A biodegradable filament for controlled drug delivery", Journal of Controlled Release, 2009, 139, pp. 205-211.
Yacasi et al., "Freeze drying optimization of polymeric nanoparticles for ocular flurbiprofen delivery: effect of protectant agents and critical process parameters on long-term stability", 2017, Drug Development and Industrial Pharmacy, 43(4), pp. 637-651.
Almalik et al., "Effect of cryoprotection of particle size stability and preservation of chitosan nanoparticles with and without hyaluronate or alginate coating", 2017, Saudi Pharmaceutical Journal, 25, pp. 861-867.
Abdelwahed et al., "A polit study of freeze drying of poly(epsilon-caprolactone) nanocapsules stabilized by poly (vinyl alcohol): Formulation and process optimization", 2006, International Journal of Pharmaceutics, 309, pp. 178-188.
Non-Final Office Action dated Nov. 27, 2019 in related U.S. Appl. No. 15/512,147.
Final Office Action dated Aug. 10, 2020 in related U.S. Appl. No. 15/512,147.
Non-Final Office Action dated Dec. 15, 2023 in related U.S. Appl. No. 17/534,905.
Cordero-Coma et al., "Golimumab for Uveitis", Ophthalmology, 2011, 118(9), pp. 1892.e3-1892.e4.
Final Office Action dated Jul. 17, 2023 in related U.S. Appl. No. 17/534,905.
Park et al., "Predictors of Glass Transition in the Biodegradable Poly-lactide and Poly-lactide-co-glycolide Polymers", Journal of Applied Polymer Science, 2006, 100, pp. 1983-1987.
Advisory Action dated Nov. 15, 2024 in related U.S. Appl. No. 17/534,905.
Non-Final Office Action dated Dec. 19, 2024 in related U.S. Appl. No. 17/534,905.

* cited by examiner

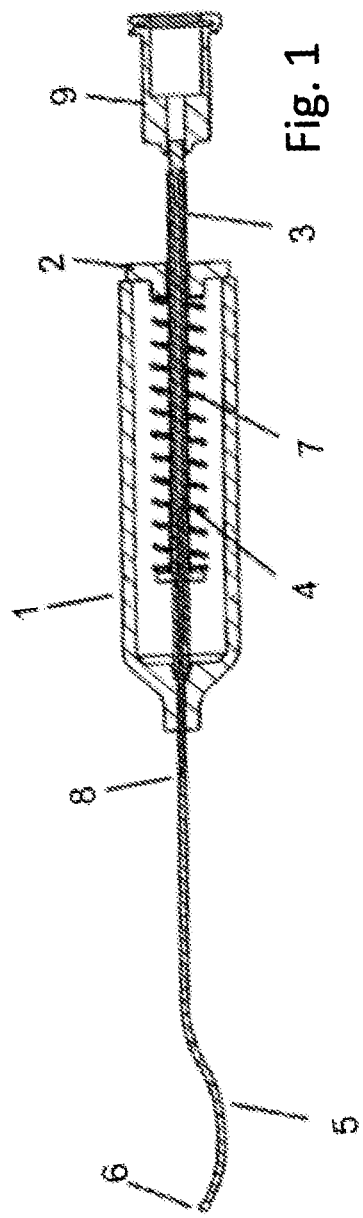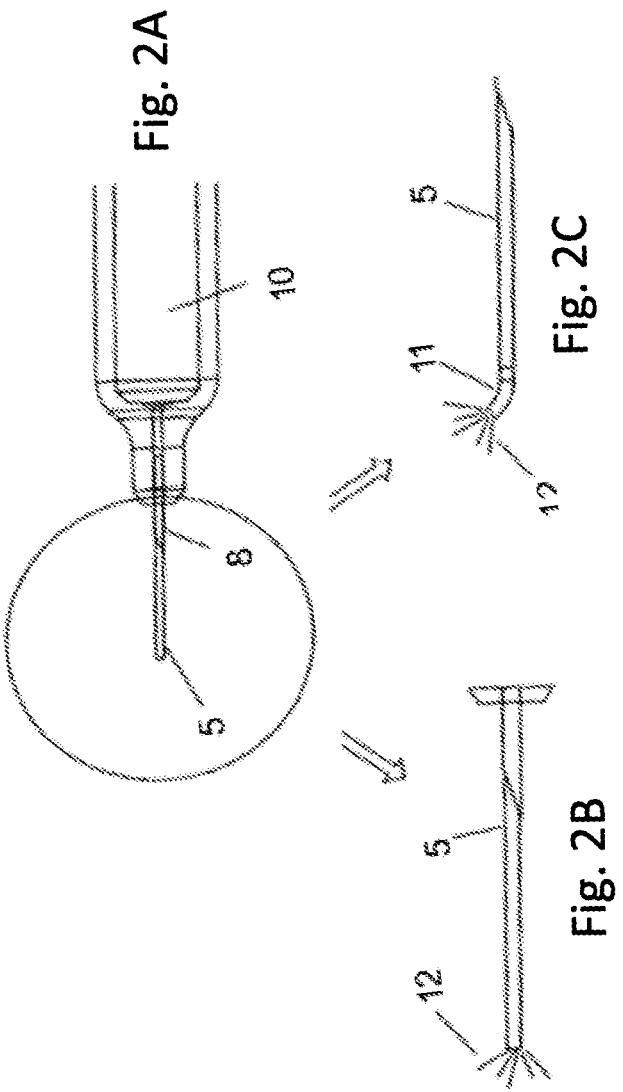

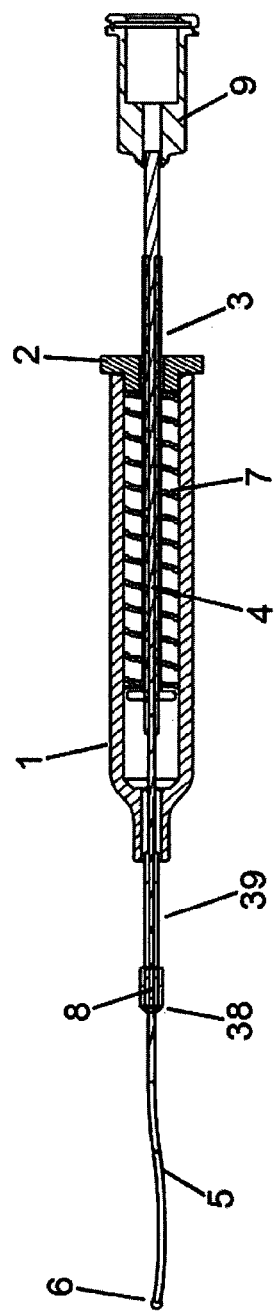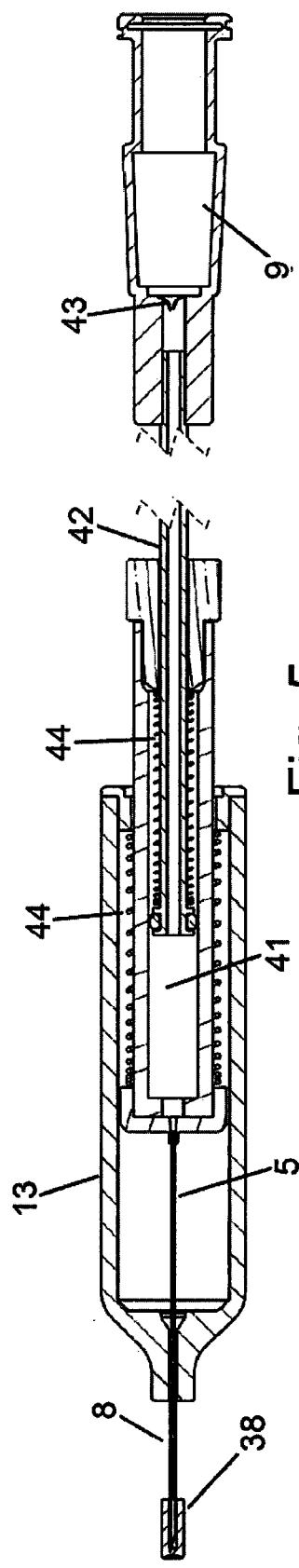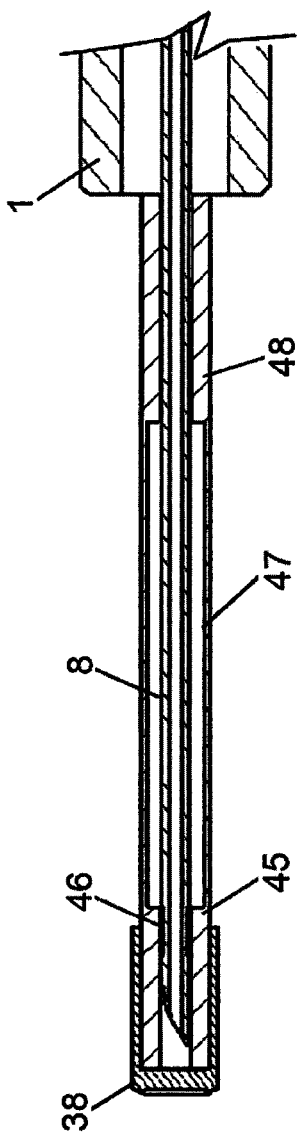
Fig. 4
Fig. 5
Fig. 6

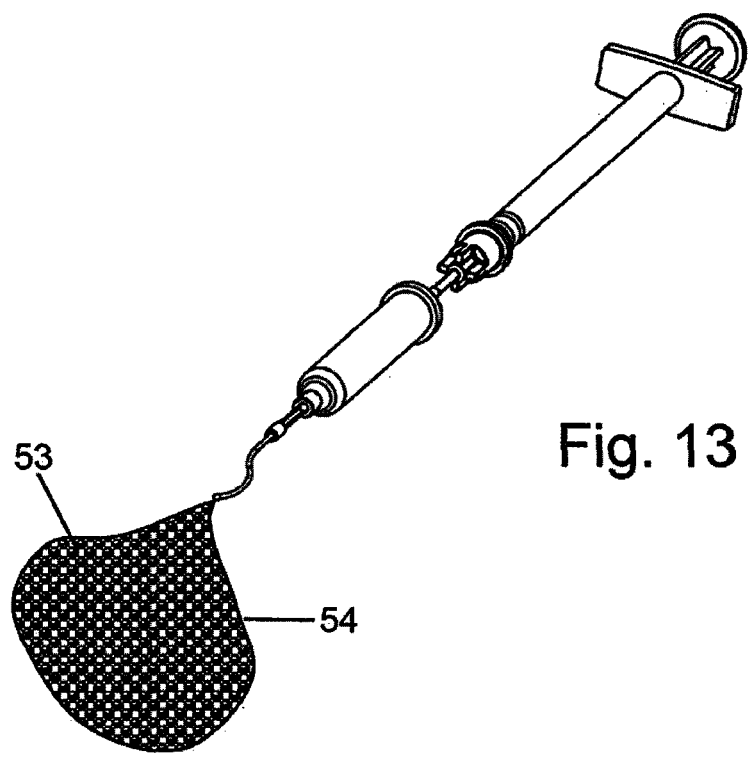
Fig. 13
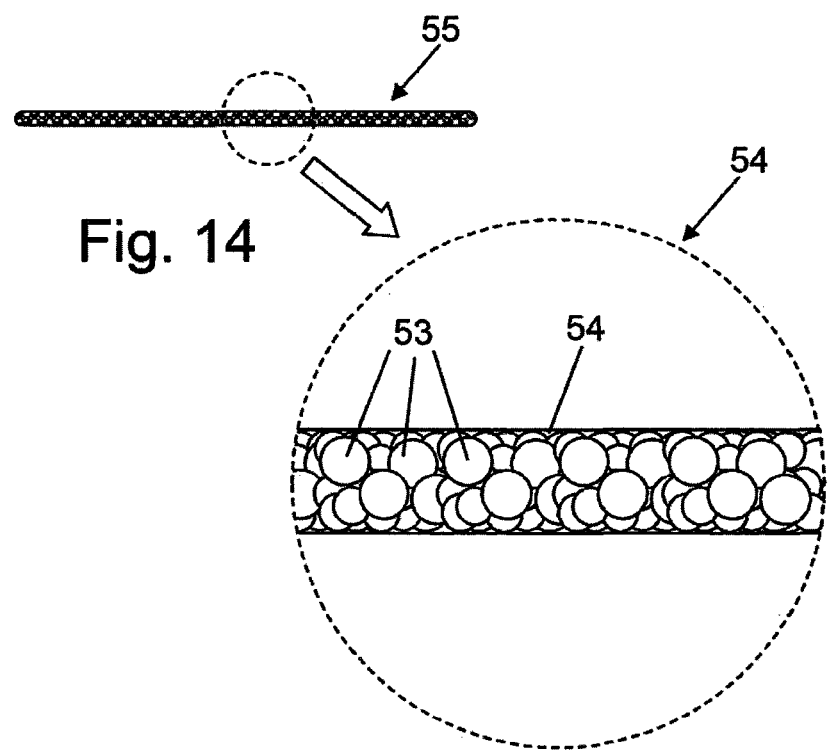
Fig. 14
Fig. 14A

OPHTHALMIC DRUG COMPOSITIONS

CROSS REFERENCE TO OTHER APPLICATIONS

The following patent applications are incorporated by reference: PCT/EP2015/071520, PCT/EP2015/071522, PCT/GB2017/050731.

BACKGROUND OF INVENTION

Due to the unique anatomy and physiology of the eye, multiple barriers exist that prevent significant transport of drugs or therapeutic active agents to ocular tissues. The blood vessels of the eye have restricted permeability due to the blood-ocular barriers that regulate intraocular fluid. Due to these blood-ocular barriers, systemically administered drugs do not reach significant concentration in ocular tissues. Drugs in topical drops administered to the corneal surface are mostly washed out by tears into the nasolacrimal duct. While in the tear film, drugs have limited time to penetrate the cornea to reach the intraocular space. Some drugs may be delivered to the front, anterior portion of the eye by drops, but reaching significant therapeutic concentrations in the posterior portion of the eye and the retina is generally not achieved with topical methods of administration.

Many diseases that result in visual loss involve the posterior retina where color vision and reading occur. To treat the posterior portion of the eye and the posterior retina typically drugs are injected into the eye. Sub-conjunctival injections are used to place a drug depot under the outer layer of the eye, however the very high lymphatic flow in the conjunctiva leads to rapid transport of the drug away from the eye. Sub-conjunctival injections are typically not effective to achieving high drug levels in the posterior portion of the eye.

Sub-Tenon's injections are sometimes used to place the drug under the conjunctiva and Tenon's capsule of the eye in a more posterior location to deliver drug to the posterior region of the eye. Sub-Tenon's injections have been demonstrated to be useful for the administration of steroids, however many drugs do not achieve significant drug levels in the retinal tissues from sub-Tenon's injection. The tip of the injection needle is placed deep into the posterior shell of the eye where the tip of the needle cannot be directly observed. The technique requires experience and careful technique to avoid physical injury to the eye or misplacement of drug.

Intravitreal injections are given to place drug directly into the vitreous chamber, and typically require a smaller quantity of drug as compared to sub-Tenon's injections. The half-life of the drug is limited due to the fluid in the vitreous which continuously moves forward toward the anterior chamber. This vitreous flow washes out the drug over time and contacts the drug to other tissues of the eye in the flow path. Intravitreally administered drugs such as steroids are associated with complications of cataract progression due to drug exposure to the lens and increased intraocular pressure from drug exposure to the trabecular meshwork during anterior flow from the vitreous chamber.

The suprachoroidal space between the choroid and sclera and the supraciliary space between the ciliary body and sclera are more difficult to locate but also can be used for the injection of drugs. Unlike intravitreal injections, the fluid in the suprachoroidal space and supraciliary space flows posteriorly. This flow may assist drugs injected into the suprachoroidal space or the supraciliary space to reach the posterior tissues and posterior retina. Small drug particle sizes are ideal for migration in the suprachoroidal space or supraciliary space, however small drug particles release drug at a much faster rate thereby reducing the longevity of the drug treatment.

One potential problem with all injections of drug into the eye beneath the sclera is increased intraocular pressure (IOP) caused by the additional volume introduced into the eye. The increased IOP may cause pain and potential damage to the optic nerve. For highly active drugs a small injection volume may be used without significant acute IOP increase, for example 0.05 ml of anti-VEGF drugs. However, for larger volumes such as 0.1 ml with steroids, IOP increase may be significant and may cause an acute period of pain and loss of vision.

SUMMARY OF THE INVENTION

In keeping with the foregoing discussion, the present invention provides a solid or semi-solid drug composition comprising a biodegradable polymer and a drug such that the composition is designed for administration through a small gauge needle or cannula, for example, in to the suprachoroidal space or supraciliary space of an eye. In the present application the terms "active agent", "drug", "therapeutic agent" and "therapeutic material" are used interchangeably. In the context of the present application, a semi-solid composition refers to a material that does not flow without pressure and remains localized to a location in the eye immediately after delivery.

As described herein, a semi-solid material for injection is provided comprising drug particles in a semi-solid excipient or mixture of excipients. In particular, the semi-solid composition comprises a drug; the semi-solid composition flows under injection pressure; the semi-solid composition remains localized at the site of administration during and immediately after administration; and the semi-solid composition undergoes dissolution after administration to migrate in the suprachoroidal space.

In one embodiment, the drug particles are drug containing microspheres fabricated from one or more biodegradable or bioerodable polymers. To minimize the frequency of administration to a patient, in some embodiments, the drug containing microspheres are configured to provide slow release of the drug. As described herein, the drug in the microspheres is primarily in the form of an amorphous solid dispersion. As described herein, the microspheres are suspended in a viscoelastic excipient to aid flow properties in delivery through a small gauge needle or cannula. As described herein, the semi-solid composition comprising drug containing microspheres is in the form of a lyophilized material that provides rapid reconstitution with aqueous fluid just prior to administration. As described herein, the semi-solid composition comprising drug containing microspheres and a viscoelastic excipient is in the form of a lyophilized material that provides rapid reconstitution with aqueous fluid just prior to administration.

While the semi-solid formulations containing an active agent are ideal for the cannulation device of the present invention, for delivery to the suprachoroidal or supraciliary spaces, the formulations are also useful for all other forms of ophthalmic injections including intravitreal injections, sub-conjunctival injections, sub-Tenon injections and intracameral injections. The sizing of the particles and concentration in a semi-solid or viscous excipient enables injection of a small volume through a small gauge needle or cannula.

The properties of the solid and semi-solid drug compositions are also useful for administration to other localized regions of the body to treat conditions such as sinusitis, osteoarthritis, rheumatoid arthritis, joint inflammation, rhinitis or post-operative inflammation.

The present invention also provides a device designed for the minimally invasive insertion or placement of a flexible cannula or catheter into the suprachoroidal space or supraciliary space of an eye for the purpose of administering a drug containing composition. The cannula or catheter comprises an elongated tubular element which is placed into the suprachoroidal space or supraciliary space by passage through the lumen of a needle or trocar. A surgical instrument with a sharpened distal tip to insert a cannula or catheter is often described as a trocar, which is used interchangeably with the term "needle" in the present application. The term "cannula" is used interchangeably with the term "catheter" in the present application. The disclosure is a cannulation device which incorporates a needle or trocar, a flexible cannula or catheter and a mechanism to facilitate insertion of the cannula into the suprachoroidal space or supraciliary space.

While drug containing materials may be injected into the suprachoroidal space or supraciliary space with a needle, the length of the needle bevel distal to the luminal opening of the needle is of significant length relative to the thickness of the tissue overlying the suprachoroidal or supraciliary space, in the range of 1 mm or more even for small gauge hypodermic needles. As a result, the choroid or ciliary body may be pierced by the needle during injection into the suprachoroidal space or supraciliary space. Although the drug containing material may be injected in the suprachoroidal space or supraciliary space, the penetration of the underlying tissue creates a path for the drug to easily leak into the intraocular space such as the vitreous.

For drugs where it is desired to avoid high intraocular levels, injection of drug containing materials with a needle directly into the suprachoroidal space or supraciliary space may lead to poor control of drug distribution. The use of a trocar to introduce a flexible cannula into the suprachoroidal space or supraciliary space, advancement of the cannula away from the site of tissue penetration by the trocar and administration of a drug containing material or composition through the cannula avoids direct leakage of the drug into the intraocular space. In addition, advancement of the cannula allows positioning of the site of drug administration to be near the desired tissues to be treated, such as the posterior retina or an ocular tumour.

The cannulation device comprises an elongated barrel with a hollow needle at the distal end, where the lumen of the needle serves as a reservoir for at least a portion of the flexible cannula, and further includes a mechanism to advance the flexible cannula through the needle and out from the distal end of the needle into a tissue space. The cannula may be advanced manually such as with a sliding mechanism designed for manual control by a finger holding the device. The cannula may also be advanced by a plunger with a force element such as a spring or gas reservoir that provides a force to the cannula to advance or deploy the cannula from the distal end of the needle. The distal end of the cannula is sized with a diameter less than or equal to the inner diameter of the needle lumen. In one embodiment, the deployment force is activated simultaneous with or immediately after advancement of the needle tip into tissue.

As described herein, the cannulation device also incorporates a distal element comprising a tissue interface with a distal seal secured to the distal end of the cannulation device thereby sealing the needle lumen during application of the deployment force. The distal seal is penetrable or deformable by the distal tip of the needle by the application of pressure on the tissue surface with the distal end of the cannulation device and the penetrated distal element becomes slidable on the needle to allow advancement of the needle into tissue. Penetration of the distal seal opens a path for advancement of the cannula from the distal end of the needle. A force element of the cannulation device with a distal element and distal seal is activated prior to or simultaneous with penetration of the distal seal by the needle and advancement of the needle tip into tissues, thereby enabling simple one-handed operation of the cannulation device to administer the cannula to the suprachoroidal space or supraciliary space of an eye.

As described herein, the distal tip of the needle may be curved or incorporate an inner deflecting element in the needle lumen to direct the cannula at an angle from the long axis of the needle during delivery of the flexible cannula. In one embodiment, the distal end of the cannula is curved in an unconstrained state and is directed at an angle from the long axis of the needle once deployed from the distal tip of the needle. In another embodiment, the cannula is directed at an angle from the long axis of the needle during deployment in a posterior direction. In another embodiment, the cannula is directed at an angle from the long axis of the needle during deployment in a direction away from the tissue underlying the tissue space.

As described herein, the distal tip of the cannula comprises a tubular segment that is 1 to 3 mm in length that is more flexible than the proximal portion of the cannula. In one embodiment, the distal end of the cannula has a lubricious coating on the outer surface to minimize trauma and friction when in contact with tissue. In one embodiment, the distal tip of the cannula is rounded or profiled to be atraumatic when contacting tissue.

As described herein, the cannula is illuminated to provide visualization of the location of the distal end when in the suprachoroidal or supraciliary space to identify and allow guidance of the location of the cannula for administration of a drug composition or therapeutic material. The light emitted by the illuminated cannula when in the suprachoroidal or supraciliary space, through the overlying sclera, has visual characteristics that allow verification of the cannula location prior to administration of the drug composition or therapeutic material. The illuminated cannula also provides a headlight effect from the distal end of the needle which is no longer visible on the surface of the eye when the needle bevel enters the sclera, indicating to the user that the cannula is in position for application of a deployment force to the cannula. In one embodiment, the cannula deployment is triggered by the user when the headlight on the surface of the eye is no longer visible after needle insertion.

As described herein, the cannula provides a fluid connection through the cannulation device to enable delivery of a flowable material for administration such as a drug containing composition or therapeutic material through the lumen of the cannula into a tissue space such as the suprachoroidal space or supraciliary space. As described herein, the cannulation device contains a reservoir of a material for administration which may be delivered through the lumen of the cannula into the tissue space such as the suprachoroidal or supraciliary space. As described herein, the cannulation device contains a reservoir of material for administration which may be delivered through the lumen of the cannula into the tissue space such as the suprachoroidal or supraciliary space where the material for administration is a semi-solid composition.

These and other aspects of the invention will be made apparent from consideration of the following detailed description in conjunction with the accompanying drawings and figures.

BRIEF DESCRIPTION OF THE DRAWINGS

FIG. 1 depicts one embodiment of a cannulation device for deploying a flexible cannula into a tissue space of an eye.

FIGS. 2, 2A and 2B 2A, 2B, and 2C depict embodiments of a cannulation device for deploying a flexible cannula with illumination having a straight tip and a curved tip into a tissue space of an eye.

FIG. 4 depicts one embodiment of a cannulation device with a distal element and distal seal for deploying a flexible cannula into a tissue space of an eye.

FIG. 5 depicts one embodiment of a cannulation device with a distal element and distal seal for deploying a flexible cannula into a tissue space of an eye, with a reservoir to contain a material for administration.

FIG. 6 depicts one embodiment of a distal tip of a cannulation device with a collapsible element.

FIG. 13 depicts a delivery device expelling a semi-solid composition for administration.

FIG. 14 depicts a solid or semi-solid composition for administration shaped as an elongated body.

FIG. 14A depicts a magnified detail of the composition of FIG. 14A.

DESCRIPTION OF THE INVENTION

Figure 3:
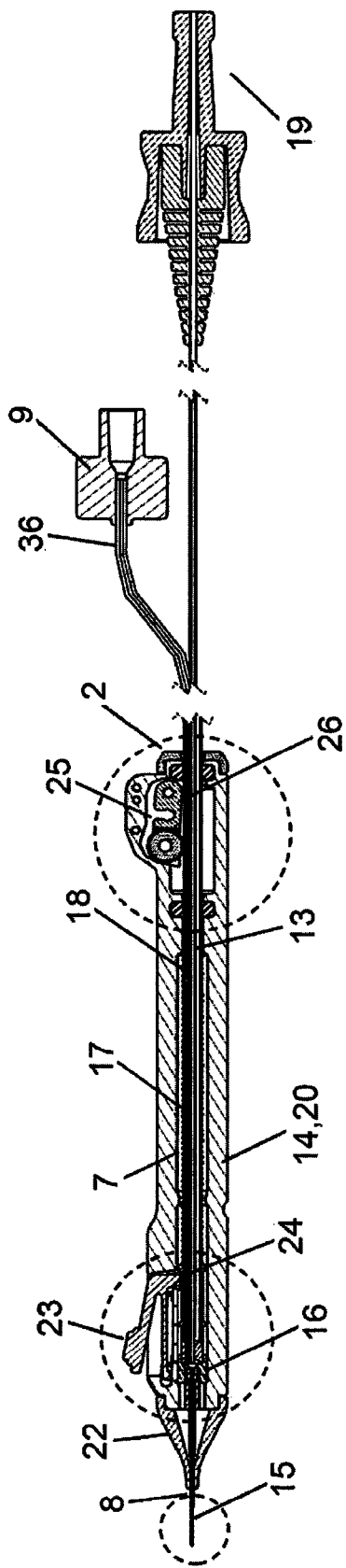
FIG. 3 depicts one embodiment of a cannulation device with an actuation trigger and frictional speed damper for deploying a flexible cannula into a tissue space of an eye.

The invention is a material for administration which may be a fluid, semi-solid or solid composition of an active agent for delivery into the suprachoroidal space, supraciliary space or other spaces of the eye such as the vitreous cavity, subconjunctival space, sub-Tenon's space and sub-retinal space. The active agent may be solubilized, dispersed or suspended in a fluid or semi-solid formulation. Alternatively, the active agent may be formulated as a solid composition. The active agent may also be distributed in the composition as particles. In one embodiment, the composition comprises a plurality of drug-containing particles 53 formed into a semi-solid 54, shown schematically in FIG. 13.

For delivery of the semi-solid composition with active agent containing particles in the suprachoroidal space or supraciliary space, the composition is placed into the eye from the outer surface of the eye through the cannula to preferentially locate the material in the suprachoroidal space or supraciliary space near the distal end of the cannula. After placement in the suprachoroidal space or the supraciliary space, the semi-solid composition transforms, degrades or dissolves into individual drug-containing particles that may migrate in the space to distribute the active agent. The semi-solid mass of drug particles allows a large amount of drug to be injected in a very small volume to prevent an acute increase of intraocular pressure such as occurs with administration of an equivalent amount of drug suspended in a fluid. The semi-solid formulation enables an effective amount of drug to be delivered in the range of to 100 microliters, 10 to 50 microliters or 15 to 40 microliters.

In one embodiment, the composition comprises a plurality of drug-containing particles 53 fashioned into a formed solid 55, shown schematically in FIG. 14 and FIG. 14A. The formed solid 55 comprising the plurality of drug-containing particles 53 may be in the shape of a plug, tube or cylinder. In one embodiment, the formed solid is an elongated body with a diameter approximately the inside diameter of the cannula used for placement of the formed solid in the tissue space. The diameter may range from 0.60 mm (0.02 inches) to 0.159 mm (0.006 inches). Depending on the dose of active agent and active agent content of the particles, the formed solid may have a length ranging from 1 mm (0.04 inches) to 50 mm (2 inches) or for example 1 mm (0.04 inches) to 25 mm (1 inch). The formed solid resides within the lumen of the cannula and is delivered from the cannula by hydraulic, pneumatic or mechanical force from the device. After placement in the suprachoroidal space or the supraciliary space, the formed solid composition transforms, degrades or dissolves into individual active agent containing particles that may migrate in the space. The formed solid mass of particles allows a large amount of active agent to be injected in a very small volume to prevent an acute increase of intraocular pressure such as occurs with administration of an equivalent amount of active agent suspended in a fluid. The volume of the injected formed solid may range from 0.1 microliters to 10 microliters or for example 0.1 to 5 microliters.

In one embodiment, the active agent or drug is combined with a biodegradable polymer to form the drug containing particles. The biodegradable polymer may be selected from the group consisting of polyhydroxybutyrate, polydioxanone, polyorthoester, polycaprolactone, polycaprolactone copolymers, polycaprolactone-polyethylene glycol copolymers, polylactic acid, polyglycolic acid, polylactic-glycolic acid copolymer and/or polylactic-glycolic acid-ethylene oxide copolymer.

In another embodiment the drug is present in an amount from 0.5 wt % to 70.0 wt % of the biodegradable polymer and drug composition, suitably, 10.0 wt % to 55.0 wt %, 20.0 wt % to 50.0 wt %, preferably 30.0 wt % to 50.0 wt %. Suitable drugs are discussed below.

In a further embodiment the drug containing particles are combined with a soluble, biodegradable or bioerodible excipient. The soluble, biodegradable or bioerodable excipient is present in an amount from 0.3 wt % to 90.0 wt %, suitably 0.3 wt % to 70.0 wt %, 0.3 wt % to 50.0 wt % or 0.3 wt % to 30.0 wt %, 0.3 wt % to 20.0 wt %. In one embodiment the excipient is a viscoelastic polymer. In another embodiment the soluble, biodegradable or bioerodable excipient may be selected from the group consisting of polyvinylpyrrolidone, polyvinylpyrrolidone co-vinyl acetate, polyvinyl alcohol, chemically modified cellulose, alginate, polyethylene glycol, polyethylene oxide, hyaluronic acid, chondroitin sulfate, dermatin sulfate and sodium alginate or combinations thereof. The composition of the drug containing particles with the soluble, biodegradable or bioerodable excipient is formulated to have the properties of a semi-solid composition when prepared for administration in a physiologically acceptable solvent or diluent. Alternatively, the composition of the drug containing particles with the soluble, biodegradable or bioerodable excipient may be prepared in a physiologically acceptable solvent or diluent and subsequently dried to produce a formed solid for administration. The hyaluronic acid may have a molecular weight of between 0.5 MW to 1.7 MW, suitably 0.7 MW to 1.5 MW, suitably 1 MW. The molecular weight of hyaluronic acid may be measured by a viscosity measurement or using size-exclusion chromatography.

In one embodiment, the semi-solid drug composition is lyophilised with a bulking agent to aid reconstitution with a solvent or diluent prior to administration. The bulking agent is present in an amount from 5.0 wt % to 50.0 wt %, suitably 10.0 wt % to 40.0 wt %, 20.0% to 30.0% of the composition prior to lyophilisation. The bulking agent may be selected from the group consisting of mannitol, maltitol, sorbitol, maltose, lactose, glucose, fructose, galactose, sucrose and polymers of sucrose, for example dextran, or combinations thereof. The lyophilized semi-solid drug composition is reconstituted by the addition of a suitable solvent or diluent such as water or buffer.

In one embodiment, the semi-solid drug composition is lyophilised with a reconstitution aid to speed mixing to a uniform semi-solid composition with a solvent or diluent prior to administration. The reconstitution aid is present in an amount from 0.1 wt % to 45.0 wt %, suitably from 0.1 wt % to 30.0 wt %, 1.0 wt % to 40.0 wt %, 5.0 wt % to 30.0 wt %. The reconstitution aid may be selected from the group consisting of surfactants, trehalose, maltitol, sorbitol, maltose, lactose, glucose, fructose, galactose, sucrose and polymers of sucrose, for example dextran, or combinations thereof.

In a further embodiment the semi-solid drug composition may comprise a salt. The salt may be selected from the group consisting of sodium phosphate, potassium phosphate, sodium chloride, sodium carbonate, potassium carbonate, sodium acetate or potassium acetate and combinations thereof. The salts or combination of salts may be formulated to provide physiological acceptable pH and osmolality. The combination of salts may also be phosphate buffered saline.

In a further embodiment the drug containing composition may comprise an amphiphilic polymer. The amphiphilic polymer may be selected from gelatin, collagen, glycosaminoglycan, cellulose, chemically modified cellulose, dextran, alginate, chitin and chemically modified chitin. Preferably the amphiphilic compound may be a natural or synthetic hydrophilic polymeric substance. The compound may be suitably biocompatible and/or biodegradable. Exemplary materials, include polyvinylpyrrolidone, e.g. non-cross-linked polyvinylpyrrolidone (e. g. of molecular weight 30,000-400,000), hydroxypropylcellulose with a molecular weight of from 100,000 to 4,000, 000, sodium carboxymethylcellulose (e. g. non-cross-linked, e. g. typical molecular weight 90,000-700,000) and/or calcium carboxymethylcellulose, carboxymethylstarch, potassium methacrylate-divinylbenzene copolymer, hydroxypropyl methylcellulose with a molecular weight between 2, 000 and 4, 000, 000, polyethyleneglycols of different molecular weight preferably between 200 and 15, 000 (more preferably 1000-15000) and polyoxyethylenes of molecular weight up to 20, 000, 000 (more preferably 400, 000-7, 000, 000), carboxyvinylpolymers, poloxamers (polyoxyethylene-polyoxypropylene copolymer), polyvinylalcohols, glucanes (glucans), carrageenans, scleroglucanes (scleroglucans), mannans, galactomannans, gellans, xanthans, alginic acid and derivatives (e. g. sodium or calcium alginate, propylene glycol alginate), polyaminoacids (e. g. gelatin), methyl vinyl ether/maleic anhydride copolymer, carboxymethylcellulose and derivatives (e. g. calcium carboxymethylcellulose), ethylcellulose, methylcellulose, starch and starch derivatives, alpha, beta or gamma cyclodextrin, and dextrin derivatives (e. g. dextrin) in general. The amphiphilic compound may therefore act as a controlled release polymer being a polymeric substance which is capable of achieving controlled release (CR).

In a further embodiment the drug containing composition may comprise a lipid, a fatty acid or a lipid conjugate selected from the group consisting of capric acid, erucic acid, 1,2-dinervonoyl-sn-glycero-3-phosphocholine, 1,2-dimyristoyl-sn-glycero-3-phosphocholine and 1,2-dipentadecanoyl-sn-glycero-3-phosphocholine.

In one embodiment the drug composition comprises a drug in the amount of 0.5 wt % to 70.0 wt %, a biodegradable polymer in the amount of 3.0 wt % to 80.0 wt %, a soluble, biodegradable or bioerodible excipient in the amount of 0.3 wt % to 90.0 wt %, a bulking agent in an amount of 5.0 wt % to 50.0 wt % and a reconstitution aid in the amount of 0.1 wt % to 45.0 wt %.

In one embodiment the drug composition comprises dexamethasone, polylactic-glycolic acid copolymer, hyaluronic acid, mannitol, trehalose and sodium phosphate.

The particles of active agent may be in the form of a selected size range of crystals of the active agent. The particles of active agent may be in the form of microspheres by fabrication of the active agent into the form of spherical particles or by the formulation of the active agent with a polymer and fabricating microspheres from the combination. Microspheres containing active agent may be fabricated by any of the known means for microsphere fabrication such as by spray drying, emulsion or coacervation. The use of a non-toxic polymer to hold active agent within microspheres allows tailoring of the active agent release rate by the polymer composition, active agent content and size of the microspheres. Microspheres with an active agent content of 0.5 wt % to 70.0 wt % may provide appropriate release. In some embodiments, the weight % may be 5.0 wt % to 50.0 wt %, 10.0 wt % to 45.0 wt %, 15.0 wt % to 45.0 wt %, 20.0 wt % to 40.0 wt %, 25.0 wt % to 35.0 wt %. The use of polymers of selected solubility allows both water soluble and water insoluble active agents to be incorporated into microspheres. Suitable polymers include, but are not limited to, non-toxic water soluble polymers such as polyvinylpyrrolidone, polyvinylpyrrolidone co-vinyl acetate, polyvinyl alcohol, polyethylene glycol and polyethylene oxide, biodegradable polymers such as polyhydroxybutyrate, polydioxanone, polyorthoester, polycaprolactone, polycaprolactone copolymers, poly lactic acid, poly glycolic acid, poly lactic-glycolic acid copolymers, poly lactic-glycolic acid-ethylene oxide copolymers, and biological polymers such as gelatin, collagen, glycosaminoglycans, cellulose, chemically modified cellulose, dextran, alginate, chitin and chemically modified chitin.

In particular, for hydrophobic active agents, microspheres in the size range of 1 to 50, 2 to 25, 2 to 20, 2 to 15 or 3 to 14 micron mean volumetric diameter composed of polylactic-glycolic acid copolymers with a lactate to glycolic stoichiometry (L to G) of 75:25 and 85:15 have been found to provide release half-life ranging from 12 to 80 weeks in laboratory testing. The small diameter of the microspheres allows injection through small gauge needles and cannulas for minimally invasive administration of an active agent. In another embodiment, the L to G stoichiometry is 50:50 or 65:35.

With microspheres of relatively narrow size distribution, for example a coefficient of variation in the range of 10% to 25%, the rate of drug release may be tuned by the mean microsphere size. The polymer selection and form of the active agent in the microspheres, such as crystalline or amorphous solid dispersion, provides a general range of release that may be effectively tailored by the use of microsphere size selection.

Alternatively, active agent particles of approximately spherical shape or other uniform shapes may be prepared by milling of larger active agent particles or by controlled crystallization. Active agent particles and active agent containing microspheres may also be individually coated with a polymer layer to form active agent particles with an external surface coating or barrier coating. The coatings may comprise non-toxic water soluble polymers including, but not limited to, polyvinylpyrrolidone, polyvinylpyrrolidone co-vinyl acetate, polyvinyl alcohol, polyethylene glycol and polyethylene oxide, biodegradable polymers such as polyhydroxybutyrate, polydioxanone, polyorthoester, polylactic acid, polyglycolic acid, poly lactic-glycolic acid copolymers, acid terminated polylactic-glycolic acid copolymers, polylactic-glycolic acid-ethylene oxide copolymers, polylactic acid-polyethylene glycol copolymers, polycaprolactone, polycaprolactone copolymers and polycaprolactone-polyethylene glycol copolymers, and biological materials such as gelatin, collagen, glycosaminoglycans, cellulose, chemically modified cellulose, dextran, alginate, chitin, chemically modified chitin, lipids, fatty acids and sterols.

In one embodiment, the plurality of active agent containing particles is formed into a semi-solid composition that flows upon application of injection pressure but once administered into tissue, forms a semi-solid material at the location of delivery. A semi-solid form with a high concentration of the active agent containing particles, in the range of 70 to 200 mg per ml, provides the ability to deliver sufficient amounts of the active agent to provide a sustained delivery of therapeutic levels. The ability to administer the composition through a small gauge needle or cannula is aided by the use of microspheres or spherical particles to minimize aggregation during injection. The ability to inject a semi-solid with high particle concentration is enabled with the use of excipients that suspend the particles in an semi-solid or aqueous formulation but also provide viscoelastic properties to promote particle flow during injection. Suitable viscoelastic excipients include polyethylene glycol, polyethylene oxide, high molecular weight polyvinylpyrrolidone, and biological polymers such as polymeric lipids, hyaluronic acid and chondroitin sulfate. Viscoelastic excipients in the concentration range of 0.3 wt % to 90 wt % percent depending on polymer selection and molecular weight provide injectable semi-solid compositions. In one embodiment, the semi-solid is formulated with 70 to 200 mg per ml of microspheres and an excipient mixture comprising a viscoelastic excipient and a physiological buffer. In one embodiment the semi-solid material comprises an excipient that undergoes dissolution, biodegradation or bioerosion in the suprachoroidal space or supraciliary space after injection. Dissolution of the semi-solid material after injection may result in migration into the suprachoroidal space.

In one embodiment, the plurality of active agent containing particles is formed into a solid or semi-solid with a soluble, biodegradable or bioerodable excipient. Suitable excipients include, but are not limited to, non-toxic water soluble polymers such as polyvinylpyrrolidone, polyvinylpyrrolidone co-vinyl acetate, polyvinyl alcohol, polyethylene glycol and polyethylene oxide, chemically modified cellulose, alginate, hyaluronic acid, chondroitin sulfate, dermatin sulfate or sodium alginate, biodegradable polymers such as polyhydroxybutyrate, polydioxanone, polyorthoester, polycaprolactone, polycaprolactone copolymers, polylactic acid, polyglycolic acid, polylactic-glycolic acid copolymers and polylactic-glycolic acid-ethylene oxide copolymers, and biological materials such as gelatin, collagen, glycosaminoglycans, cellulose, chemically modified cellulose, dextran, alginate, chitin and chemically modified chitin, bioerodible materials, an amphiphilic compound, a lipid, a fatty acid, or a lipid conjugate. The solid or semi-solid composition may be formulated with a mixture of different excipients. The particles containing active agent are mixed with the excipient in a suitable solvent or diluent such as water or physiological buffer that dissolves or forms a dispersion of the excipient, but does not rapidly extract the drug from the particles or dissolve the particles. In one embodiment, a semi-solid composition is administered as a mixture, dispersion or suspension with a solvent. In one embodiment, the solid or semi-solid composition is formed in a mold or extruded and allowed to dry to form a solid of desired dimensions for administration. Ideal for administration of the formed solid or semi-solid composition is an elongated shape with an outer diameter sized to fit within the lumen of a small diameter cannula or needle, 20 gauge or smaller, corresponding to 0.60 mm (0.02 inches) diameter or smaller. In one embodiment, the formed solid or semi-solid composition has an outer diameter sized to fit within the lumen of a 25 gauge or smaller cannula or needle, corresponding to a 0.26 mm (0.01 inches) diameter or smaller. In one embodiment, the formed solid or semi-solid composition has an outer diameter sized to fit within the lumen of a 27 gauge or smaller cannula or needle, corresponding to a 0.20 mm (0.008 inches) diameter or smaller.

In one embodiment, the semi-solid composition is dried, such as by lyophilisation or air drying, for rehydration prior to administration. The semi-solid composition may have excipients to aid reconstitution such as salts, sugars, water soluble polymers and surfactants. For lyophilisation formulations, the use of bulking agent such as sucrose, mannitol, glycine, povidone, or dextran, aids the production of a loose lyophilized product with large channels or pores to enhance reconstitution speed. Prior to lyophilisation, the bulking agent may be in the concentration range of 1.0 wt % to 20.0 wt %, 1.0 wt % to 10.0 wt % in the excipient mixture. The final dried composition may have a bulking agent in the range of 5 to 50 wt %. Excipients to increase reconstitution of the lyophilized composition to act as reconstitution aids, such as surfactants, salts, sugars or trehalose may be added prior to freezing and lyophilisation. The final dried composition may have a reconstitution aid in the range of, 0.1 wt % to 45.0 wt %, 0.1 wt % to 20.0 wt %, 1.0 wt % to 15.0 wt % or 2.0 wt % to 10.0 wt %. In one embodiment, the semi-solid composition comprises microspheres containing an active agent, a viscoelastic polymer, a bulking agent, and physiological buffer that is lyophilized to produce a dry product to enhance shelf-life stability. The composition may be reconstituted with water or a physiological buffer immediately prior to use. In one embodiment, the semi-solid composition comprises microspheres containing an active agent, a viscoelastic polymer and a bulking agent that is lyophilised to produce a dry product to enhance shelf-life stability. The composition may be reconstituted with water or a physiological buffer immediately prior to use. In one embodiment the composition may additionally contain an excipient to speed reconstitution such as trehalose. The combination of the components must be carefully balanced to provide the physical stability to lyophilize the composition without particle aggregation, rapid rehydration, physical properties to provide reconstituted stability without particle aggregation, flow properties for administration through a small lumen while also providing physiologically compatible osmolality, generally in the range of 250 to 450 mOsM, and pH, generally in the range of 7 to 8.

In one embodiment, the active agent containing particles are sized smaller than the inner diameter of the cannula to allow close packing of the particles within a formed solid or semi-solid to enhance mechanical properties. Such active agent containing particles would have an average diameter in the range of 5 to 100 microns, for example 10 microns to 50 microns, and may comprise a mixture of diameters to facilitate close packing. The mean or median diameter of the particles may be in the range of 1 microns to 100 microns, for example 2 microns to 50 microns, 3 microns to 40 microns, 3 microns to 30 microns or 3 microns to 20 microns.

The dispersion and migration of the particles containing active agent are desired to promote a uniform distribution of the particles in the eye. The dissolution of the excipient and resultant release of active agent containing particles may be triggered by the absorption of fluid from the tissue space, for example due to the ionic environment, dissolution of an excipient or the temperature of the environment. In one embodiment, the excipient comprises a lipid or fatty acid with a melting temperature between room temperature and the temperature of the ocular tissues space, approximately 37 degrees centigrade (for example, a melting temperature between 21 and 37 degrees centigrade, between 25 and 37 degrees centigrade, or between to 35 degrees centigrade). The rate of release of the individual active agent containing particles from the solid or semi-solid composition may be tailored by the addition of hydrophilic or amphiphilic agents that increase the dissolution rate of the excipients of the solid or semi-solid composition. The release of the active agent containing particles may occur over hours, days or weeks, depending on the amount and composition of the material for administration. For example, a maximum (or minimum, depending on the formulation) of 50% of the active agent containing particles may be released after 1 hour, 6 hours, 12 hours, 1 day, 3 days or 1 week.

The solid or semi-solid composition may be acted upon by the ionic environment of the tissue space to provide dissolution, as may be provided by ionically crosslinked polymers such as sodium alginate. The solid or semi-solid composition may be triggered for dissolution in the tissue space by temperature, such as with lipids and fatty acids with a melt transition temperature greater than room temperature, approximately 20 degrees centigrade, and less than or equal to the temperature within the ocular tissue space, approximately 37 degrees centigrade. Such lipids and fatty acids include, but are not limited to, capric acid, erucic acid, 1,2-dinervonoyl-sn-glycero-3-phosphocholine, 1,2-dimyristoyl-sn-glycero-3-phosphocholine, and 1,2-dipentadecanoyl-sn-glycero-3-phosphocholine and mixtures thereof.

Due to the small size of the active agent containing particles, active agent release from the particles may be too rapid to provide sustained active agent effect after administration to the eye. It is an object of the invention to provide active agent containing particles with prolonged release kinetics (i.e. controlled release formulations). In one embodiment the active agent is incorporated into a polymer matrix that creates a poor diffusion path for the drug thereby slowing active agent release as compared to the active agent without a polymer matrix. In one embodiment, the active agent containing particle is coated with a barrier such as a polymer or other compound. The barrier material typically has different chemical properties than the active agent so that the active agent is not readily soluble through the barrier coating and is slowed in active agent release as compared to the active agent containing particle without a barrier coating. One method for selection of the barrier coating is a material with a different partition coefficient or log P than the active agent, with an increased difference providing an increased barrier to active agent release. In one embodiment the individual particles of an active agent are coated with a barrier coating of increased water solubility or decreased log P compared to the active agent, to form a barrier coating on each particle. In one embodiment the barrier coating has a higher partition coefficient than the drug or less water solubility than the drug. In another embodiment the barrier coating has a lower partition coefficient than the drug or greater water solubility than the drug. Barrier materials may include, but are not limited to, non-toxic water soluble polymers including, polyvinylpyrrolidone, polyvinylpyrrolidone co-vinyl acetate, polyvinyl alcohol, polyethylene glycol and polyethylene oxide, biodegradable polymers such as, polyorthoester-ethylene oxide copolymers, acid terminated polylactic-glycolic acid copolymers, polylactic-glycolic acid-ethylene oxide copolymers, polylactic acid-polyethylene glycol copolymers and polycaprolactone-polyethylene glycol copolymers, and biological materials such as gelatin, collagen, glycosaminoglycans, cellulose, chemically modified cellulose, dextran, alginate, chitin and chemically modified chitin. In one embodiment, the individual particles of an active agent are coated with a barrier coating of decreased water solubility or increased log P compared to the active agent to form a barrier coating on each particle including, but not limited to, biodegradable polymers such as polyhydroxybutyrate, polydioxanone, polyorthoester, polylactic acid, polyglycolic acid, poly lactic-glycolic acid copolymers, acid terminated polylactic-glycolic acid copolymers, polylactic-glycolic acid-ethylene oxide copolymers, polylactic acid-polyethylene glycol copolymers, polycaprolactone, polycaprolactone copolymers and polycaprolactone-polyethylene glycol copolymers, and biological materials such as chemically modified chitin, lipids, fatty acids and sterols. In one embodiment the lipid or fatty acid comprises capric acid, erucic acid, 1,2-dinervonoyl-sn-glycero-3-phosphocholine, 1,2-dimyristoyl-sn-glycero-3-phosphocholine, or 1,2-dipentadecanoyl-sn-glycero-3-phosphocholine. Active agent particles may be coated by any of the known means for particle coating, for example, spray drying, electrostatic spraying or chemical deposition. In one embodiment, shown schematically in FIG. 14 and FIG. 14A, the formed solid or semi-solid material 54 comprises a plurality of active agent particles 53 encapsulated or coated with a barrier material 54, such as a soluble polymer or other coating, to modify the active agent release characteristics and/or the mechanical properties.

While the active agent of the composition is primarily contained in the plurality of particles, some active agent may also be formulated into the excipient. The active agent in the excipient may act to prevent or limit extraction or diffusion of active agent from the particles during processing or storage. The active agent in the excipient may also act to provide a rapid release component to the active agent formulation to initiate therapeutic effect of the active agent while allowing the active agent in the particles to provide a sustained release to maintain the treatment effect.

In one embodiment, the active agent composition comprises an active agent and an excipient comprising a biodegradable or bioerodible material. The biodegradable or bioerodible material may be comprised of, for example but not limited to, polyhydroxybutyrate, polydioxanone, polyorthoester, polycaprolactone, polycaprolactone copolymer, polycaprolactone-polyethylene glycol copolymer, polylactic acid, polyglycolic acid, polylactic-glycolic acid copolymer, acid terminated polylactic-glycolic acid copolymer, or polylactic-glycolic acid-ethylene oxide copolymer, gelatin, collagen, glycosaminoglycan, cellulose, chemically modified cellulose, dextran, alginate, chitin, chemically modified chitin, lipid, fatty acid or sterol.

The active agent may be dispersed in the biodegradable or bioerodible material as an amorphous solid dispersion. The active agent may be dispersed in the biodegradable or bioerodible material as a plurality of crystals. The active agent may be dispersed in the biodegradable or bioerodible material as both an amorphous solid dispersion and as crystals. The active agent composition may be shaped as an elongate solid body or a semi-solid for administration into the ocular tissue space. After placement in tissue, release of the active agent from the composition allows the active agent to diffuse into the tissues of the eye and may be assisted by the flow of fluid in the tissue space. In the case where the active agent is in the form of a solid amorphous dispersion, the biodegradable or bioerodible material is selected to provide the desired active agent loading and release characteristics of the active agent. In the case where the active agent is in the form of dispersed crystals, the amount of active agent, the biodegradable or bioerodible material characteristics and the crystal form of the active agent may be selected to provide the desired active agent loading and release characteristics. The active agent crystals may also be coated with an excipient to reduce the active agent release rate of the composition. In the case where the active agent release is initiated by contact with moisture in the hydrated tissue environment, the active agent composition is administered as a dry solid composition or as a lyophilized formulation that is reconstituted immediately prior to use. In one embodiment, the composition has an extended release of the active agent. The active agent elution from the composition may have a half-life in the range of 14 to 360 days, 21 to 270 days, 30 to 180 days, or 60 to 90 days.

A variety of drugs as active agents may be delivered by the present invention to the eye for the treatment of ocular diseases and conditions including inflammation, infection, macular degeneration, retinal degeneration, neovascularization, proliferative vitreoretinopathy, glaucoma and edema. Useful drugs include, but are not limited to, steroids, non-steroidal anti-inflammatory agents, anti-histamine agents, antibiotics, VEGF inhibitors, PDGF inhibitors, anti-TNF alpha agents, mTOR inhibitors, prostaglandin analogs, cell therapies, neuroprotective agents, anti-hypertensive agents, antihistamines, aminosterols and nucleic acid based therapeutics. The drugs may be in the form of soluble solutions, suspensions, gels, semi-solids, microspheres, formed solids or implants.

In one embodiment, the active agent composition is preloaded in the device prior to use during the time of manufacture. In one embodiment, the active agent composition is loaded in the device by the user just prior to use. The source of force to provide a deployment force to the cannula may be activated just prior to or simultaneous with use. In one embodiment the activation is achieved by a mechanism to preload the force element, such as compressing a spring, from the exterior of the device such as by a movable proximal handle attached to the plunger. In one embodiment, the source of force is preloaded during manufacture and the preloaded force is stabilized by means of a stop mechanism. Prior to or simultaneous with use, the stop mechanism is released, thereby placing the deployment force on the cannula prior to contact or penetration of the eye and the cannula deployment is triggered by the advancement of the needle into the eye.

As noted, a variety of drugs as active agents may be delivered by the present invention to the eye for the treatment of a variety of ocular diseases and conditions including inflammation, cancer, infection, macular degeneration, retinal degeneration, neovascularization, proliferative vitreoretinopathy, glaucoma, and edema. Useful drugs include, but are not limited to, steroids such as corticosteroids including dexamethasone, fluocinolone, loteprednol, difluprednate, fluorometholone, prednisolone, medrysone, triamcinolone, betamethasone and rimexolone; beclomethasone dipropionate, budesenide, fluticasone dipropionate, mometasone furoate or ciclesonide; non-steroidal anti-inflammatory agents such as salicylic-, indole acetic-, aryl acetic-, aryl propionic- and enolic acid derivatives including bromfenac, diclofenac, flurbiprofen, ketorolac tromethamine and nepafenac; anti-histmaine agents including cetirizine, loratadine, Fexofenadine HCl, olopatadine, alcaftadine, epinastine or ketotifen; antibiotics including azithromycin, bacitracin, besifloxacin, ciprofloxacin, erythromycin, gatifloxacin, gentamicin, levofloxacin, moxifloxacin, ofloxacin, sulfacetamide and tobramycin; VEGF inhibitors such as tyrosine kinase inhibitors, antibodies to VEGF, antibody fragments to VEGF, VEGF binding fusion proteins; PDGF inhibitors, antibodies to PDGF, antibody fragments to PDGF, PDGF binding fusion proteins; anti-TNF alpha agents such as antibodies to TNF-alpha, antibody fragments to TNF-alpha and TNF binding fusion proteins including infliximab, etanercept, adalimumab, certolizumab and golimumab; mTOR inhibitors such as sirolimus, sirolimus analogues, Everolimus, Temsirolimus and mTOR kinase inhibitors; cell therapies such as mesenchymal cells or cells transfected to produce a therapeutic agent; glaucoma agents such as prostaglandin analogs, beta blockers, alpha agonists, carbonic anhydrase inhibitors, and rho kinase inhibitors; oncology agents such as melphalan, topotecan, methotrexate, rituximab, carboplatin and 5-FU; neuroprotective agents such as antioxidants, calcineurin inhibitors, NOS inhibitors, sigma-1 modulators, AMPA antagonists, calcium channel blockers, DNA gyrase inhibitors, DNA polymerase inhibitors, RNA polymerase inhibitors and histone-deacetylases inhibitors; antihypertensive agents such as prostaglandin analogs, beta blockers, alpha agonists, and carbonic anhydrase inhibitors; aminosterols such as squalamine; antihistamines such as H1-receptor antagonists and histamine H2-receptor antagonists; therapeutic proteins and nucleic acid based therapeutics such as gene vectors, gene editing therapeutics, plasmids, therapeutic mRNA, guide RNA and siRNA.

In one embodiment the drug composition may suitably be present in a substantially dry form and can be considered to be free from water. The drug composition may be dried using any generally convenient process including lyophilisation. The drug composition may be considered as anhydrous after drying but it is not excluded that a small amount of residual moisture may be present.

In another aspect a pharmaceutical formulation comprising the drug composition and a pharmaceutically acceptable diluent are provided. The pharmaceutically acceptable diluent may comprise salt to provide physiologically acceptable osmolality and pH to the drug composition prepared with the diluent. The pharmaceutically acceptable diluent may contain a reconstitution aid to promote rapid reconstitution of the drug composition in dry form.

In a further aspect a unit dosage form comprising the pharmaceutical formulation is provided.

In another aspect there is provided a kit of parts comprising the drug composition and a pharmaceutically acceptable diluent. In one embodiment there is further provided a cannulation device. There is also provided a kit of parts comprising a pharmaceutical formulation and a cannulation device.

There is also provided an aspect of a method for preparing a pharmaceutical formulation or a unit dosage form comprising mixing the drug composition and a pharmaceutically acceptable diluent.

In another aspect there is provided a method of treatment of a disease or condition.

In one embodiment the method of treatment of a disease or condition comprises delivery of a drug composition to an affected region comprising: administering the drug composition to a subject in need thereof.

In one embodiment the disease or condition is inflammation or infection. The inflammation may be selected from the group consisting of sinusitis, osteoarthritis, rheumatoid arthritis, joint inflammation, rhinitis or post-operative inflammation.

In another embodiment the disease or condition is an ocular disease or condition. The ocular disease or condition may be selected from the group consisting of blepharitis, allergic conjunctivitis, macular degeneration, retinal degeneration, neovascularization, proliferative vitreoretinopathy, glaucoma, ocular tumor, uveitis or edema.

In one embodiment the method for the treatment of an ocular disease or condition comprises delivery of the drug composition to the suprachoroidal space or supraciliary space of an eye comprising: administering the drug composition to a subject in need thereof.

In a further embodiment the method comprises administering the drug composition or the unit dosage form through a needle, cannula or cannulation device. In one embodiment the unit dosage form is adapted for insertion into the cannulation device.

In another embodiment the method comprises preparing the drug composition by mixing with a pharmaceutically acceptable diluent before administration.

In a further aspect the method for the treatment of a disease or condition comprises: preparing the pharmaceutical formulation or the unit dosage form before administration; and administering the pharmaceutical formulation or unit dosage using a cannulation device.

In another aspect there is provided a drug composition for use in the treatment of a disease or condition.

In one embodiment, the disease or condition is inflammation or infection. The inflammation may be selected from the group consisting of sinusitis, osteoarthritis, rheumatoid arthritis, joint inflammation, rhinitis and post-operative inflammation or a combination thereof.

In one embodiment the disease or condition is an ocular disease or condition. The ocular disease or condition may be selected from the group consisting of blepharitis, allergic conjunctivitis, macular degeneration, retinal degeneration, neovascularization, proliferative vitreoretinopathy, glaucoma, ocular tumor, uveitis or edema.

In one embodiment of the invention, there is provided the drug composition of the invention for use in medicine, in particular for use in ocular medicine. In a further embodiment of the invention, there is provided the drug composition of the invention for use in the treatment of an ocular disease or condition. The ocular disease or condition may be inflammation, infection, macular degeneration, retinal degeneration, neovascularization, proliferative vitreoretinopathy, glaucoma, uveitis, an ocular tumor or edema. In some embodiments, the drug composition is administered by delivery through a cannula, in particular a cannula placed by the cannulation device of the present invention.

In one embodiment there is provided a method of treating an ocular disease or condition by administration of a drug composition by a cannulation device of the present invention to the eye, for example to the suprachoroidal space or to the supraciliary space. The drug composition may dissolve or transform into a plurality of drug-containing particles that migrate from the site of administration (for example the suprachoroidal space or supraciliary space) after administration. The ocular disease or condition may be inflammation, infection, macular degeneration, retinal degeneration, neovascularization, proliferative vitreoretinopathy, glaucoma, an ocular tumor or edema.

In another embodiment of the invention there is provided a kit of parts comprising the cannulation device described herein and the drug composition of the invention. The drug composition may be provided preloaded into the delivery device. Alternatively, the drug composition may be provided as a discrete dosage form suitable for insertion into the delivery device. Therefore, a kit may also provide the drug composition of the invention in the form of a discrete dosage form along with the cannulation device.

The described device provides minimally invasive cannulation of the suprachoroidal space or supraciliary space. Subsequent to the cannulation, the device may be used to deliver a material for administration such as an active agent containing composition into the space through the cannula. In particular, the material for administration is a fluid, suspension, semi-solid or solid active agent containing composition. The active agent may be a substance that provides a therapeutic or diagnostic effect for treatment of an eye. The active agent may comprise a drug, a diagnostic agent, gene therapy agents, therapeutic cells or means for physical tissue repair.

Placement of a cannula into the suprachoroidal space or supraciliary space of an eye provides a means to deliver an active agent containing composition to a location in the space distant from the site of tissue penetration. The cannulation device of the present invention allows an active agent containing composition to be administered and directed toward the posterior retina from an anterior tissue access site such as the pars plana. The cannulation device may also be designed and used to deliver an active agent containing composition to a specific site in the eye to treat a local condition such as a tumor.

The cannulation device comprises an elongated barrel with a hollow needle at the distal end and a cannula comprising an elongated tubular element, where the lumen of the needle serves as the reservoir for at least a portion of the tubular element. The device also comprises a deployment mechanism to advance the cannula through the needle lumen and the distal portion of the cannula out from the distal end of the needle. The mechanism may be mechanically coupled to the cannula by a push rod or plunger between the push rod and the cannula. Alternatively, the end of the mechanism may be directly mated to a section of the cannula. The mechanism may be activated manually by a finger when holding the device such as with a sliding actuator or a lever on the body of the device. The manual activation allows for fine control of the speed and extent of deployment of the cannula by the user.

In one embodiment, the cannulation device comprises a force element such as a spring or gas reservoir that provides a force to advance or deploy the cannula through the needle lumen and out from the distal end of the needle into a tissue space. The force element may be mechanically coupled to the cannula by a push rod or plunger between the push rod and the cannula. Alternatively, the end of the force element may be directly mated to a section of the cannula. The force element, force element plunger or force element push rod may be connected to the cannula by an interfacing sleeve or other forms of attachment. Prior to use, the distal portion of the cannula is within the needle and body of the cannulation device. The cannula is configured to extend from the distal tip of the needle once deployed by the force element. The cannula has a length to allow extension of the distal end of the cannula from the distal tip of the needle when deployed. The cannula is configured with a deployed length from the distal tip of the needle to the intended site of delivery of an active agent containing composition. In one embodiment, the length of the cannula from the distal tip of the needle in the deployed state ranges from 2 mm (0.08 inches) to 15 mm (0.6 inches). A very short deployed length cannula is useful for directing the material for administration in a preferred direction from the needle penetration site. In particular, a deployed length from the distal tip of the needle in the range of 5 mm (0.2 inches) to 12 mm (0.5 inches) allows the cannula to be introduced in the eye at the pars plana to avoid potential damage to the retina and place the distal tip of the cannula near the posterior retina to deliver a material for administration to the most visually important portion of the eye. The deployment force may be activated immediately after or simultaneously with advancement of the needle tip into tissue. The activation may be performed by release of the force element by the user or by a mechanism at the distal tip of the device.

The cannula is sized with a diameter less than or equal to the inner diameter of the needle lumen and is slidably disposed in the needle lumen. The cannula has a proximal end to receive the active agent containing composition and a distal tip to deliver the active agent containing composition. In one embodiment, the distal tip of the cannula is configured with a rounded profile to provide for an atraumatic tip for entering the tissue space without penetration through underlying tissues. The rounded profile may be created by thermal treatment of the distal tip of the cannula, by directly molding the distal tip, laser machining of the tip or by application of additional material to the distal tip. The applied material may be the same as the cannula material in a solvent dispersion, a different material than the cannula material in a solvent dispersion or an adhesive. The atraumatic distal tip may also be formed as a separate component and attached to the distal end of the cannula by thermal or adhesive means. In one embodiment, the distal end of the cannula is curved or bent at an angle when unconstrained. The curved or bent cannula is straightened when placed in the lumen of the needle but regains its unconstrained configuration once deployed from the lumen of the needle thereby directing the cannula tip at an angle from the long axis of the needle, generally in the direction of the needle bevel. The curvature or bend may be used in conjunction with means for identification of the needle bevel orientation to direct the cannula toward the posterior area of the eye, away from the underlying tissues, or both. The cannula may be curved along the entire length or curved or bent at the distal portion of the cannula. The cannula may have a compound curvature, such as a curve in a smaller radius at the distal end as compared to the curve in the proximal portion of the cannula.

In one embodiment, the cannula is illuminated to provide visual guidance of the location of the cannula when in the suprachoroidal or supraciliary spaces. It has been found that an illuminated cannula in the suprachoroidal or supraciliary space is visible through the overlying sclera and conjunctiva. However, if the cannula is located in the intraocular space such as the vitreous, the illumination is not visible through the overlying tissues. A light output of 100 to 700 microwatts ($\mu W$) from the cannula was found to provide good visibility of the cannula location through the sclera and conjunctiva. The cannula may be illuminated by coupling a light source to a fiber optic attached to or within the lumen of the cannula that extends to the distal end of the cannula. In another embodiment, the cannula is illuminated by utilizing a cannula material with a refractive index able to provide total or partial internal reflection, thereby using the cannula as a fiber optic without the encumbrance of the wall, outer diameter or lumen of the cannula with a separate fiber optic. In particular, the use of the cannula walls to conduct light along the length eliminates a fiberoptic within the lumen thereby maximizing the effective luminal diameter and the ability to deliver active agents, especially suspensions of active agents which are sensitive to flow path irregularities. The use of the cannula material to conduct light may be enhanced by the use of reflective or low refractive index coatings on the exterior of the cannula. Illumination of the cannula may be tailored by the use of coatings and the geometry of light introduced into the cannula to illuminate only the distal end of the cannula, the entire length of the cannula or select areas of the cannula. In another embodiment, the cannula is illuminated by directing a light source to the proximal end of the cannula and allowing transmission of light along the walls of the cannula to the distal tip to allow the user to better discriminate the location of the entire length of cannula. Alternatively, the light may be introduced by directing light at an acute bend in the proximal portion of the cannula. The cannula may also incorporate features to illuminate segments or discrete portions of the cannula with a higher intensity than the surrounding portions. For example, grooves or textured rings can be incorporated into the cannula outer surface which would provide bright spots. These spots may serve as depth markers or indicate when the cannula has been fully deployed. By configuring the distal end of the illuminated cannula within the lumen of the needle, the light is projected through the needle lumen to provide a projected light or headlight from the distal end of the device. The headlight illuminates a spot on the tissue directly in line with the needle to provide a target to confirm the location and provide guidance to the user. The illuminated target generally becomes smaller as the distal tip of the needle approaches the tissue surface, providing visual guidance of distance to the tissue surface. Once the bevel of the needle is inserted into the tissue, the headlight becomes absorbed and is no longer visible on the surface of the eye, indicating that the cannula is positioned for activation of the deployment mechanism. The distal end of the cannula is placed in the needle to be located at or just proximal to the proximal end of the needle bevel. A distance of zero to 5 mm from the distal end of the needle bevel to the distal end of the cannula is sufficient to provide a headlight function and responsive deployment of the cannula. The light source may be a separate unit and the light output coupled to the cannulation device and cannula through a fiberoptic connector. Alternatively, the light source may be integrated into the cannulation device. Illumination of the cannula and observation of the location of the cannula through the overlying tissues while activation of cannula deployment provides control and confidence in cannulating the desired tissue space. The light source may be any light emitting device such as a halogen light source, LED light source, or laser light source.

In another embodiment, the material for administration such as an active agent containing composition is directed into the proximal end of the cannula from a connector, such as a Luer connector or an injection port in communication with the proximal end of the cannula. The connector or injection port may be located on the device or attached to the device. In another embodiment, the material for administration such as an active agent containing composition is located in a reservoir in the body of the cannulation device and a path for transfer of the material for administration connects the reservoir to the lumen of the cannula. The size of the reservoir may be configured appropriately for the volume of material to be delivered. The reservoir may be sized for delivery volumes ranging from, for example, 0.1 microliters to 500 microliters. The material for administration in the reservoir may be delivered manually by a plunger or by actuation of a force element acting on a plunger to move a plunger in the reservoir and provide a delivery force on the material for administration. For small volumes of administration, the lumen of the cannula may also act as a reservoir for the active agent containing composition. For small volumes of administration, the lumen of the cannula may act as a reservoir for the active agent containing composition and a plunger may be configured to move distally in the lumen of the cannula to provide a delivery force on the material for administration.

In some embodiments, the distal end of the cannulation device consists of an exposed needle containing at least the distal portion of the flexible cannula. The deployment of the cannula is actuated simultaneous with or after insertion of the needle into the tissues overlying the desired target tissue space. In one embodiment, the cannula deployment is performed by manual advancement of the cannula by a mechanism on the device coupled to the proximal portion of the cannula. In another embodiment, the cannula deployment is performed by actuation of a force element coupled to the proximal portion of the cannula. The speed and extent of cannula deployment may be controlled by the use of the advancement mechanism and actuation to allow careful progressive deployment. The use of an illuminated cannula provides guidance during progressive deployment of the cannula by the user.

In some embodiments, the distal end of the cannulation device consists of a distal element encompassing the distal end of the needle. The distal element functions as a tissue interface with a distal seal secured to the distal end of the cannulation device thereby sealing the needle lumen during application of the deployment force. The distal seal is penetrable by the distal tip of the needle by the application of pressure on the tissue surface with the distal end of the cannulation device and the penetrated distal element becomes slidable on the needle to allow advancement of the needle into tissue. Penetration of the distal seal opens a path for delivery of the cannula from the distal end of the needle. The cannulation device with a force element is activated prior to or simultaneous with penetration of the distal seal by the needle and advancement of the needle tip into tissues. The resulting self-actuating deployment mechanism ensures opening of the delivery path for the cannula immediately when the needle is placed in tissue, regardless of the orientation and speed of needle insertion. The self-actuation mechanism enables simple one-handed operation of the cannulation device to administer the cannula to the suprachoroidal space or supraciliary space of an eye.

In one embodiment, the distal element comprises a tissue interface and distal seal mounted on a tubular distal housing. The tubular distal housing is fitted to the exterior of the needle and may be sealed to the surface of the needle at some point along its length. In one embodiment, the housing may be sealed by means of an elastomeric element which is compressed between the housing and the needle. The elastomeric element may therefore be annular. In one embodiment, the elastomeric element may be compressed between the housing and the body of the device. The elastomeric element may reside at or near the proximal end of the housing. In one embodiment, the elastomeric element serves as a seal between the housing and the needle. In one embodiment, the elastomeric element serves as a frictional element or component which limits the housing travel in the proximal direction to thereby apply a force against the tissue surface by the tissue interface as the needle penetrates the tissues. In some embodiments, the distal element comprises a tissue interface and a distal seal and is slidably attached to the exterior of the needle without a distal housing. The distal element, which comprises a tissue interface with a distal seal, or a tissue interface with a distal seal and an attached housing, is attached to the distal tip of the needle but is not freely movable or slidable proximally from the end of the needle due to the distal seal. After the cannulation device is primed or activated for use, the cannula is under a deployment force from the force element but cannot move through the distal seal. The tissue interface is placed on the surface of the eye and the device is manually advanced, thereby forcing the needle through the distal seal and then through the external surface of the eye into underlying tissues. The distal element, after penetration of the distal seal, becomes proximally slidable from the end of the needle to retain the tissue interface on or near the surface of the eye during advancement of the needle into tissue. When the distal tip of the needle penetrates through the distal seal, the source of force immediately allows for deployment of the cannula from the needle tip and into the tissue space.

In one embodiment the tissue interface and distal seal is secured to a housing disposed about the needle. The housing may be comprised of a cylindrical element which is secured to the distal end of the body of the device at the proximal end of the housing. The housing may contain collapsible, distortable or deformable elements which allow the distal end of the housing to retract slidably along the needle, which in turn allows the needle tip to penetrate the distal seal. In some embodiments the distal element is secured to the distal tip of the needle through other means.

In one embodiment, the cannulation device comprises an elongated barrel with a hollow needle at the distal end, a cannula to be deployed residing at least partially in the needle lumen and a force element such as a spring or pressurized gas source mechanically coupled to the cannula to deploy the cannula. The deployment of the cannula may be actuated either manually by activating the force element or by action of the needle penetration into tissues to place the cannula in a tissue space when the distal tip of the device reaches the space.

In one embodiment, operation of the device mechanism opens the path for the cannula to deploy from the tip of the needle immediately upon penetration of the needle through a distal seal which occurs just prior to the entry of the needle into the target tissue. Since the cannula is under a deployment force prior to or simultaneous with penetration of the distal seal by the needle tip, the deployment is triggered solely by placement and subsequent advancement of the needle through the tissue interface. This allows precise and automatic control of the timing of the deployment action solely due to the needle tip entering the target tissue. The resultant self-actuated mechanism obviates the need for a separate control mechanism, for example a valve or trigger on the body of the cannulation device, and hence allows for deployment of the cannula without the need for special positioning of the fingers or the use of a second hand. The cannulation device thereby enables cannulation to be performed with a single hand, allowing the other hand of the physician to stabilize the eye or perform other actions to facilitate the procedure using the device. The self-actuating cannulation mechanism also eliminates the need for the user to determine when to begin deployment which is especially useful when the target tissue space is difficult to locate due to small target size, lack of visualization and anatomic variability such as the suprachoroidal space or supraciliary space.

The cannulation device allows precise control of the position of the needle by the user during use. The needle is fixed to the body of the device to allow direct control of the distal tip of the needle when the device is held. In embodiments in which the deployment force is provided by the force element, the cannula does not have to be held or advanced by the hand holding the device, allowing the device to be held and used in a natural, highly controllable position such as with a writing instrument or scalpel. Generally, the needle is arranged parallel to the elongated body or barrel of the device.

Once the needle is inserted into the eye, the cannula cannot extend or deploy from the distal tip of the needle until a space to accept the cannula is reached by the distal end of the needle. Scleral tissue in particular is very resilient and effectively seals the needle tip during passage of the needle tip to the suprachoroidal or supraciliary space, hence the unique properties of the sclera do not allow for the cannula to enter the sclera. Once an underlying space such as the suprachoroidal space or the supraciliary space is reached by the needle tip, the cannula is able to advance out of the needle and be deployed in the space. By this mechanism the cannula is directed to a location that can accept the cannula at the distal tip of the needle. Subsequent to the deployment of the cannula, a material for administration such as an active agent containing composition may be delivered through the lumen of the cannula to the eye. In one embodiment, the cannula is coupled to a force element for deployment. The distal tip of the needle is advanced into the surface of an eye and when the bevel of the needle is within the eye, the force element is activated to place a deployment force on the cannula. The needle is advanced further until the suprachoroidal or supraciliary space is reached by the needle tip sufficient for the cannula to self-deploy into the space.

The flexible cannula of the cannulation device is designed with the appropriate mechanical properties with suitable flexural modulus to allow the cannula to bend to advance into the suprachoroidal space or supraciliary space and with a suitable axial compressive stiffness to allow advancement of the cannula into the space by the deployment mechanism acting on a proximal segment of the cannula. The mechanical properties can be suitably tailored by the selection of the cannula material and the cannula dimensions. In addition, the cannula may have features to tailor the mechanical properties. A stiffening element such as a wire may be placed in the lumen or wall of the cannula to increase axial buckling strength. The distal tip of the cannula may also be reinforced, for example with a coil or coating to tailor both the buckling strength and flexibility of the distal portion of the cannula. The coil can be fabricated from metal or high modulus polymers and placed on the outer surface of the cannula, the inner surface of the cannula or within the wall of the cannula. In one embodiment, the distal portion of the cannula and the cannula tip is formed of a softer or more flexible material than the proximal portion of the cannula to form a soft tip configuration. A distal portion of 1 mm to 3 mm length of a softer material coupled to a stiffer proximal portion of the cannula allows deployment through the needle with the soft distal tip minimizing tissue penetration and trauma during deployment into the suprachoroidal or supraciliary spaces. The cannula may be fabricated from polymers such as polyether block amide (PEBA), polyamide, perfluoroalkoxy polymer, fluorinated ethylenepropylenepolymer, ethylenetetrafluoroethylene copolymer, ethylene chlorotrifluoroethylene copolymer polystyrene, polytetrafluoroethylene, polyvinylidene, polyethylene, polypropylene, polyethylene-propylene block copolymers, polyurethane, polyethylene terephthalate, polydimethylsiloxane, polysiloxane copolymers, polyvinylchloride, polyetherimide and polyimide. For some applications, the cannula may be fabricated from a flexible metal such as a nickel titanium super elastic alloy (Nitinol).

With an appropriate needle length and orientation, the device may be used to deploy a cannula and deliver materials for administration into the sub-conjunctival space, suprachoroidal space, supraciliary space and sub-retinal space, sub-Tenon's space, the vitreous cavity or the anterior chamber.

The needle comprises a stiff material, with a diameter to allow the cannula to pass through the lumen of the needle, typically in the range of 20 gauge to 40 gauge, for example, less than 0.9 mm (0.04 inches) outer diameter and 0.6 mm (0.02 inches) inner diameter), where the length of the needle is suitable to reach the intended tissue space. The needle is fixed to the body or barrel of the device and generally does not slide or move in relation to the body to provide precise control of needle depth during penetration of tissues.

The distal tip of the needle may be beveled or sharpened to aid penetration. The bevel angle may be designed to facilitate entry into a specific target. For example, a short bevel of 18 degree bevel angle may be used to cannulate into narrower spaces such as the subconjunctival or sub-Tenon's space. A medium bevel needle of 15 degree bevel angle may be used to cannulate into spaces such as the suprachoroidal or supraciliary space. Longer bevels, such as a 12 degree bevel angle may be used to cannulate into the anterior or posterior chambers.

In one embodiment, the device incorporates a distal element and a distal seal with a complementary bevel in a lumen of the distal element to provide close apposition of the distal seal to the needle bevel. The bevel of the needle is in alignment with the bevel in a lumen of the distal element. The most distal portion of the distal element may be flat or beveled to aid orientation of the needle during tissue penetration to aid reaching certain tissue spaces. For example, a beveled tissue contacting surface of the distal element may aid targeting of cannulation into the tissue targets with less depth such as the subconjunctival space, sub-Tenon's space and in some regions of the suprachoroidal space. The angle of the tissue contacting surface of the distal element may range from 90 degrees from the axis of the distal element for perpendicular insertion, to 15 degrees from the axis. The device may incorporate a guide at the distal tip to aid angulated insertion of the needle into the eye at a selected angle. The guide may consist of angled struts extending from the distal end of the device or an angled plate to contact the eye prior to needle insertion. The guide may also consist of struts extending from the body to provide a reference for estimating the angle of needle insertion.

In some applications of the invention, it may be desired for the distal tip of the needle to direct the cannula at an angle from the long axis of the needle. Such a design reduces force of the cannula on the underlying tissues of the target tissue space such as the ciliary body or choroid and may also be used to direct the cannula in a desired direction such as toward the posterior region of the suprachoroidal space near the macular region of the retina. The distal tip of the needle may be curved in the range of 5 to 60 degrees to direct the cannula. The distal tip of the needle may also have an inner deflecting element in the lumen of the needle in the region of the bevel of the needle. The inner deflecting element may be a protrusion, a sloped surface or a ramp to direct the cannula away from the long axis of the needle. The inner deflecting element may be located along the entire length of the needle bevel or in a discrete location from the proximal end of the bevel. In one embodiment, the inner deflecting element is located at a position from the distal end of the bevel, 20% to 80% of the length of the needle bevel, 25% to 75% of the length of the needle bevel or 30% to 60% of the length of the needle bevel. The body of the device may incorporate a label or indicator to provide the user with the orientation to the direction of the cannulation, for instance a notation of the orientation of the needle bevel or the direction in which a deflection element will deflect the cannula.

The needle may be constructed from a metal, ceramic, high modulus polymer or glass. The length of the needle in tissue is selected to match the target location for the cannulation and the variation in target location due to anatomical variability. The effective full length of the needle is the length of the needle that may be advanced into tissues. In embodiments of the device with a distal element surrounding the needle, the effective full length of the needle is the length of the needle distal tip to the distal surface of the tissue interface, when the distal element has achieved full proximal travel. The distal element moves slidably on the needle during needle advancement into tissue, allowing for progressive increase in the length of needle protruding through the distal element during advancement into tissue.

In some embodiments, the cannula is deployed once the needle reaches the appropriate location which may be less than the effective full length of the needle. The release of force and resultant time for deployment occurs quickly, in approximately 0.1 to 3 seconds depending on the deployed length of the cannula and the speed of manual advancement by the user.

In embodiments with a force element to deploy the cannula, the deployment speed may be controlled by the amount of force applied by the force element. The time for deployment, approximately 0.1 to 3 seconds, may also be controlled by a damping or frictional mechanism coupled to advancement of the cannula to limit the speed of cannula advancement or deployment. The damping or frictional element may be configured with the amount of damping or friction coupled to the extent of deployment to balance the non-linear force delivery of the force element, such as a spring. In one embodiment, a friction wheel is engaged with a plunger shaft coupled to the proximal end of the cannula. During deployment, the friction wheel slows the plunger speed dependent on the amount of friction. The friction may be tailored along the deployment distance by increasing contact with the plunger shaft or by a varied coefficient of friction such as the amount of texture along the length of the shaft. Typically, the friction is configured to be greater during the initial deployment when the deployment force from a compressed force is the greatest, and the friction is configured to decrease during the movement of the plunger toward full deployment length. The deployment mechanism may incorporate features to communicate to the user with both visible and tactile feedback upon deployment of the cannula from the needle to indicate that there is no need for additional advancement of the needle. The controlled speed deployment event gives the user sufficient time to halt needle advancement, resulting in an effective variable needle length to accommodate patient to patient differences in tissue thickness. Embodiments of the device with an effective variable needle length and self-actuation of deployment are useful for cannulation into spaces that are not normally open, such as the subconjunctival space, sub-Tenon's space, suprachoroidal space and supraciliary space. For the subconjunctival space and sub-Tenon's space the needle effective full length is in the range of 0.35 mm (0.01 inches) to 2 mm (0.08 inches) depending on the angle of needle insertion. For the suprachoroidal space and supraciliary space, the needle effective full length is in the range of 1 mm (0.04 inches) to 5 mm (0.16 inches) depending on the angle of insertion. For the vitreous cavity, the needle effective full length is in the range of 5 to 15 mm. The effective full needle length may, for example, be 0.3 mm (0.011 inches) to 3 mm (0.12 inches), 0.35 (0.014 inches) to 2 mm (0.08 inches), 1 mm (0.04 inches) to 4 mm (0.16 inches), 10 mm (0.39 inches) to 15 mm (0.59 inches).

In one embodiment, the distal element applies a distally directed sealing force against the tissue surface to maintain a seal on the surface of the eye. The sealing force is designed to be sufficient to seal potential flow of the material for administration from the needle track during administration of the delivery material. The sealing force is minimized to prevent compression of the tissues of a normally closed space or nearly closed space such as the suprachoroidal or supraciliary space at the site of needle penetration that would prevent cannulation into the space or increasing the intraocular pressure that would restrict movement of the material for administration into the normally closed or nearly closed space. In one embodiment, the distal element maintains contact with the tissue surface but does not apply a distally directed sealing force against the tissue surface to maintain a seal on the surface of the eye. In one embodiment, the distal element contacts the surface of the eye during penetration of the distal seal of the distal element by the distal tip of the needle but does not maintain contact with the surface of the eye after needle penetration through the distal seal and into ocular tissue.

In embodiments with a tissue interface and distal seal, the tissue interface and distal seal may comprise a soft polymer, rubber or other material that allows needle penetration without coring of the seal material. The tissue interface and distal seal material may be selected to provide compliance to the surface of the eye during insertion of the needle into ocular tissue and also to seal the deployment pathway from the needle until the needle is advanced through the distal seal. Once the needle penetrates the distal seal, the needle is advanced through the outer ocular tissues to reach the desired cannulation site. The tissue interface and distal seal remain on the surface of the eye. The distal seal is sufficiently resilient to prevent rupture by the cannula under deployment force prior to advancement of the needle through the distal seal. The portion of the distal seal in the path of the needle is also sufficiently thin to allow penetration by the needle without undue application of force. The distal seal is typically in the range of 250 microns (0.01 inches) to 1500 microns (0.06 inches) in thickness in the region that is penetrated by the needle.

In one embodiment, a sealing force is provided by a compressible or collapsible element between the body of the device and the proximal end of the distal element or distal housing. In one embodiment, the tissue interface provides a sealing force by compression of the tissue interface or elastically compressible elements in the distal element. In one embodiment, the distal element is configured to allow an elastic reduction in length during needle advancement to apply a sealing force. In one embodiment, a friction element disposed in or about the distal element increases the force required to move the distal element proximally thereby promoting contact of the tissue interface with the surface of the eye and maintaining a seal against the eye surface during needle advancement. The friction of the distal element against the needle may be tailored in relation to the proximal movement of the distal element during needle advancement. An increase in friction may be obtained by increased contact or surface texture between the distal element and the external surface of the needle or through a decrease in the durometer of the distal element in order to tailor the amount of force applied by the tissue interface during proximal travel of the interface along the needle length. The friction may be varied along the path of travel of the distal element along the needle. For example, low friction may be provided during the initial path of travel of the distal element to promote insertion of the needle into ocular tissues, the friction may be increased after a length of the needle corresponding to the length of the needle bevel is inserted into ocular tissue. The length of travel of the distal element under the influence of the region of high friction is in the range of 0.3 mm (0.01 inches) to 2 mm (0.08 inches).

In one embodiment, the device incorporates a distal element with a distal seal that is attached to the body of the device by one or more collapsible elements. The collapsible element is configured to not allow an increase in length to prevent the distal seal from being displaced from the tip of the needle when a deployment force is applied to the cannula prior to needle penetration of the distal seal. The collapsible element allows a reduction in length, thereby allowing proximal travel of the distal element during advancement of the needle into tissues. In one embodiment, the collapsible element comprises one or more elongated struts that may deform, bend or fold away from the needle during proximal travel of the distal element. In one embodiment, the collapsible element comprises a section of tubing concentric to the needle that has been cut to form openings along the axial length of the tubing to form collapsible struts. The shape and configuration of the collapsible struts may be tailored to provide a desired force-displacement characteristic of the collapsible element. The force versus displacement may be linear or non-linear. In one embodiment the collapsible element provides a force which transitions from an increasing spring like force per unit displacement to a constant force independent of displacement to keep the tissue interface and distal seal in contact to the eye surface without undue application of force with further needle advancement into the eye. In another embodiment the collapsible element provides a very low force per unit displacement to promote needle entry into tissue, with an increased force after insertion of the needle bevel into tissue. Application of force above 80 grams-force (0.18 pounds-force) to 100 grams-force (0.22 pounds-force) may limit the ability of the cannula to enter a closed space such as the suprachoroidal or supraciliary space. In one embodiment, the tissue interface applies a force in the range of 40 grams-force (0.09 pounds-force) to 80 grams-force (0.18 pounds-force). The transition of the amount of force is designed to occur after a length of the needle bevel is inserted into ocular tissue, corresponding to a compression or collapse of the collapsible element of 0.3 mm (0.01 inches) to 2 mm (0.08 inches). In one embodiment the collapsible element provides for contact of the tissue interface to the surface of the eye during initial insertion of the needle into ocular tissue, but collapses to provide little or no resistance to proximal movement of the distal element along the needle after the bevel of the needle is fully inserted into tissue. The collapsible element may be assembled from components in a tube-like configuration or alternatively cut from a segment of tubing such as a laser machined nickel titanium alloy (e.g. Nitinol) tube or a polyimide tube. Suitable materials for a distal collapsible element include, but are not limited to, stainless steel, spring temper steel, super-elastic nickel titanium alloys, cobalt chrome alloys, oil-tempered chrome silicon, polyimide, and polyetherimide. The collapsible element may be disposed between the elongate body and the distal element, such as between the barrel and the housing of the distal element (if present). The collapsible element may be fixed to the body of the device and to the distal element such that the distal element is proximally slidable on the needle but will not travel distally from its initial position.

In some embodiments of the device that incorporates a distal seal and tissue interface, the tissue interface provides a sealing function. The sealing force provided by the tissue interface is within a range to provide sealing of the needle tract, but less than the force that would close the tissue space to impede movement of the cannula into the suprachoroidal or supraciliary space. A tissue interface with a tissue contacting surface area in the range of 0.45 mm$^2$ (0.0007 in$^2$) to 5.07 mm$^2$ (0.008 in$^2$) is suitable for sealing of the needle tract. Suitable materials for the tissue interface and distal seal include, but are not limited to, natural rubbers, silicone rubbers and thermoplastic elastomers such as polyurethanes. The stiffness of the rubber or elastomer may be selected to provide the appropriate combination of conformance to the tissue surface and sealing of the lumen of the distal end of the needle. The selection of the material of the tissue interface may also minimize the sealing force that might impede movement of the cannula into the tissue space. The rubber or elastomer must also be capable of penetration or deformation by the distal tip of the needle to trigger release of the cannula. Rubbers or elastomers with a Shore A durometer of 10 to 70, 10 to 50 or 10 to 30 are suitable for use as the sealing element. Suitable materials for a distal housing include, but are not limited to, polypropylene, polyethylene, polycarbonate, polysulfone, polyetheretherketone, acrylonitrile butadiene styrene, polystyrene, polyamide, and polyurethanes.

In one embodiment, the body or barrel of the device contains a reservoir and provides an external surface for holding the device during use. The reservoir may comprise a tubular cylinder attached on its distal end to the proximal end of the needle, with a plunger slidably disposed in the lumen of the tubular body. The reservoir may also provide for insertion of a cartridge containing the material for administration where a plunger of the device moves a slidable seal in the proximal end of the cartridge to deliver the material. The body of the device may be fabricated from a variety of thermoplastic materials suitable for medical use such as polypropylene, polyamide, polycarbonate, polysulfone, polyethylene, cyclic polyolefins, polystyrene and polymethylmethacrylate. The body may incorporate external features such as textures or finger indentations to allow a user to more ergonomically grip and use the device. The body may incorporate index or measurement markings to provide an indication of the amount of material being delivered. The body may incorporate transparent materials or a section of transparent material to allow the visualization of the material for administration in the reservoir or movement of the plunger to visually indicate the delivery event. The plunger may have markings to aid visualization of reservoir loading and release of the material for administration. The body of the device may incorporate a label or indicator to provide the user with the orientation to the direction of the cannulation, for instance a notation of the orientation of the needle bevel or the direction in which a deflection element will deflect the distal tip of the cannula during deployment.

In some embodiments of the invention, the device comprises a means for providing a deployment force to the cannula. In some embodiments of the invention, the device comprises a means for providing a force to deliver the material for administration from a reservoir within the device. The means for providing a deployment force to the cannula may be actuated manually by any acceptable actuation apparatus such as a button or lever incorporated into the device or alternatively by a trigger mechanism on the distal end of the device upon tissue penetration by the needle. The means for providing a force to deliver the material for administration from a reservoir within the device may be actuated manually by any acceptable actuation apparatus such as a button or lever incorporated into the device or alternatively by a trigger mechanism coupled to the deployment of the cannula. The means as described herein could be, for example, a compressible reservoir or levers that can be "squeezed" or compressed by a user (directly or indirectly) to effect deployment of the cannula or delivery of the material for administration. Alternatively, in one embodiment, the means is a mechanism with a biasing means or force element (such as a compression spring or a pressurized gas).

The device may be disposable and/or for single use. Alternatively, the device may be reusable.

In some embodiments, the device incorporates a distal seal where the distal seal acts to prevent escape of the cannula from the needle when the device is primed by activation of the force element prior to contact of the needle with the eye. This can be achieved by a seal between the needle lumen and the outside of the device. This seal may be achieved by the seal being in direct contact with the needle tip or may be achieved by using a distal element housing that is suitably sized to provide a seal around the needle shaft when placed over the needle tip. For example, the outer diameter of the needle may be complimentary to the inner diameter of the housing to provide a seal. In embodiments of the invention, the seal may only block enough of the needle lumen so as to prevent the cannula from being deployed until the seal is moved proximally, thereby fully exposing the opening of the lumen. In such embodiments the distal seal is a partial seal and not covering the entirety of the needle lumen at the distal end of the needle. Hence the seal may comprise deformable protrusions that extend into the lumen at the distal end of the needle or that extend into a distal projection of the lumen from the distal end that would be sufficient to prevent deployment of the cannula. Needle penetration through such embodiments of the distal seal may be achieved by deformation of the protrusions by the distal tip of the needle as it passes past the protrusions. The embodiments of the invention describing needle penetration of the distal seal are also applicable with the use of a partial seal formed by protrusions that extend toward or across the lumen at the distal end of the needle.

Generally speaking, and as described above, some embodiments of the device provide self-actuating deployment of the cannula such that once the needle reaches the desired site of delivery in the eye (such as the suprachoroidal space or supraciliary space), the cannula is automatically deployed. The self-actuation may be performed by a device with a distal seal to prevent cannula deployment in conjunction with a deployment force that is actuated prior to or simultaneous with insertion of the needle tip into tissues. The self-actuation may be performed by a device with a trigger on the distal end that activates the deployment force simultaneous with or immediately after insertion of the needle tip into tissues. In this way, the device can be operated with one hand. The effective needle length and angle of needle insertion can be suitably designed to target specific cannulation sites at corresponding depths in the eye. In some embodiments, the device may comprise a retaining means to retain the distal element on the needle once the device is primed.

In embodiments of the device with a bare needle at the distal tip, without a distal element or distal seal, the maximum needle depth is the length of the needle from the needle distal tip to the distal end of the device body or stops placed between the needle and the body. In embodiments of the device with a distal element and distal seal the distance between the proximal end of the distal element and distal end of the elongate body or barrel (and design of any compressible or collapsible element that may be present) can be arranged to determine the maximum depth of needle penetration. The distance between the proximal end of the distal element and distal end of the elongate body or barrel, accounting for any distance between the needle tip and the distal seal/tissue interface and/or the use of any compressible or collapsible element may be equal to the maximum depth of needle penetration. Thus, the position and sizes of the distal element, needle, and distance between the needle tip and distal seal/tissue interface (if any) can be configured to determine a maximum needle penetration depth. The skilled person could design the device accordingly based on the present disclosure.

In this way the device may comprise a means for determining a maximum needle penetration depth to control the maximum cannulation depth into the eye. The needle may comprise a separate element that halts advancement of the needle such as an annular ridge, stop or clamp. In some embodiments, this element to prevent further advancement of the needle during operation may be moveable such that the maximum needle penetration depth can be determined by the user. In such an embodiment, the needle may comprise markings to allow the user to select an appropriate maximum penetration depth. In another embodiment, the depth of needle penetration may be determined by a compressible element, for example the compressible element only allowing the desired needle advancement by way of increasing rigidity as the element is compressed, or by other mechanical means. The present invention therefore provides devices having fixed maximum needle penetration depths suitable for targeting the tissue of interest. Suitable designs to achieve a fixed maximum needle penetration depth would be apparent to the skilled person based on this disclosure. Of course, the maximum depth of needle penetration can be within certain tolerances. Maximum needle penetration depth is also referred to herein as effective needle length.

In one embodiment, the material for administration such as an active agent containing composition is preloaded in the cannulation device, whereby the device serves as the storage container for the material for administration prior to use. In one embodiment, the preloaded device is sterilized for use after placement and sealing of the material for administration in the cannulation device. The sterilization may be accomplished by established methods of sterilization such as heat or ionizing radiation. In one embodiment the material for administration is preloaded in the device as a dry material that is reconstituted with a liquid that is introduced into the device prior to use. The cannulation device may contain a port or connector in fluid communication with the device reservoir to facilitate reconstitution of the material for administration within the cannulation device. In another embodiment, the material for administration is contained in a reservoir such as a cartridge vial and is sterilized or prepared aseptically separate from the cannulation device. The cartridge vial and cannulation device are designed to allow insertion of the cartridge vial in the cannulation device by the user prior to use. In another embodiment, the material for administration is contained in a reservoir such as a cartridge vial which contains two reservoir compartments, one compartment for the lyophilized material for administration and one compartment for the reconstitution fluid. Prior to administration, the reconstitution fluid is transferred to the material compartment to reconstitute the lyophilized material.

One embodiment of the cannulation device is depicted in FIG. 1. The device comprises a hollow barrel 1, with a proximal barrel end cap 2. A plunger 3 slidably passes through the end cap. The plunger has a lumen 4, in which resides a flexible cannula tubular element 5. The flexible cannula 5 is fixed in place to the plunger 3. The distal tip of the flexible cannula has a rounded atraumatic tip 6. A plunger compression spring 7, provides a distally directed force on the plunger 3 and flexible cannula 5. A beveled needle 8 is attached and fixed to the distal end of the barrel 1 such that the needle 8 does not move in relation to the barrel 1 to provide direct control of the location of the needle tip when manipulating the position of the barrel 1. The flexible cannula 5 moves distally under the force of the plunger compression spring 7. The proximal end of the plunger 3 terminates in an interface such as a Luer fitting 9 to allow delivery of a material for administration through plunger lumen 4 and the flexible cannula 5.

Two embodiments of the distal end of the flexible cannula are depicted in FIGS. 2A, 2B, and 2C. In FIG. 2A, the flexible cannula 5 is shown deployed beyond the distal tip of the beveled needle 8, which is attached to the hollow barrel 10. In one embodiment shown in FIG. 2B the distal tip of the flexible cannula 5 is straight and in a second embodiment shown in FIG. 2C the distal tip of the flexible cannula 5 incorporates a curved tip 11. Both embodiments are shown with illumination 12 emanating from the distal tip of the flexible cannula 5.

One embodiment of the device is shown in FIG. 3. The device incorporates a main shaft 13 slidably disposed within a housing assembly 14. The main shaft incorporates a distal flexible cannula assembly 15, a coupler assembly 16, an internal fluid line 17 and a fiber optic 18. Proximally, the internal fluid line 17 connects via an external fluid line 36 to a female Luer connector 9 and the fiber optic terminates in an optical connector 19.

The housing assembly comprises a left and right side main housing elements 20 and 21, a proximal end cap 2 and a distal nose cone 22. A beveled tip hollow needle 8 is adhesively bonded into the lumen of the distal nose cone. The distal tip of the needle 8 may be configured with a hypodermic or lancet type multi-faceted geometry bevel or another bevel geometry suited to the application.

Figure 3A:
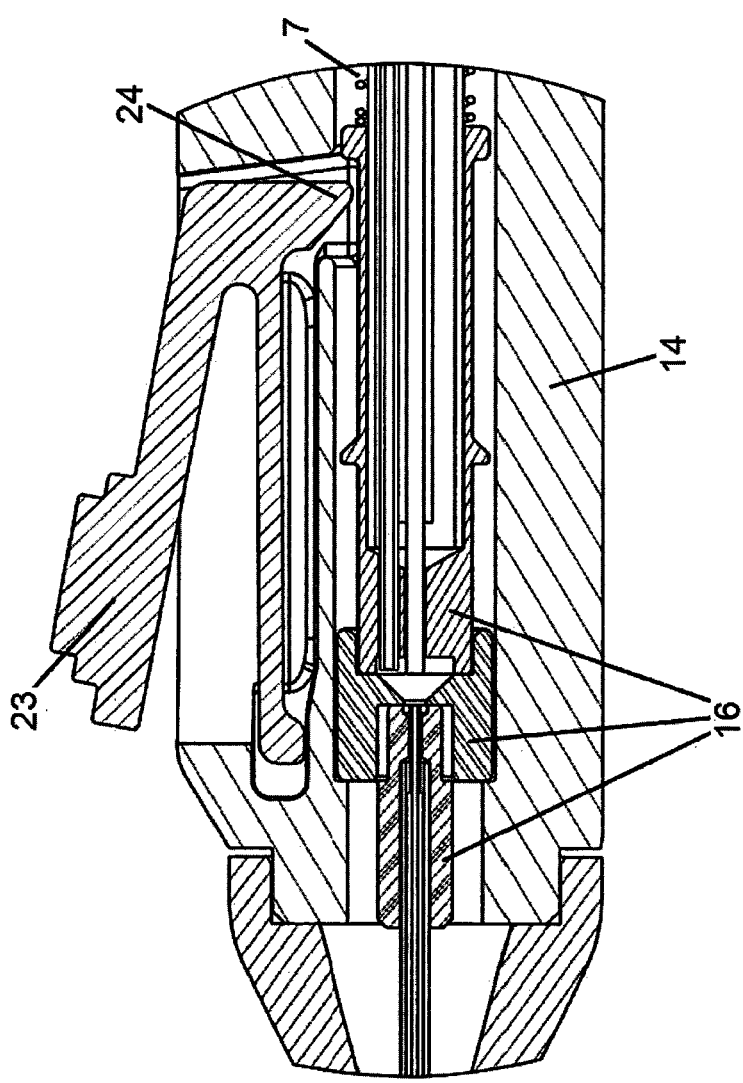
FIG. 3A depicts the magnified detail of the trigger mechanism of the device of FIG. 3.

The main shaft 13 is advanced by means of a main shaft compression spring 7 acting as a force element. The advancement is initiated by the actuation of a trigger 23 as shown in FIG. 3a. The trigger incorporates a lift-point 24 which engages with the coupler assembly 16 to hold the main shaft 13 in the retracted position prior to use. When the trigger 23 is actuated, the trigger lift-point 24 is translated upwards and the trigger lift point disengages from the coupler assembly 16 allowing the main shaft 13 to translate forward under the force of the main shaft compression spring 7. The trigger 23 can be fabricated from a rigid or semi-rigid material such as acrylonitrile butadiene styrene, high density polyethylene or polycarbonate. The trigger 23 can be machined, molded or 3D printed. The force required to actuate the trigger 23 is dependent on the material properties of the trigger and the thickness and length of the flexible portion of the trigger body. The thinner the material, the lower the force required to deflect the actuation trigger and therefore to actuate the device. The main shaft compression spring 7, can be fabricated from music wire, stainless steel wire, Elgiloy alloy or similar material. The main shaft compression spring 7 can range from 63.5 mm (2.5 inches) to 127 mm (5.0 inches) in length and the spring wire diameter can range from 0.23 mm (0.009 inches) to 0.51 mm (0.020 inches) and have a spring force in the range of 0.007 N/mm (0.04 lbs/in) to 0.044 N/mm (0.25 lbs/in) and preferably in the range of 0.011 N/mm (0.06 lbs/in) to 0.018 N/mm (0.10 lbs/in). The housing assembly 14 can be machined molded or 3D printed from plastics such as acrylonitrile butadiene styrene, glass filled acrylonitrile butadiene, styrene, polycarbonate, nylon, glass filled nylon, or metals such as stainless steel, titanium, aluminum or similar material.

A feature of the actuation trigger 23 is that when activated, it firstly forces the main shaft 13 to move proximally a small distance so as to break any stiction in the system prior to lifting the trigger lift point 24 and allowing the main shaft 13 to travel in the distal direction. The distal segment of the main shaft is comprised of a coupler assembly 16 and a flexible cannula assembly 15. When actuated, the flexible cannula assembly 15 advances distally outward through the lumen of beveled needle 8. The flexible cannula assembly 15 is sized to allow the flexible cannula to freely slide within the lumen of the needle 8. The beveled needle can range in size from 21 to 31 gauge.

Figure 3B:
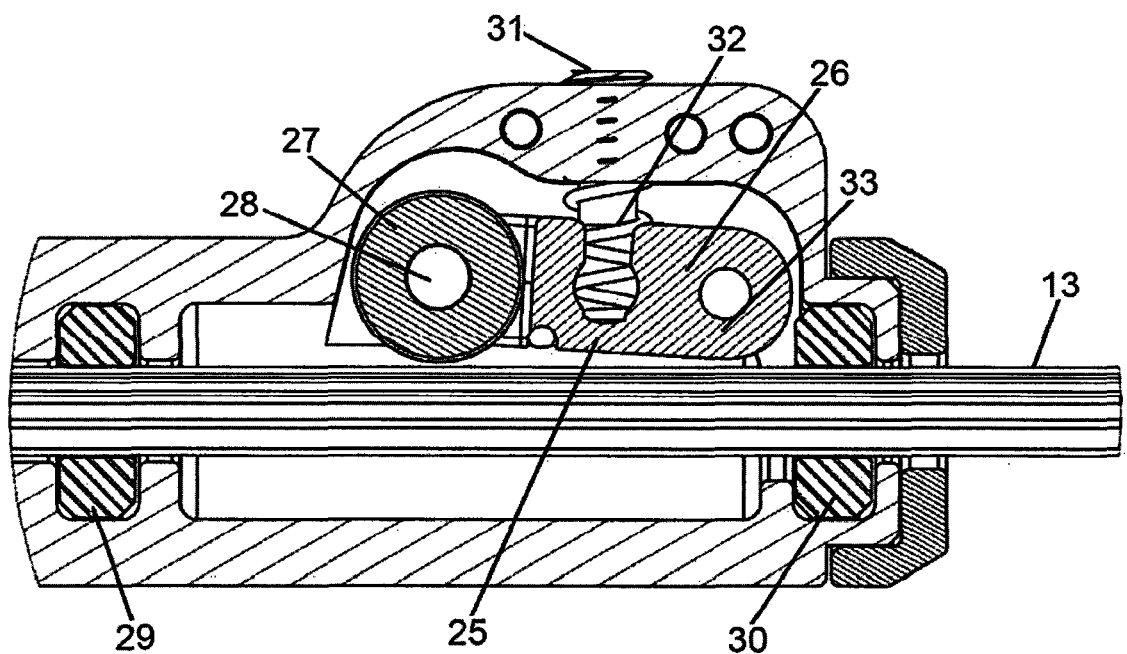
FIG. 3B depicts the magnified detail of the speed damper mechanism of the device of FIG. 3.

The translation speed of the main shaft 13 is controlled by an adjustable friction speed dampener assembly 25 as shown in FIG. 3b. The adjustable frictional speed dampener assembly 25 is comprised of a pivot arm 26, upon which is mounted a speed dampening wheel 27 by means of a wheel axle 28, a proximal bushing 29, a distal bushing 30, a speed control adjustment screw 31 and a speed control compression spring 32. The pivot arm 26 freely rotates on a pivot arm axle 33 mounted to interior of the housing 14. The speed control spring can be a torsion spring or a compression spring and acts to place compressional forces on the pivot arm 26. The speed control spring can be fabricated from music wire, stainless steel wire or similar material. The speed dampening wheel 27, can be made from a variety of elastomeric materials such as Buna N, silicone, Viton, EPDM or from rigid materials such as polycarbonate, nylon or ABS or similar materials. The speed dampening wheel axle 28 and the pivot arm axle 33 can be made from a smooth rigid material, such as stainless steel, titanium, copper, aluminum, or similar material. The pivot arm 26 can be molded, machined or printed from a rigid material such as polycarbonate, acrylonitrile butadiene styrene, Ultem, nylon, acetal, polysulfone or similar material. The pivot arm adjustment screw is threaded in the range of 1-5 threads per mm (24-120 threads per inch) so as to allow for fine adjustment of the main shaft advancement speed.

The advancement speed of the main shaft 13 is controlled by the force of the dampening wheel against the main shaft and the resultant friction on the bushings 29 and 30. The speed of advancement is controlled by the extent of the compression of the speed control compression spring 32 against the pivot arm 26, which in turn translates the force to the polymer wheel 27 which is in frictional contact with the main shaft 13. The speed control adjustment screw 31 is advanced or retracted to vary the compression of the spring. The main shaft 13 is slidably disposed within the proximal and distal bushings 29 and 30. The proximal and distal bushings 29 and 30 can be machined or molded and are ideally made from a low friction polymer material such as polytetrafluoroethylene, fluorinated ethylene propylene, polyethylene, ultra-high molecular weight polyethylene, Ultem, acrylonitrile butadiene styrene, or similar material. The proximal and distal bushings can alternatively be incorporated within the left and right side housing assembly portions of the assembly.

The tubular main shaft 13 is hollow and can be made from a rigid material such as stainless steel, titanium, aluminum, acrylonitrile butadiene styrene, polycarbonate, glass filled nylon or similar material and would ideally have a low friction, smooth outer surface. The lumen diameter of the main shaft 13 is sized to allow for the internal fluid line 17 and fiber optic cable 18 to be disposed within the lumen.

Figure 3C:
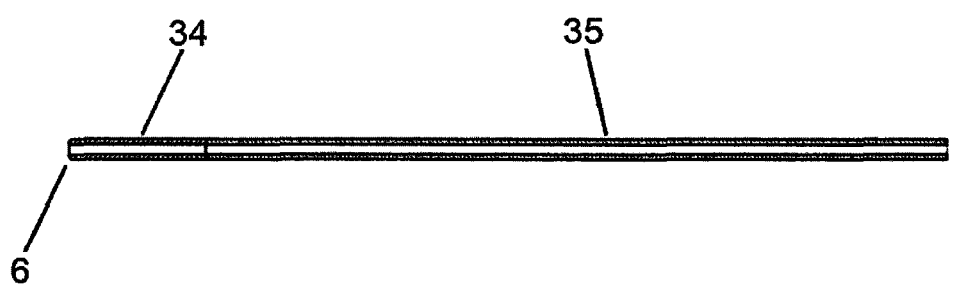
FIG. 3C depicts the magnified detail of the flexible cannula distal end of the device of FIG. 3.

The flexible cannula assembly 15, shown in FIG. 3c, comprises a distal cannula soft tip 34, a flexible cannula main body 35, and a flexible cannula proximal support 37.

The flexible cannula assembly is sized to slide freely through the lumen of the beveled needle 8. The distal soft tip 34 is comprised of a lower durometer polymer than the flexible cannula main body 35. The distal end of the soft tip is configured with an atraumatic tip 6 configured with a radiused, beveled or bulbous tip. The soft tip and the main shaft should ideally be fabricated from the same class of polymers. The soft tip is preferably attached to the main body by thermal means, however adhesive, ultrasonic or other means may be used to connect the distal tip to the main body. The main body and soft tip may be fabricated from elastomers such as polyurethane, polyurethane copolymers, polysiloxane, polysiloxane copolymers, polyether block amide or similar materials. The flexible cannula may be sized in the range of 0.18 mm (0.007 inches) to 0.51 mm (0.020 inches) outer diameter and 0.08 mm (0.003 inches) to 0.46 mm (0.018 inches) inner diameter.

The flexible cannula assembly 15 is supported by a thin tubular flexible cannula proximal support 37. The proximal support serves to prevent the cannula assembly from kinking within the device as the cannula is being advanced under the force of the main compression spring. The proximal support may be fabricated from materials such as stainless steel, titanium, polyimide, polytetrafluoroethylene, polycarbonate or similar materials. The flexible cannula proximal support 36 is sized to fit over the outside of the flexible cannula assembly 15 and within the lumen of the beveled needle 8.

Centrally aligned and in close proximity with the proximal end of the flexible cannula assembly 15 is a fiber optic cable 18. The fiber optic cable 18 transmits light from a light source (not shown), to the proximal end of the flexible cannula assembly 15, thereby causing the entire cannula to illuminate. The illuminated cannula allows the cannula to be viewed by the user through the scleral tissues, so as to locate and verify the position of the cannula during the procedure. The fiber optic cable 18 is fabricated from a plastic optical fiber for flexibility and the fiber diameter may be in the range of 0.25 mm (0.010 inches) to 2 mm (0.08 inches). The gap or space between the distal end of the fiber optic cable 18 and the proximal end of the flexible cannula assembly 15 may be configured to attenuate the light intensity transmitted to flexible cannula assembly 15 and the light output of the cannula. Alternatively, an attenuator may be placed between the distal end of the fiber optic cable 18 and the proximal end of the flexible cannula assembly 15 to regulate the light output of the cannula. The device is typically configured to provide a light output of 100 to 700 µW.

Disposed within the main shaft 13 and offset from the fiber optic cable 18, is the internal fluid line 17. The internal fluid line 17 allows fluids and flowable semi-solid materials to enter the coupler assembly 16 and into the lumen of the flexible cannula assembly 15. The internal fluid line 17 passes though the main shaft 13 and is connected proximally to the external fluid line 36. The proximal end of the external fluid line 36 terminates in a female Luer fitting 9 for connection to an external device such as a syringe for delivery of a therapeutic agent. The internal fluid line 17 is comprised of rigid tubing in the range of 0.25 mm (0.010 inches) to 1.5 mm (0.060 inches) outer diameter and 0.13 mm (0.005 inches) to 1.4 mm (0.055 inches) inner diameter and may be fabricated from materials such as stainless steel, titanium, polyimide, polytetrafluoroethylene, polycarbonate or similar materials. The external fluid line 36 is comprised of flexible tubing in the range of 0.5 mm (0.020 inches) to 3.2 mm (0.125 inches) outer diameter and 0.25 mm (0.010 inches) to 2.54 mm (0.10 inches) inner diameter and may be fabricated from elastomers such as polyurethane, polyurethane copolymers, polysiloxane, polysiloxane copolymers, polyether block amide, polyvinylchloride or similar materials.

The device may be used to deliver very small volumes of therapeutic agents, in the range of 10 to 250 microliters. In some embodiments, the device may be used to deliver high value therapeutics where the amount to be used in a procedure must be carefully controlled and loss minimized. In order to deliver small volumes, the dead space within the fluid pathway of the device must be controlled and minimized. The device may be configured with a dead volume of less than 75 microliters, less than 50 microliters, or less than 25 microliters.

One embodiment of the cannulation device is depicted in FIG. 4. The device comprises a hollow barrel 1, with a proximal barrel end cap 2. A plunger 3 slidably passes through the end cap. The plunger has a lumen 4, through which passes a flexible cannula tubular element 5. The flexible cannula 5 is fixed in place to the plunger 3. The distal tip of the flexible cannula has a rounded atraumatic tip 6. A plunger compression spring 7, provides a distally directed force on the plunger 3 and flexible cannula 5. A beveled needle 8 is attached and fixed to the distal end of the hollow barrel 1 such that the needle 8 does not move in relation to the barrel 1 to provide direct control of the location of the needle tip when manipulating the position of the barrel 1.

The flexible cannula 5 moves distally under the force of the plunger compression spring 7 when the tissue interface and distal seal 38 is opened by the distal tip of the needle 8. The tissue interface and distal seal 38 is attached to the distal end of a collapsible element 39. The collapsible element 39 is attached to the distal end of the barrel 37 and provides a distally directed force on the tissue interface and distal seal 38 thereby pressing the tissue interface and distal seal 38 onto the tissue surface. The proximal end of the flexible cannula 5 terminates in an interface such as a Luer fitting 9 to allow delivery of a material for administration through the flexible cannula 5.

One embodiment of the cannulation device is depicted in FIG. 5. The device is configured as a hollow barrel 13, with a hollow body 40 residing slidably within the hollow barrel and containing a reservoir 41 for the material to be administered. The distal end of the reservoir body 40 is connected to a flexible cannula tubular element 5. A tubular reservoir plunger 42 resides slidably inside the reservoir and a connector such as a Luer fitting 9 is attached at the proximal end of the reservoir plunger to allow filling of the reservoir. The connector incorporates a one-way valve 43 to prevent reflux of the material to be administered after filling of the reservoir. A reservoir plunger compression spring 44 provides the force to expel the material to be administered.

The reservoir body 40 acts as a plunger within the hollow barrel for the deployment of the flexible tubular cannula 5. A reservoir compression spring 44 resides over the hollow body 40. The reservoir compression spring 44 provides the force to deploy the flexible cannula 5.

A beveled needle 8, is attached and fixed to the distal end of the barrel 13, such that the needle 8 does not move in relation to the barrel 13 to provide direct control of the location of the needle tip when manipulating the position of the barrel 13. The distal end of the flexible cannula assembly 15 is configured within the lumen of the beveled needle 8. The flexible cannula 5 moves distally under the force of the reservoir compression spring 44 when the tissue interface and distal seal 38 is opened by the distal tip of the needle 8.

Figure 7:
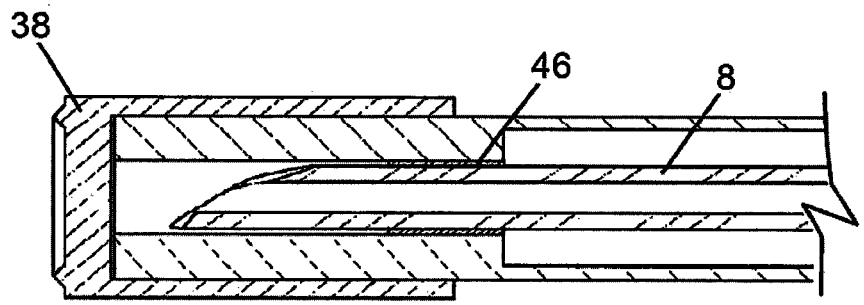
FIG. 7 depicts the magnified detail of one embodiment of a distal tip of a cannulation device with a collapsible element.
Figure 8:
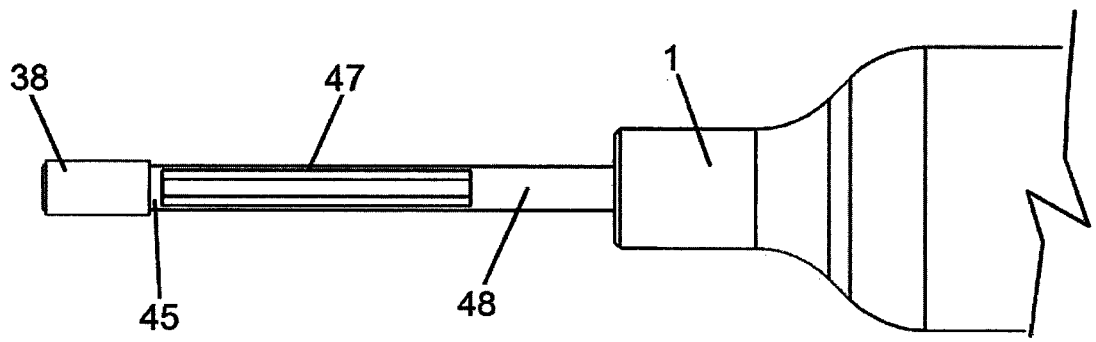
FIG. 8 depicts one embodiment of a distal tip of a cannulation device in an uncollapsed state.

In one embodiment, the distal tip of the device is comprised of collapsible elements. Referring to the device depicted in FIG. 6 and the magnified device distal tip detail in FIG. 7, the distal tip is comprised of a distal segment, a central collapsible segment and a proximal segment. The tissue interface and distal seal 38 is disposed about a distal tubular shaft 45. The inner lumen of the distal tubular shaft 45 contains an internal seal 46 which seals the space between the tubular distal shaft 45 and the beveled needle 8. The central segment is comprised one or more segments 47 which function as collapsible elements. The collapsible elements 47 are attached or integral to the distal tubular shaft 45 and proximal tubular shaft 48. The proximal tubular shaft 48 is connected to the barrel 1 of the device providing an anchor point for the collapsible element and preventing distal movement of the tissue interface and distal seal 38. FIG. 8 shows the distal segment of the device in an uncollapsed state. The tissue interface and distal seal 38 and the distal tubular shaft 45 are disposed at the end of the collapsible elements 47. The proximal tubular shaft 48 is anchored to the barrel 1.

Figure 9:
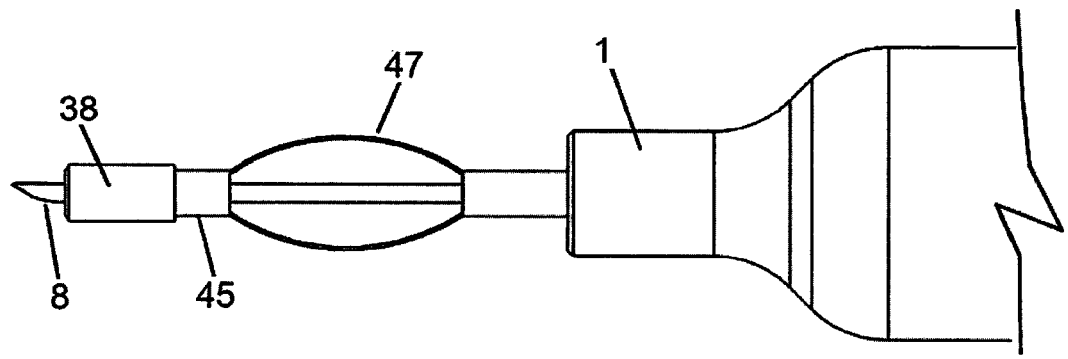
FIG. 9 depicts one embodiment of a cannulation device in a collapsed state.

FIG. 9 shows the distal segment of the device in a collapsed state. The force of advancing the device into the tissue causes the collapsible elements 47 to deform, allowing the distal tubular shaft 45 and tissue interface and distal seal 38 to slide proximally along the needle 8 toward the distal end of the barrel 1. The distal tip of the needle 8 has penetrated the tissue interface and distal seal 38.

Figure 10:
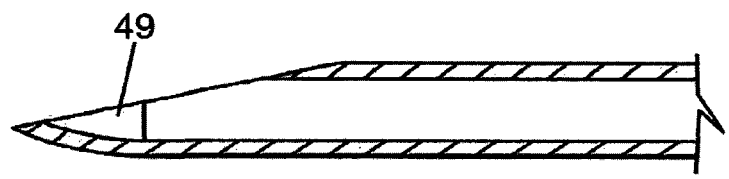
FIG. 10 depicts one embodiment of a cannulation device needle with a curved distal tip to direct the cannula at an angle from the long axis of the needle.
Figure 11:
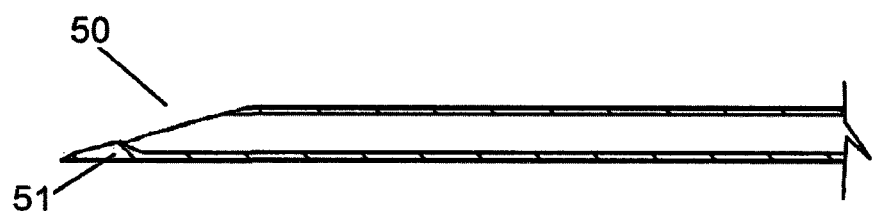
FIG. 11 depicts one embodiment of a cannulation device needle with an inner deflecting element in the needle lumen at the distal tip to direct the cannula at an angle from the long axis of the needle.
Figure 12:
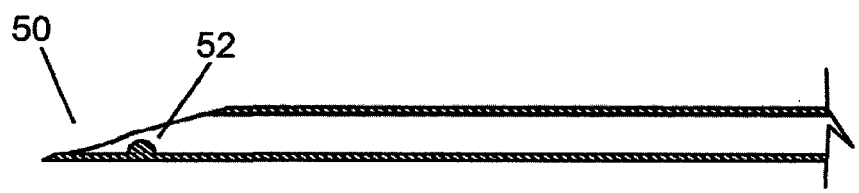
FIG. 12 depicts one embodiment of a cannulation device needle with a localized inner deflecting element in the needle lumen at the distal tip to direct the cannula at an angle from the long axis of the needle.

In some embodiments, the distal tip of the needle is configured to direct the tubular element at an angle from the long axis of the needle. Referring to the needle tip depicted in FIG. 10, the distal tip of the needle 49 may be curved to direct the tubular element. Referring to the needle tip depicted in FIG. 11, the distal tip of the needle 50 may have an inner deflecting element 51 in the lumen of the needle in the region of the bevel of the needle. Referring to the needle tip depicted in FIG. 12, the distal tip of the needle 50 may have a localized inner deflecting element 52 in the lumen of the needle in the region of the bevel of the needle.

The described embodiments of the cannulation device may be used in combination to cannulate a tissue space and administer a fluid, semi-solid or solid. In one embodiment the configuration of the distal portion of the cannulation device comprises the distal element which functions as a tissue interface and distal seal on the distal end of the needle. The cannula and reservoir for the delivery material may be configured for administration of a fluid, semi-solid, solid or implant from the cannula. In some embodiments, the lumen of the cannula may also act as the reservoir or a portion of the reservoir of the material for administration.

For use in the cannulation device, a lubricant or lubricious coating may be used to aid cannulation. For use in the device and deployment into the eye, the coating should provide immediate lubricity upon tissue contact. Some lubricious agents, such as polyvinylpyrrolidone coatings typically used on vascular catheters, require one to five minutes of moisture contact to provide lubricity and are not suitable for use with the cannulation device. Suitable lubricious agents for the cannula include, but are not limited to, oils, waxes, lipids, fatty acids, polymers and polymer solvent mixtures. Polymers include, but are not limited to, water soluble polymers such as polyethylene glycol and polypropylene glycol, and polymer lubricants such as polysiloxane. Polymer solvent mixtures include, but are not limited to, aqueous formulations of water soluble polymers such as polyethylene oxide, polyethylene glycol, glycosaminoglycan. Polymer solvent mixtures also include organic solvent formulations of silicone fluid or polyethylene glycol. Polymer solvent mixtures may be formulated with both a high molecular weight form of the polymer to provide durability with a lower molecular weight form of the polymer to provide increased lubricity. The lubricious agent may be applied to the entire cannula or the distal portion. The lubricious agent may be applied by spraying or dipping of the cannula. The lubricious agent may be unbound to the cannula surface, covalently bonded to the cannula surface or both unbound and covalently bounded to the cannula surface. Suitable covalent binding agents include silanes, isocyanates, polyisocyanates, epoxides, photoinitiators and photoreactive groups coupled to the lubricious agent. The lubricious agent may also be mechanically coupled to the surface of the cannula by the contact with the lubricious agent in polymeric form in a solvent for the cannula material to form an interpenetrating polymer composition on the cannula surface. The distal end of the needle lumen may also act as a small reservoir for the lubricant to coat the cannula during deployment.

The invention will now be described in reference to a number of examples, which are provided for illustrative purposes and are not to be construed as limiting on the scope of the invention.

EXAMPLES

Example 1. Fabrication of a Cannulation Device for Placement of an Illuminated Flexible Cannula in a Tissue Space of an Eye A device according to an embodiment of the invention was fabricated. The device consisted of a main body with a 27 gauge distal needle and an illuminated flexible cannula designed to slidably deploy through the needle. The main body comprised a housing and a drive mechanism to semi-automatically advance the cannula. The cannula was connected to a syringe for fluid delivery. The illumination for the cannula was provided by a 532 nm green laser.

The cannula was fabricated from polyurethane tubing of Shore 55D durometer, with an inner diameter of 0.13 mm, an outer diameter of 0.25 mm and a length of 30 mm. A reinforcement tube of polyimide, 0.25 mm inner diameter, 0.28 mm outer diameter and 20 mm long was placed over the proximal end of the polyurethane tube, leaving 10 mm of polyurethane as the distal flexible cannula segment.

The main body housing was fabricated from a 0.5 cc insulin syringe. The syringe plunger was discarded and the syringe needle was removed from the distal end of the barrel. The proximal lumen of the barrel was tapped with an 8-32 thread to accommodate a proximal stop screw. A 27 gauge extra thin walled hypodermic needle, with an inner diameter of 0.3 mm and an outer diameter of 0.41 mm and length of 20 mm was bonded into the syringe barrel. The needle was placed such that 2.5 mm of needle extended distally from the barrel tip and 14 mm extended proximally inside the bore of the syringe barrel. An "L" shaped slot was machined into the side of the barrel to accommodate a tube element for fluid delivery and to serve as a trigger for the cannula deployment.

The drive mechanism was fabricated from a shaft assembly and a compression spring serving as the force element to deploy the cannula. The shaft assembly was comprised of a proximal tube, a central connector and a distal mounting subassembly. The proximal tube was fabricated from 17 gauge thin walled hypodermic tubing, 1.19 mm inner diameter, 1.45 mm outer diameter and 87 mm long. The central connector was fabricated from acetal polymer tubing 1.57 mm inner diameter, 3.18 mm outer diameter and 16 mm long. A side hole 0.36 mm diameter was drilled into the central connector 7.3 mm from the distal end. The distal mounting assembly was fabricated from two segments of polyetheretherketone (PEEK) tubing with outer diameters of 1.58 mm. The proximal segment had an inner diameter of 0.35 mm, sized to mount the cannula. The distal segment had an inner diameter of 0.65 mm sized to mount a support tube. The support tube was fabricated from 23 gauge thin wall hypodermic tubing, 0.43 mm inner diameter, 0.64 mm outer diameter and 16.6 mm long. The support tube, bonded into the distal segment, provided support to prevent buckling of the cannula during deployment. The support tube was slidably disposed over the proximal end of the 27 gauge needle inside the syringe barrel thereby placing the distal end of the cannula within the proximal end of the lumen of the 27 gauge needle.

The proximal end of the cannula was bonded into the proximal PEEK segment of the mounting subassembly. The distal PEEK segment with the support tube bonded in place was slid over the cannula and the two PEEK segments were bonded together. The subassembly was pressed into the distal end of the central connector until the subassembly proximal end was just distal of the side hole in the connector. The proximal tube was inserted into the central connector until the distal end was just proximal of the side hole and then bonded in place. The gap between the mounting assembly and the proximal tube allowed for fluid flow into the central connector from the side hole and then into the lumen of the cannula. A segment of plastic optical fiber (POF) was inserted into the proximal tube and advanced until it was flush with the distal end of the tube. The assembly allowed the light from the POF to impinge on the end of the polyurethane cannula. The POF consisted of a polymethylmethacrylate core of 0.46 mm diameter, clad with a fluorinated polymer and then jacketed with polyethylene of 1 mm outer diameter. The POF was cut to 700 mm length. The proximal end of the POF was inserted into a machined connector fitting attached to the green laser. When the laser was activated, the light was transmitted through the POF to the proximal end of the cannula. The light was transmitted through the cannula with enough light exiting the walls of the cannula to illuminate the length of the cannula and sufficient light conduction to provide a brightly illuminated distal tip.

A compression spring provided the force element to deploy the cannula. The spring was fabricated from stainless steel wire 0.22 mm in diameter, and had an outer diameter of 2.6 mm and a length of 33 mm. The spring was placed over the proximal tube butting up against the central connector distally. A proximal stop was fabricated from an 8-23 thread nylon socket head screw, 16 mm long. A hole 1.5 mm in diameter was drilled through the axis of the screw to slidably fit over the proximal tube. The screw was threaded into the proximal end of the syringe barrel to provide the proximal stop for the compression spring. A silicone O-ring of Shore 50A durometer, with an inner diameter of 1.1 mm and an outer diameter of 3.6 mm was placed over the proximal tube, proximally to the stop. The O-ring served as a frictional element to slow the deployment speed of the cannula.

A fluid connection was made to the cannula through a side tube. The side tube consisted of a segment of 27 gauge stainless steel hypodermic tubing with an inner diameter of 0.20 mm, an outer diameter of 0.41 mm which was bent at 90 degrees. One end of the tube was inserted into the side hole of the central connector through the slot in the syringe barrel. A segment of polyurethane tubing with an inner diameter of 0.25 mm, an outer diameter of 0.51 mm and a length of 120 mm was attached to the open end of the hypodermic tube. A 30 gauge blunt Luer needle adapter was inserted into the proximal end of the polyurethane tube for the attachment of a syringe or other fluid delivery element. The drive mechanism with the attached cannula was retracted and rotated such that the side tube rested in the short leg of the "L" shaped slot. In this configuration, the device is in a locked state and the cannula is unable to be deployed. In use, the device was prepared for deployment by manually pushing the side tube over into the slot as the ready or activated state. By pushing the slide tube out of the slot, the cannula was observed to advance and deploy out of the tip of the needle by the drive mechanism.

Example 2. Cannulation Device for Placement of an Illuminated Flexible Cannula in the Suprachoroidal Space The device according to Example 1 was prepared. The drive mechanism was retracted and the side tube placed in the short leg of the barrel slot holding the device in the locked state. A 0.25 cc syringe was filled with 0.1% fluorescein solution and attached to the Luer connector at the end of the fluid connection tubing. The green laser was turned on, illuminating the cannula. A porcine cadaver eye was prepared. The 27 gauge needle of the device was inserted into the sclera at the pars plana at an acute angle toward the posterior of the eye and advanced until the bevel was substantially within the sclera. The side tube was pushed laterally into the slot, placing the device in the ready state. The cannula was prevented from advancing as the distal tip was within the scleral tissues. The needle was advanced further into the eye. When the needle tip entered the suprachoroidal space, the cannula deployed automatically under the force of the compression spring. The illuminated cannula could be visually observed under the sclera as a green line extending posteriorly from the needle entry location.

An injection of 0.1 cc of fluorescein was made through the cannula. The cannula was withdrawn from the eye. A scleral cut-down was made over the site of administration and upon entering the suprachoroidal space, a flush of fluorescein was observed, confirming placement of the injectate in the suprachoroidal space.

Example 3. Cannulation Device for Placement of an Illuminated Flexible Cannula in the Vitreous Cavity The device according to Example 1 was prepared as in Example 2. A porcine cadaver eye was prepared. The 27 gauge needle was inserted at the pars plana normal to the surface of the eye. The cannula was deployed as in Example 2. There was no observation of the illuminated cannula under the sclera, however it was observed through the cornea demonstrating placement within the vitreous cavity.

Example 4. Fabrication of a Cannulation Device with a Curved Flexible Cannula for Placement of the Cannula in a Tissue Space of an Eye A device similar to the one described in Example 1 was fabricated. The distal 2 mm of the cannula was formed at an angle of approximately 45 degrees. The cannula was placed over a forming wire and heated to 90 degrees centigrade for 30 seconds. The cannula was incorporated in the device with the curve oriented toward the bevel of the needle. The device and a porcine cadaver eye were prepared as in Example 2. The needle was inserted into the eye at an angle to the surface, with the bevel of the needle directed toward the exterior of the eye. The device was actuated and the needle advanced. The cannula was deployed and a scleral incision was made over the area distal from the needle. The cannula was observed in the suprachoroidal space.

Example 5

A device according to one embodiment of the invention was fabricated to inject a fluid material into the suprachoroidal space of the eye. A tubular main shaft was fabricated from a 12 gage thin wall stainless steel hypodermic tube 0.109 inch (2.77 mm) outer diameter and a 0.091 inch (2.31 mm) inner diameter and 5.5 inches (139.7 mm) long with an electro polished outer surface. A main shaft compression spring was fabricated from a 0.010 inch (0.25 mm) diameter stainless steel wire, with a 0.155 inch (2.31 mm) outer diameter and a free length of 3.63 inch (92.2 mm). The compression spring had a spring rate of 0.119 pounds (0.53 N) per inch (25.4 mm) at spring height of 2.040 inches (51.82 mm) and 0.146 pounds-force (0.65 N) at a spring height of 1.683 inches (42.75 mm). A coupler assembly was fabricated from polycarbonate with features to interact with the trigger lift point and holes to fit the centrally located fiber optic cable, the offset internal fluid line, and the tubular main shaft.

A fiber optic cable was fabricated from ESKA fiber SH-2001-J with a 0.020 inch (0.51 mm) fiber and a jacketed outside diameter of 0.040 inch (1.02 mm) and cut to 84 inches (213.4 cm) long with the insulation stripped for 1.5 inches (38.1 mm) at the distal end. An internal fluid line was fabricated from a 25 G thin wall hypodermic tube 5.03 (127.76 mm) inches long and grit blasted at each end for 0.25 inches (6.35 mm) length to increase adhesive bonding adhesion. The internal fluid line and the stripped end of the fiber optic cable were both adhesively bonded to the coupler assembly. The main shaft was slid over the proximal end of the fiber optic cable and the internal fluid line and adhesively bonded to the coupler assembly.

An external fluid line was fabricated from 80A durometer polyurethane with dimensions of 0.014 inches (0.36 mm) inner diameter, 0.019 inches (0.48 mm) thickness and 11.0 inches (279.4 mm) long. The external fluid line was adhesively bonded to the proximal end of the internal fluid line.

Proximal and distal bushings were fabricated from UHMWPE with 0.112 inch (2.84 mm) inner diameter and 0.25 inches (6.35 mm) outer diameter. The main shaft compression spring and bushings were slid over the fiber optic cable, external fluid line and the main shaft and up to the coupler assembly. An end cap was fabricated from polycarbonate and slid over the proximal end of the fiber optic cable and the internal fluid line for attachment to the proximal end of the housing body. A custom female Luer fitting fabricated with an internal dead volume of 5 microliters was adhesively bonded to the proximal end of the external fluid line. An optical connector for attachment to an external light source was fabricated with an inner diameter of 0.042 inches (1.07 mm) and adhesively bonded on the end of the fiber optic cable.

A flexible cannula assembly was fabricated from 55D durometer polyurethane tubing with a 0.005 inch (0.13 mm) inner diameter and 0.0098 inches (0.25 mm) outer diameter for the main body and 80A durometer polyurethane tubing with a 0.005 inch (0.13 mm) inner diameter and a 0.0098 inch (0.25 mm) outer diameter for the flexible cannula soft tip. A soft tip length of 0.070 inch (1.78 mm) was thermally fused to the main body and the distal end of the soft tip was buffed to round the edge on the distal end of the soft tip.

A flexible cannula proximal support was fabricated from a polyimide tube of 0.0102 inch (0.26 mm) inner diameter with a 0.0005 inch (0.013 mm) wall thickness and a length of 0.86 inch (21.84 mm). The cannula proximal support was slid over the cannula assembly and bonded in place. The flexible cannula proximal support was then adhesively bonded to the distal end of the coupler assembly.

A speed control compression spring, was fabricated from a 0.015 inch (0.38 mm) diameter stainless steel spring wire, with a free length of 0.175 inch (4.45 mm) long, an outer diameter of 0.106 inch (2.69 mm), and a spring rate of 28.75 pounds (127.9 N) per inch (25.4 mm). The spring had 3 active coils and 2 inactive coils with closed and ground ends. A Buna N, quad ring, size AS568-004 was used as a polymer speed control wheel. A 0.078 inch (1.98 mm) diameter by 0.187 inch (4.75) long stainless steel pin was used for the speed control wheel axle and a 0.063 inch (1.60 mm) diameter by 0.375 inch (9.53 mm) long stainless steel pin was used for the pivot arm axle.

The pivot arm was machined from polycarbonate. The speed control adjustment screw was fabricated from 304 stainless steel with a 4-40 thread with one end machined to a reduced diameter of 0.072 inch (1.83 mm). The speed control wheel axle was passed though the pivot arm and the speed control wheel and held in place by friction with the inside of the speed control wheel.

The housing assembly was machined from polycarbonate with a 4-40 threaded hole at the proximal end for the speed control adjustment screw and holes drilled for the pivot arm axle pin. The pivot arm axle pin was press fit into one side of the housing. The speed control adjustment screw was threaded into the hole in the housing. The pivot arm with the speed control wheel was mounted over the press fit pivot arm axle and the speed control compression spring was placed between the pivot arm and the speed control adjustment screw.

A trigger was machined from polycarbonate and the thickness of the flexible portion of the trigger was 0.028 inch (0.71 mm) thick. The trigger was placed between the two housing halves, the assembled main shaft was placed under the speed control polymer wheel, and the bushings were placed in cavities within the housing halves and the two halves of the housing assembly were adhesively bonded together.

A beveled needle was fabricated from 27 gauge 304 stainless steel extra thin wall hypodermic tubing. The tubing had an inner diameter of 0.0115 inch (0.292 mm) and an outer diameter of 0.0165 inch (0.42 mm) and a length of 0.80 inch (20.32 mm). The distal tip was ground with a lancet style bevel, with the primary bevel angle of 15 degrees. A nosecone was fabricated from polycarbonate and the beveled needle was adhesively bonded to the nosecone with 3 mm of needle extending from the distal surface of the nosecone and the bevel oriented horizontally as compared to the centerline of the housing. The nosecone was adhesively bonded to the distal end of the housing assembly with the distal end of the cannula placed into the proximal end of the needle such that the distal tip of the cannula was approximately 0.5 to 1 mm proximal to the proximal end of the needle bevel.

Example 6. Cannulation Device with a Distal Element and Deflecting Needle for Placement of a Flexible Cannula in the Suprachoroidal Space A device according to an embodiment of the invention was fabricated to deploy a flexible cannula into the suprachoroidal or supraciliary space of the eye. A barrel element was fabricated by cutting off the proximal end of a 0.5 ml insulin syringe to a barrel length of 30 mm. The integral needle was removed from the barrel to allow the attachment of standard Luer hub needles. The distal tip of the barrel was cut off leaving a remaining section of Luer taper capable of securely holding a Luer hub needle. A barrel end cap was fabricated from a nylon 10-32 socket head cap screw with a thread length of 4.5 mm. A through hole of 1.86 mm diameter was drilled through the end cap to allow the plunger to freely slide through the end cap. A plunger shaft was fabricated from a tubular Teflon coated stainless steel rod with an outer diameter of 1.8 mm and an inner diameter of 0.8 mm and a length of 43 mm. The distal end of the shaft was turned down to a diameter of 1.74 mm and a stainless steel washer of 4.1 mm outer diameter, 1.70 mm inner diameter and 0.5 mm thickness was press-fit onto the rod to provide a distal stop for the plunger spring. The proximal end of the rod was drilled out to 1.55 mm diameter. A compression spring with an outer diameter of 3.1 mm and a wire diameter of 0.18 mm and a length of 31.8 mm was placed over the shaft of the plunger and the barrel end cap was then slid over the plunger shaft proximal to the spring. The plunger assembly was placed into the barrel housing and the end cap was press fit into the barrel proximal end, securing the plunger assembly within the barrel.

A deflecting needle was fabricated from a 27 gauge×13 mm thin walled hypodermic needle. The distal tip of the needle was bent towards the bevel to create a ramp-like inner surface. The back side of the needle, opposite of the original bevel, was ground in a manner similar to a standard needle lancet tip with primary and secondary bevels to yield a sharp tip for tissue penetration. A 24 gauge thin walled tube 3 cm long was press fit into the needle hub butting up against the proximal end of the 27 gauge needle. The 24 gauge tube acted as a support tube to prevent the flexible cannula from kinking during deployment. The needle assembly was mounted onto the barrel assembly.

A flexible cannula was fabricated. The cannula shaft was comprised of a proximal segment of PEBAX polymer tubing of Shore 72D durometer 50 mm long with an inner diameter of 0.30 mm and an outer diameter of 0.38 mm. The proximal end of the proximal segment was attached to a 30 gauge blunt Luer tubing adapter. A distal segment of polyolefin polymer tubing 75 mm long with an inner diameter of 0.12 mm and an outer diameter of 0.20 mm was adhesively bonded to the distal end of the proximal segment. A nickel-titanium (Nitinol) stiffening wire 0.75 mm diameter was inserted into the flexible cannula to provide pushability for the thin walled distal cannula tube. The distal end of the cannula was formed into a rounded, atraumatic tip using cyanoacrylate adhesive. The flexible cannula was inserted through the plunger and needle assembly and then fixed in place at the proximal end of the plunger shaft. When fully deployed, the flexible cannula extended 15 mm beyond the tip of the needle.

A safety mechanism was incorporated into the device to prevent premature activation of the plunger by the plunger spring force. Two shallow grooves 180 degrees apart and perpendicular to the axis of the plunger were made in the plunger at a distance of 19 mm from the distal tip. The distance between the groove faces was 1.5 mm. A securement clip was fabricated from brass sheet with a width of 6.3 mm and a length of 18 mm. A slot with a width of 1.6 mm and a length of 8.8 mm was machined into the securement clip. The slot was cut in the center of the short side of the securement clip and traversing in the long axis direction.

A molded cylindrical tissue interface and distal seal element was fabricated from 70 Shore A durometer silicone rubber. The distal element had a length of 3.7 mm and a diameter of 1.75 mm. The distal element had a lumen of 2.7 mm length and 0.38 mm diameter. The distal end of the lumen of the distal element was configured with a beveled shape which conformed to the distal end of needle. The distal seal element was attached to the distal tip of the needle such that the needle bevel was in contact with the lumen bevel in order to seal the distal tip of the needle. The non-beveled section of the lumen acted as a Slidable seal on the shaft of the needle and provided enough frictional force against the needle shaft to maintain the distal tip against the eye surface during advancement of the needle through the distal seal of 1 mm thickness.

For use, the plunger was retracted thereby compressing the plunger spring and Withdrawing the flexible cannula until the plunger grooves were exposed proximally to the end cap. The securement clip was placed over the plunger such that the slot on the securement clip engaged the grooves on the plunger shaft. The securement clip then was held against the proximal end surface of the end cap by the spring force, preventing movement of the plunger.

A 1 cc syringe was filled with 0.5 ml of 0.01% fluorescein solution. The syringe was attached to the female Luer fitting on the proximal end of the cannula. A cadaver porcine eye was prepared by inflating the posterior chamber to a pressure of approximately 20 mm Hg. A target penetration location 4 mm posterior of the limbus of the eye was chosen for insertion of the device needle for deployment of the flexible cannula. The securement clip was removed from the plunger shaft. The tissue interface and distal seal was placed against the scleral surface and the needle tip was then advanced through the distal seal and into the tissues with the needle bevel oriented towards the posterior of the eye. Once the needle lumen reached the suprachoroidal space, the cannula was free to exit the needle and was deployed by the push rod under the plunger spring force. Once the plunger was seen to have been activated, 0.05 ml of fluorescein was injected through the flexible cannula and into the suprachoroidal space. A radial incision was made over the location of the flexible cannula, through the sclera to expose the suprachoroidal space. Once the space was entered, fluorescein solution was seen escaping from the space and further cut-down allowed for direct visualization of the flexible cannula shaft in the suprachoroidal space.

Example 7. Cannulation Device with a Distal Seal for Placement of a Flexible Cannula in the Suprachoroidal Space A device according to an embodiment of the invention was fabricated. The device comprised a cannula element, a needle with a distal seal, a cannula support element, a force element and a housing body.

The cannula element was fabricated to consist of a distal flexible tubular segment, a connection tube and a proximal Luer adapter to complete the flow path for the material to be administered. The distal flexible tubular element was fabricated from 72D durometer PEBAX tubing 75 mm long with an inner diameter of 0.12 mm and an outer diameter of 0.18 mm. The proximal end of the flexible cannula was pulled through a polyimide support tube 25 mm long with an inner diameter of 0.18 mm and an outer diameter of 1.59 mm, such that 20 mm of the flexible cannula extended proximally from the support tube. A support spring was fabricated from nickel titanium alloy (Nitinol) wire of 0.1 mm diameter. The support spring was 25 mm long with an inner diameter of 0.2 mm. The spring was wound with a pitch of 0.48 mm and had closed ends. The Nitinol spring was shape set by application of hot air at 480 degrees C. The support spring was placed over the polyimide support tube. The support tube and spring prevented the collapse or kinking of the flexible cannula inside the cannula support element. The proximal end of the flexible cannula was bonded inside a polyetheretherketone (PEEK) tube 10 mm long with an inner diameter of 0.17 mm and an outer diameter of 1.59 mm, with 10 mm of the flexible tube extending proximally from the PEEK tube. A connection tube comprised of polyethylene 250 mm long with an inner diameter of 0.28 mm and an outer diameter of 0.61 mm was placed over the exposed distal end of the flexible cannula and bonded to the PEEK tube.

The needle was fabricated from a 27 gauge thin walled needle 32 mm long. The needle was adhesively bonded into a polyethylene Luer hub with the beveled tip of the needle extending 3 mm from the distal end of the hub. The distal seal was fabricated from molded 50A durometer silicone elastomer with a length of 3 mm and an outer diameter of 0.75 mm. The proximal end was configured with a blind hole 2.1 mm long and 0.3 mm diameter and with a flat distal end. The distal seal was placed on the needle at the final step of the device assembly.

The cannula support element was fabricated from a distal tube, a connector tube and a proximal tube. The distal tube was fabricated from PEEK tubing 30 mm long with an inner diameter of 0.5 mm and an outer diameter of 1.59 mm. The proximal support element tube was fabricated from stainless steel tubing 110 mm long with an inner diameter of 1.32 mm and an outer diameter of 1.57 mm. A support element connector tube was fabricated from acetal (Delrin) tubing 25 mm long with an inner diameter of 1.59 and an outer diameter of 3.2 mm. The proximal end of the support element connector tube was bored to a diameter of 1.9 mm to accept the distal end of a force element spring support tube. The distal support element tube was placed over the flexible cannula and butted up to the cannula PEEK tube, covering the segment containing the support tube and support spring. The proximal support tube was placed over the cannula connection tube and adhesively bonded to the cannula PEEK tube. The support element connector tube was placed over the distal tube, cannula PEEK tube and proximal support tube junctions thereby holding the assembly together.

The force element was fabricated from a spring support tube, a compression spring and a proximal adjustable stop. The force element spring support tube was fabricated from stainless steel tubing 140 mm long with an inner diameter of 1.6 mm and an outer diameter of 2 mm. The compression spring was fabricated from stainless steel spring temper wire with a diameter of 0.26 mm. The compression spring was 100 mm long with an inner diameter of 2.6 mm and a pitch of 1.4 mm with closed ends. The adjustable stop was fabricated from a 10-32 nylon socket head cap screw 38 mm long with a hole of 2.2 mm diameter drilled through the axis. The spring support tube was placed over the polyethylene cannula connection tube and press fit into the proximal end of the Delrin cannula support element connector tube, thereby completing a subassembly consisting of the cannula element, cannula support element and spring support tube.

The housing body was constructed from a distal and proximal body fabricated from modified polycarbonate 1 mm syringe bodies. The distal body was modified by cutting off the finger flanges, then drilling and tapping the proximal end with a 5/16-18 thread, 8 mm deep. The syringe distal Luer lock connector was retained. The proximal body was modified by cutting off the finger flanges, then drilling and tapping the proximal end with a 10-32 thread, 19 mm deep. The distal end of the proximal body was machined down and threaded to a 5/16-18 thread that was 7.6 mm in length. In this manner, the distal and proximal bodies were attached via the 5/16-18 threaded portions for assembly of the device.

The device was assembled by placing the cannula element, cannula support element and force element spring support tube subassembly into the distal housing. The compression spring was placed over the spring support tube and the proximal housing was attached to the distal housing. The distal end of the flexible cannula was inserted into the lumen of the needle and the needle and needle Luer hub was attached to the distal housing Luer connector. The proximal end of the needle was slidably disposed within the distal PEEK tube of the cannula support element. The proximal end of the needle abutted the cannula support spring. The force element adjustable stop was placed over the cannula connector tube and threaded into the proximal end of the proximal housing. A 30 gauge Luer needle adapter was inserted into the proximal end of the cannula connector tube to allow connection of a syringe for delivery of the material to be administered.

With the mechanism in the deployed configuration, the flexible cannula was configured to extended 12 mm from the distal tip of the needle. The adjustable stop was screwed into the assembly so that the force element compression spring had just enough force to overcome the compression of the cannula support spring, allowing deployment of the cannula when the device was activated. The proximal end of the force element support rod protruded from the proximal end of the adjustable stop. A silicone O-ring with a tight fit on the force element support rod was temporarily placed over the support rod. The O-ring was used to hold the mechanism in the retracted configuration while the distal seal was placed over the needle tip. The O-ring was removed which set the device in a state ready for deployment.

A 0.25 ml syringe was filled with 100 microliters of 0.1% fluorescein solution and was attached to the proximal Luer fitting of the device. A cadaver porcine eye was prepared by inflating it to a pressure of 17 mm Hg. The distal seal of the device was placed against the sclera at the pars plana, approximately 6 mm posterior of the limbus. The device was angled approximately degrees from the surface of the globe with the needle bevel opening directed posteriorly. The device was advanced, allowing the needle tip to penetrate the distal seal and enter the scleral tissues. When the needle tip reached the suprachoroidal space, the flexible cannula advanced under the force of the force element compression spring. After deployment, the fluorescein solution was injected through the device. The device was withdrawn and set aside. A scleral cut-down was made from the area of needle penetration and extended posteriorly toward the target region for the distal end of the deployed cannula. The dissection revealed the fluorescein solution in the suprachoroidal space.

Example 8. Low Sealing Force Tissue Interface

Tissue interfaces were fabricated in a manner similar to those described in Example 5. Two different outer diameters of tissue interface were fabricated: 1.75 mm diameter and 2.50 mm diameter. Samples of each diameter tissue interface were fabricated using four different durometers of liquid silicone elastomer, Shore 10A, 30A, 50A and 70A.

An experimental set-up was prepared to determine the sealing force of the various samples of the tissue interface. A segment of PEEK tubing 8.3 mm long was placed over a 27 gauge×13 mm thin walled hypodermic needle to serve as a stop so as not to allow the tissue seals to travel proximally during the test. A tissue seal being tested was then placed over the needle tip. The length of the PEEK tubing was sized so as to allow approximately one-half of the needle bevel section to protrude through the tissue interface distal surface. A test surface was used which consisted of a silicone elastomer pad with a durometer of Shore 50A and 3.2 mm thick. The needle was mounted to a tee-fitting which in turn was mounted on the shaft of a digital force gauge with a 250N capacity mounted on a motorized test stand. The side leg of the tee-fitting was attached to a length of tubing and then to a Luer fitting and a three-way valve. A 10 cc syringe filled with water was attached to the valve. The syringe was held vertically using a ring stand. Tests were conducted using two different constant pressures which were generated by applying fixed weights of 1030 and 1656 grams respectively to the finger flange of the syringe plunger. The inside of the syringe had a cross-sectional area of $1.64 \times 10^{-4}$ m$^2$ which corresponded to fluid pressures of $6.18 \times 10^4$ Pa and $9.93 \times 10^4$ Pa respectively.

Figure 15:
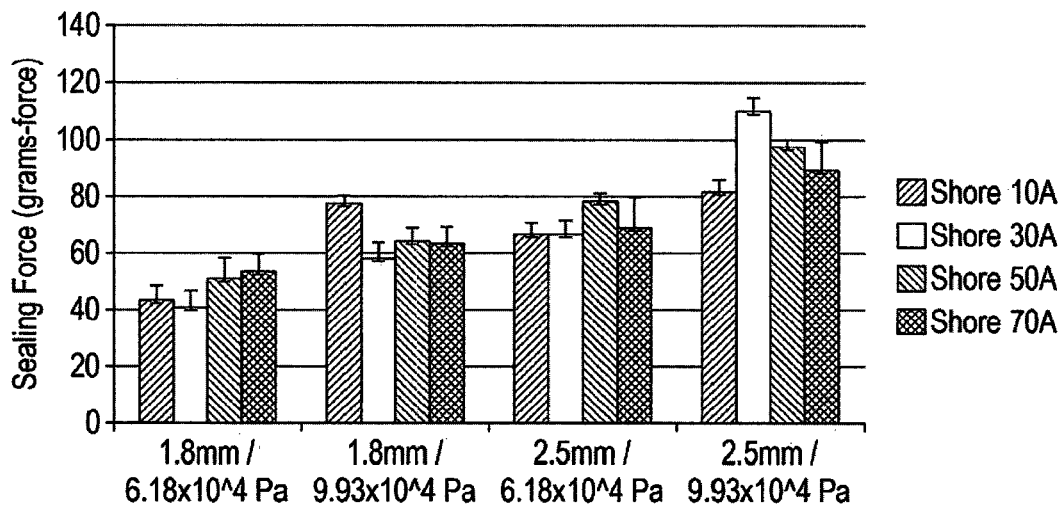
FIG. 15 is a graph of test results of the tissue interface minimum sealing force.

To perform a test, the needle tip was traversed down until the tissue interface was close to touching the silicone test pad. The test stand motor was jogged downward until approximately 30 grams-force of pressure was being applied to the tissue interface. The three-way valve was opened and the periphery of the tissue interface observed for water leakage. The valve was closed and then the needle was moved downward until approximately 35 grams-force of pressure was being applied. The valve was opened and the tissue interface observed for leakage. The tissue interface pressure on the test pad was increased in 5 gram-force increments in this manner until no leakage was observed, e.g. a seal was achieved and the force was recorded. The test was repeated with the second syringe pressure weight. The testing was performed on the two different tissue interface diameters and the four different durometers (Table 1 and FIG. 15). Two samples of each tissue interface were tested three times each for a total of six data points for each test condition. The silicone test pad was moved after each test so that each needle penetration was at a new site.

TABLE 1

Minimum Sealing Force in Gram-Force for Tissue Interface Test Samples (Average and Standard Deviation). Grouped by Tissue Interface Diameter and Fluid Pressure, as a Function of Durometer.

| Durometer | 1.8 mm Diameter $6.18 \times 10^4$ Pa | 1.8 mm Diameter $9.93 \times 10^4$ Pa | 2.5 mm Diameter $6.18 \times 10^4$ Pa | 2.5 mm Diameter $9.93 \times 10^4$ Pa |
|---|---|---|---|---|
| 10 | 43.3 ± 5.2 | 77.5 ± 2.7 | 66.7 ± 4.1 | 81.7 ± 4.1 |
| 30 | 40.8 ± 5.8 | 58.3 ± 5.2 | 66.7 ± 5.2 | 110.0 ± 4.5 |
| 50 | 50.8 ± 7.4 | 64.2 ± 4.9 | 78.3 ± 2.6 | 97.5 ± 2.7 |
| 70 | 53.3 ± 6.1 | 63.3 ± 6.1 | 69.2 ± 10.7 | 89.2 ± 10.2 |

Example 9. Semi-Solid Drug Composition

A semi-solid drug composition was prepared. A 1.5 wt % of polyethylene oxide (PolyOx WSR-303) of 7 million Daltons average molecular weight was dispersed in deionized water. Dexamethasone crystals with an average diameter of approximately 2 microns were mixed into the polyethylene oxide dispersion at a concentration of 8 wt %. The semi-solid composition was opaque due to the dispersed dexamethasone crystals.

A cannulation device according to Example 7 was fabricated to inject the semi-solid composition into the suprachoroidal space of an eye. The cannula was configured with a 10 mm deployed length.

An enucleated porcine eye was prepared by infusion to 17 mm Hg. The distal tip of the cannulation device was placed on the pars plana region of the eye and advanced into the eye with the bevel directed posteriorly. The self-actuated deployment of the cannula was observed to occur once the tip of the needle reached the appropriate depth to access the suprachoroidal space. Approximately one hundred microliters of the semi-solid drug composition were administered into the proximal end of the cannula through the female Luer lock connector. After administration, dissection of the sclera from the needle penetration site to the area 10 mm from the needle penetration site in the posterior direction of cannulation was performed. Dissection to the suprachoroidal space revealed the semi-solid composition in the posterior region of the suprachoroidal space. No perforation into the vitreous cavity was observed.

Example 10. Microspheres for Controlled Release of Corticosteroid

Microspheres containing an active agent were fabricated to provide controlled release of the agent after administration. Biodegradable polymers were used to fabricate the microspheres and encapsulate the active agent. The polymers included polylactic-glycolic copolymers (PLGA) with various lactic to glycolic (L to G) stoichiometry, various molecular weights as represented by intrinsic viscosity, with ester end groups. Table 2. lists the polymers used for microsphere fabrication.

TABLE 2

Microsphere Biodegradable Polymers

| Polymer | L to G Stoichiometry | Intrinsic Viscosity [dL/g] |
| --- | --- | --- |
| PLGA | 50:50 | 0.86 |
| PLGA | 65:35 | 0.92 |
| PLGA | 75:25 | 0.75 |
| PLGA | 85:15 | 0.78 |

The polymers were dispersed into an organic solvent mixture comprising a solvent for the polymer such as dichloromethane (DCM), chloroform, ethyl acetate, isopropyl acetate, mixed with a solvent to aid solubilization of the active agent, such as tetrahydrofuran (THF) or methanol (MeOH). In some fabrications more than one solvent was used to aid active agent solubilization. The polymer was dispersed at a solids concentration of approximately 3.2 to 4.3 weight % by mixing the polymer in the solvent system for approximately 4 to 24 hours until well dispersed. Dexamethasone acetate as the active agent was also added to the dispersion at a concentration of approximately 20 to 50 weight % of total solids (polymer plus drug).

The polymer and drug dispersion was emulsified in an aqueous dispersion of polyvinylalcohol at approximate concentrations of 2.5 to 6 weight %, where the dispersion formed the discontinuous phase of the emulsion. The emulsification was performed at 25 degrees centigrade. After tempering for approximately 8 to 30 hours to allow the microspheres to form and harden, the resultant suspension of microsphere was collected by filtration. The microspheres were suspended in water with 0.01 to 0.05 weight % Polysorbate 20 surfactant to rinse and prevent aggregation. The suspension was centrifuged at 2,500 rpm and the microspheres collected. Repeat rinsing was performed to remove residual polyvinyl alcohol. The collected microspheres were suspended in water, frozen and lyophilized to produce a dry, free flowing powder.

Microscopy of the microsphere powder samples showed a collection of spherical microspheres. Samples of microspheres were suspended in 0.1 weight % aqueous solution of Polysorbate 20 surfactant and analysis performed with a Coulter L5200 laser diffraction particle size analyzer. The resultant particle size distributions showed a volumetric mean particle size range of approximately 3.9 to 14.3 microns and a coefficient of variation of approximately 10.4% to 19.2%. Repeated microsphere fabrications demonstrated the ability to control the mean particle size from approximately 3 microns to 14 microns by varying the polymer, polymer solids concentration, solvent conditions and emulsification conditions.

Samples of the microspheres containing dexamethasone acetate were dissolved in acetonitrile to extract the active agent from the microspheres. The acetonitrile extract was filtered through a 0.2 micron filter and analyzed by reverse phase high performance liquid chromatography (RP-HPLC). The resultant peak for dexamethasone acetate was used to calculate the active agent concentration of the extract based on the response factor obtained by the analysis of dexamethasone acetate standard solutions. The active agent content of the microspheres was determined from the active agent concentration relative to the extracted amount of microspheres. Active agent contents of the microspheres were found to be controlled by adjusting the concentration of the active agent in the polymer dispersion. Microspheres were able to be produced with active agent content in the range of 16.1 to 42 weight %. The resultant microspheres with varying mean particle size and active agent content were used to provide a family of microsphere formulations. Table 3 lists the fabrication conditions of the active agent containing microspheres and the resultant volumetric mean particle size and active agent content.

TABLE 3

Drug Containing Microsphere Fabrications

| Polymer | Dispersion Solvents | Polymer Conc. [wt %] | Drug Conc. [wt %] | Mean Sphere Size [microns] | Agent Content [wt %] |
| --- | --- | --- | --- | --- | --- |
| PLGA 50:50 | DCM:THF (68:32) | 4.3% | 47.0% | 3.9 (10.8%) | 40.4% |
| PLGA 65:35 | DCM:THF (68:32) | 4.3% | 47.2% | 4.0 (12.1%) | 39.3% |

TABLE 3-continued

Drug Containing Microsphere Fabrications

| Polymer | Dispersion Solvents | Polymer Conc. [wt %] | Drug Conc. [wt %] | Mean Sphere Size [microns] | Agent Content [wt %] |
|---|---|---|---|---|---|
| PLGA 75:25 | DCM:THF (68:32) | 4.2% | 47.0% | 4.1 (12.1%) | 36.8% |
| PLGA 75:25 | DCM:THF (80:20) | 3.2% | 40.0% | 3.6 (11.9%) | 34.2% |
| PLGA 75:25 | DCM:THF (80:20) | 3.2% | 40.0% | 5.2 (16.8%) | 32.3% |
| PLGA 75:25 | DCM:THF (80:20) | 3.2% | 40.0% | 6.9 (16%) | 32.9% |
| PLGA 75:25 | DCM:THF (80:20) | 3.2% | 40.0% | 10.6 (11.8%) | 35.0% |
| PLGA 85:15 | DCM:THF (68:32) | 4.3% | 47.0% | 3.9 (17.5%) | 37.3% |
| PLGA 85:15 | DCM:THF (68:32) | 4.3% | 47.0% | 14.3 (11.6%) | 41.9% |
| PLGA 85:15 | DCM:THF (68:32) | 4.3% | 47.0% | 7.9 (10.4%) | 42.0% |
| PLGA 85:15 | DCM:THF (68:32) | 4.3% | 47.0% | 6.1 (18.2%) | 40.7% |
| PLGA 85:15 | DCM:THF (90:10) | 4.0% | 20.0% | 6.9 (18.8%) | 16.1% |
| PLGA 85:15 | DCM:THF (84:16) | 3.5% | 30.0% | 6.8 (19.2%) | 26.7% |

Polarization microscopy of the dry microsphere powders showed no significant amount of free crystals of active agent. Differential scanning calorimetry was performed on samples of the dry microsphere powders. A thermal profile with a rate of 10 to 15 degrees per minute was performed to characterize the microspheres. A thermal transition due to the polymer was observed in the range of 50 to 60 degrees C. An exothermic peak due to active agent recrystallization was observed in the range of 143 to 163 degrees C. An endothermic peak due to active agent melt was observed in the range of 203 to 221 degrees C. The active agent recrystallization enthalpy is calculated to be in the range of approximately 88.5% to 94.0% of the active agent melt enthalpy, indicating that the active agent is predominantly in the form of an amorphous solid dispersion in the polymer.

Figure 16:
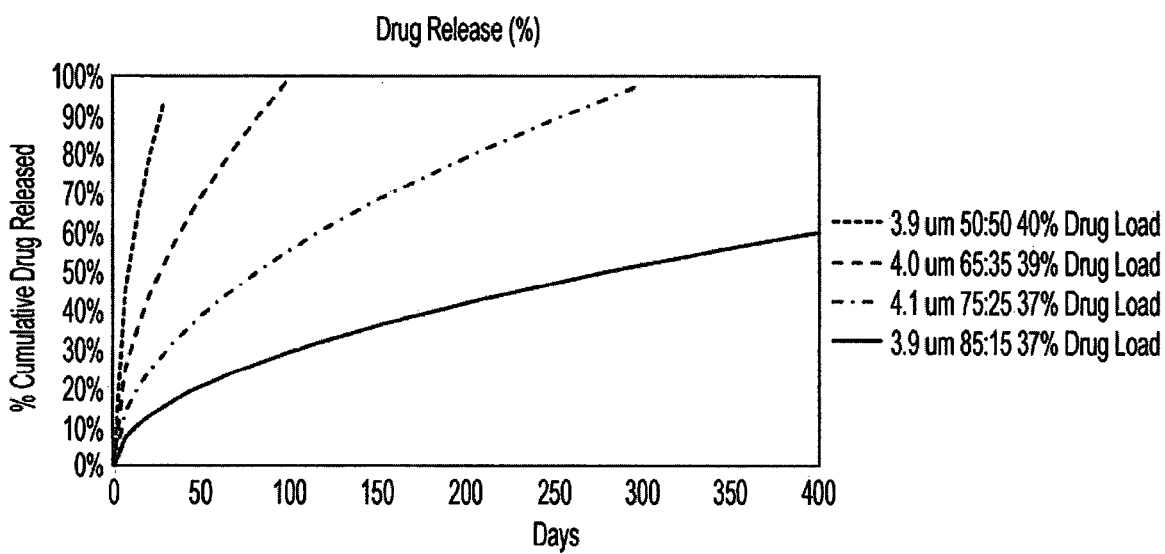
FIG. 16 is a graph of drug elution characteristics of PLGA polymer microspheres.
Figure 17:
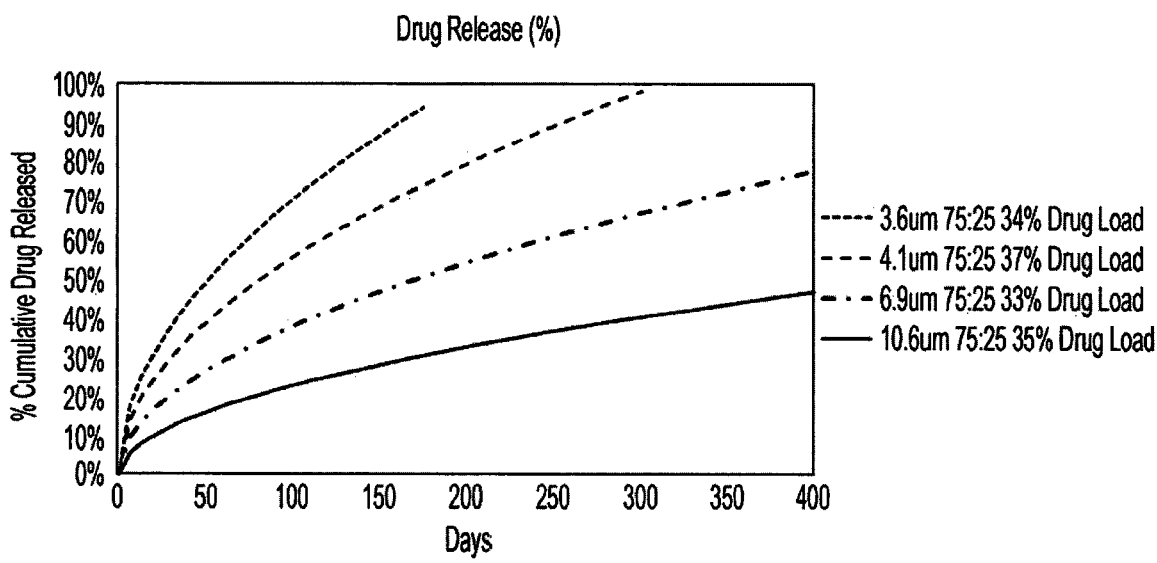
FIG. 17 is a graph of drug elution characteristics of 75:25 PLGA polymer microspheres.
Figure 18:
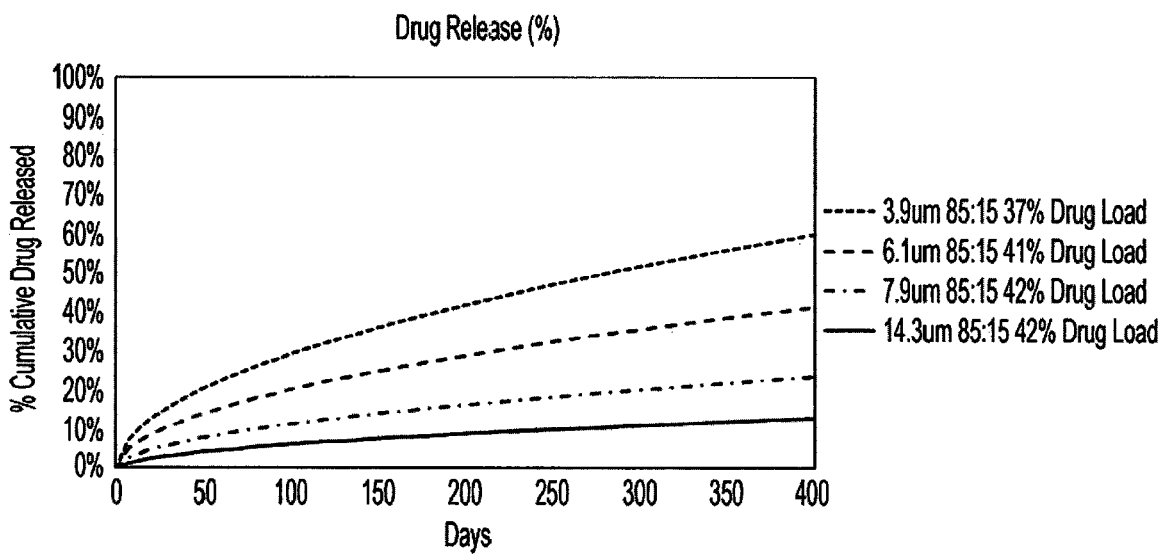
FIG. 18 is a graph of drug elution characteristics of 85:15 PLGA polymer microspheres.

A weighed sample of microspheres from the fabrications were placed in a vial with physiological buffer at an active agent concentration of 0.1 micrograms per ml. The vial was placed in an incubator at 37 degrees C. on a rotating platform at 200 rpm to promote mixing. Periodically a sample of the buffer was withdrawn and the active agent concentration is measured by RP-HPLC. The resultant data were used to determine the active agent (drug) elution profile for the microspheres to determine the rate of release for each microsphere formulation. The elution data was fit to the Korsmeyer-Peppas model equation for drug release. The elution testing was performed on various microsphere formulations with varying mean particle size, active agent loading and polymer. FIG. 16 depicts the elution profiles of PLGA microsphere with differing L to G stoichiometry from the modeled data. The microspheres demonstrate faster release with decreasing L to G stoichiometric ratio of the polymer in the microsphere formulations. FIG. 17 depicts the elution profiles of PLGA microspheres with 75:25 L to G stoichiometry and of different mean diameters from the data. The microspheres demonstrate faster release with decreasing mean diameter of the microspheres. FIG. 18 depicts the elution profiles of PLGA microsphere with 85:15 L to G stoichiometry of different mean diameters from the data. The microspheres demonstrate faster release with decreasing mean diameter of the microspheres. While the actual release in-vivo may differ from the laboratory characterization of drug elution, the modeled data demonstrates drug half-life ranging from 5 weeks to 80 weeks, demonstrating a broad range of release profiles that can be designed into the microspheres.

Example 11. Semi-Solid Drug Composition with Microspheres Containing Active Agent Various of semi-solid formulations for a material for injection containing the microspheres of Example 10 were prepared. The formulations were designed to allow lyophilisation to promote stability and rapid reconstitution with sterile water for administration. Mannitol at a concentration of 1 weight % to 10 weight %, Trehalose at a concentration of 1 weight % to 3 weight %, and sodium hyaluronate at a concentration of 0.3 to 1.0 weight % was solubilized in to 25 millimolar sodium phosphate buffer to act as an excipient mixture for the microspheres. In one formulation the mannitol concentration was 4 weight %, the Trehalose concentration was 1 weight % and the sodium hyaluronate concentration was 0.75 weight %, using two different molecular weights of sodium hyaluronate (HA). The sodium phosphate was prepared using sodium phosphate monobasic and sodium phosphate dibasic in deionized water in a ratio for a final pH of 7.4. The excipient mixtures were filter sterilized by passage through a sterile 0.2 micron filter. The excipient formulations were also characterized for viscosity on a Brookfield viscometer and demonstrated zero shear viscosity of 726 mPas for the formulations with 700K MW hyaluronic acid and 1,585 mPas for formulations with 1.5M MW hyaluronic acid.

The dexamethasone acetate PLGA encapsulated microspheres were sterilized by ionizing radiation and then combined with the excipient mixture in a range from 50 mg/ml to 150 mg/ml. Formulations with good suspension stability were prepared with concentrations of microspheres from 62 mg/mL to 125 mg/ml. A "tip-to-tip" syringe mixing technique was used to mix and create a suspension of the microspheres in the excipient mixture. The formulations were prepared for lyophilisation with a dilution ratio greater than the final reconstituted volume to produce a porous dry product to aid reconstitution with water. The final mixed formulations were filled into vials and frozen for at least 30 minutes at −70° C. The frozen vials were placed into a lyophilizer and lyophilized to dryness.

For administration, the lyophilized formulations were reconstituted by the addition of sterile water for injection to a microsphere concentration of 125 mg/ml. The reconstituted formulations were tested on a freezing point osmometer and demonstrated osmolality in the range of 300 to 850 mOsM. Table 4 lists the excipient formulations prepared and characterized. Table 5 lists the dry composition of the excipient formulations of Table 4 after lyophilisation. Table 6, Table 7 and Table 8 lists the dry composition of microsphere formulations of Table 4 after lyophilisation. All of the formulations demonstrated suitable suspension stability pre-lyophilisation to allow freezing and lyophilisation. All of the formulations demonstrated reconstitution to a uniform semi-solid for administration.

TABLE 4

Semi-Solid Excipient Formulations

| Na$_3$PO$_4$ [mM] | Mannitol [wt %] | Trehalose [wt %] | HA [wt %] | HA-MW [Dalton] | Pre-lyo [mg/g] | Post-lyo [mg/g] | Ratio | Tonicity [mOsm] |
|---|---|---|---|---|---|---|---|---|
| 5 | 1 | 1 | 0.75 | 0.7M | 50 | 125 | 2.5 | 450 |
| 5 | 1.2 | 1.2 | 0.3 | 1.0M | 50 | 125 | 2.5 | 524 |
| 5 | 1.5 | 1.5 | 0.375 | 1.0M | 50 | 125 | 2.5 | 500 |
| 5 | 1 | 1 | 0.375 | 1.0M | 50 | 125 | 2.5 | 500 |
| 10 | 3 | 3 | 0.75 | 1.5M | 50 | 125 | 2.5 | 524 |
| 10 | 3 | 3 | 0.75 | 1.5M | 50 | 125 | 2.5 | 635 |
| 25 | 10 | 2 | 0.75 | 1.5M | 62.5 | 125 | 2.0 | 721 |
| 25 | 10 | 2 | 0.75 | 1.5M | 62.5 | 125 | 2.0 | 721 |
| 10 | 2 | 1 | 1 | 1.5M | 40 | 125 | 3.1 | 250 |
| 10 | 3 | 3 | 0.75 | 1.5M | 62 | 125 | 2.0 | 650 |
| 25 | 4 | 1 | 0.75 | 1.5M | 62.5 | 125 | 2.0 | 354 |

TABLE 5

Semi-Solid Excipient Formulations After Lyophilisation

| Na$_3$PO$_4$ [mM] | Na$_3$PO$_4$ [wt %] | Mannitol [wt %] | Trehalose [wt %] | HA [wt %] |
|---|---|---|---|---|
| 5 | 4.10% | 34.87% | 34.87% | 26.15% |
| 5 | 4.18% | 42.59% | 42.59% | 10.65% |
| 5 | 3.35% | 42.96% | 42.96% | 10.74% |
| 5 | 4.74% | 40.11% | 40.11% | 15.04% |
| 10 | 3.24% | 43.01% | 43.01% | 10.75% |
| 10 | 3.24% | 43.01% | 43.01% | 10.75% |
| 25 | 3.98% | 75.31% | 15.06% | 5.65% |
| 25 | 3.98% | 75.31% | 15.06% | 5.65% |
| 10 | 5.49% | 47.25% | 23.63% | 23.63% |
| 10 | 3.24% | 43.01% | 43.01% | 10.75% |
| 25 | 9.03% | 63.29% | 15.82% | 11.87% |

TABLE 6

Semi-Solid Microsphere Excipient Formulations After Lyophilisation

| Na$_3$PO$_4$ [mM] | Na$_3$PO$_4$ [wt %] | Mannitol [wt %] | Trehalose [wt %] | HA [wt %] | Microspheres 70 mg/g [wt %] |
|---|---|---|---|---|---|
| 5 | 1.19% | 10.1% | 10.1% | 7.60% | 70.9% |
| 5 | 1.20% | 12.2% | 12.2% | 3.06% | 71.3% |
| 5 | 1.11% | 14.3% | 14.3% | 3.57% | 66.7% |
| 5 | 1.24% | 10.5% | 10.5% | 3.95% | 73.7% |
| 10 | 1.62% | 21.5% | 21.5% | 5.37% | 50.1% |
| 10 | 1.62% | 21.5% | 21.5% | 5.37% | 50.1% |
| 25 | 2.81% | 49.2% | 9.84% | 3.69% | 34.4% |
| 25 | 2.81% | 49.2% | 9.84% | 3.69% | 34.4% |
| 10 | 2.07% | 17.8% | 8.90% | 8.90% | 62.3% |
| 10 | 1.62% | 21.5% | 21.5% | 5.37% | 50.1% |
| 25 | 4.28% | 30.0% | 7.51% | 5.63% | 52.6% |

TABLE 7

Semi-Solid Microsphere Excipient Formulations After Lyophilisation

| Na$_3$PO$_4$ [mM] | Na$_3$PO$_4$ [wt %] | Mannitol [wt %] | Trehalose [wt %] | HA [wt %] | Microsphere 150 mg/g [wt %] |
|---|---|---|---|---|---|
| 5 | 0.66% | 5.6% | 5.6% | 4.20% | 84.0% |
| 5 | 0.66% | 6.7% | 6.7% | 1.68% | 84.2% |
| 5 | 0.63% | 8.1% | 8.1% | 2.03% | 81.1% |
| 5 | 0.68% | 5.7% | 5.7% | 2.14% | 85.7% |
| 10 | 1.03% | 13.7% | 13.7% | 3.41% | 68.3% |
| 10 | 1.03% | 13.7% | 13.7% | 3.41% | 68.3% |
| 25 | 2.01% | 35.3% | 7.1% | 2.65% | 53.0% |
| 10 | 1.21% | 10.4% | 5.2% | 5.20% | 78.0% |
| 10 | 1.03% | 13.7% | 13.7% | 3.41% | 68.3% |
| 25 | 2.68% | 18.8% | 4.7% | 3.52% | 70.4% |

TABLE 8

Semi-Solid Microsphere Excipient Formulations With Microspheres After Lyophilisation

| Na$_3$PO$_4$ [mM] | Na$_3$PO$_4$ [wt %] | Mannitol [wt %] | Trehalose [wt %] | HA [wt %] | Microsphere 200 mg/g [wt %] |
|---|---|---|---|---|---|
| 5 | 0.51% | 4.4% | 4.4% | 3.28% | 87.5% |
| 5 | 0.52% | 5.3% | 5.3% | 1.31% | 87.7% |
| 5 | 0.50% | 6.4% | 6.4% | 1.60% | 85.1% |
| 5 | 0.53% | 4.4% | 4.4% | 1.67% | 88.9% |
| 10 | 0.84% | 11.1% | 11.1% | 2.78% | 74.1% |
| 10 | 0.84% | 11.1% | 11.1% | 2.78% | 74.1% |
| 25 | 1.71% | 30.0% | 6.0% | 2.25% | 60.0% |
| 25 | 1.71% | 30.0% | 6.0% | 2.25% | 60.0% |
| 10 | 0.96% | 8.3% | 4.1% | 4.13% | 82.5% |
| 10 | 0.84% | 11.1% | 11.1% | 2.78% | 74.1% |
| 25 | 2.17% | 15.2% | 3.8% | 2.85% | 76.0% |

The reconstituted formulations were injected using the device of Example 1 demonstrating good injectability and visual homogeneity of the injected material. The injection formulation was also able to be injected through a 31 gauge needle with 0.5 inch length using a 1 ml syringe. All of the injection material formulations in Table 4 demonstrated good microsphere suspension stability, with the ability to be injected at least 30 minutes after reconstitution without additional mixing.

Example 12. Soft Tip Cannula for Cannulation of Small Tissue Spaces

In order to compare the deflection and penetration characteristics of various soft distal tip lengths, an experiment was conducted where different lengths of soft tips on a cannula of Example 5 were advanced towards a tissue model (7 weight % hi-bloom gelatin) at various angles. Soft distal tip lengths of 0.85 mm, 1.5 mm, 2.0 mm, 2.5 mm and 3 mm fabricated from 80A durometer polyurethane tubing were tested on the distal end of a 55D durometer polyurethane cannula. The distal ends of the soft tips were buffed to minimize a sharp leading edge. The cannulas were advanced towards the gel surface at a speed of 270 mm/min. The catheters were advanced though a 27 gauge extra thin wall needle with the distal edge of the needle bevel positioned touching the gelatin surface or buried within the gelatin to varying degrees. The bevelled opening of the needle was covered with a 50 shore A silicone elastomer sheet to simulate the sclera. The catheters were advanced 4.5 mm and the deflection from the gelatin surface or the penetration into the gel was observed visually. Testing was performed with the needle bevel at 90 degrees (perpendicular) to the surface of the gel, at a degree angle and at a 60 degree angle to the surface. The results of the testing showed that the 0.85 mm soft tip length did not have sufficient deflection and penetrated the gelatin in the least stringent condition of the needle touching the gelatin surface and at a 45 degree angle. The cannula with a soft tip of 1.5 mm length deflected from the surface with the needle touching the gelatin and angled at 45 degrees. The cannula with a soft tip of 2.0 mm length deflected from the surface with the needle touching the gel and at a 90 degree angle, and with the needle buried or deeply buried at a 45 degree needle angle. The cannula with a 2.5 mm soft tip deflected at all angles with the needle touching the gelatin surface and with the needle buried or deeply buried in the gelatin at 45 degrees. The cannula with a 3.0 mm soft tip deflected off the gelatin in all conditions and angles. The test results show deflection properties of the soft tip cannulas with a soft tip length greater than 0.85 mm and very good deflection properties with soft tip length of at least 1.5 mm.

Example 13. Cannulation of Live Porcine Eye with Cannulation Device

Devices as fabricated in Example 5 were tested in a porcine animal model. The animals were anesthetized and placed on their side. A sterile drape was placed over the eye and fenestrated. A speculum was placed to hold the lids open. A 5-0 Vicryl suture was placed at the limbus at the chosen clock hour injection site to provide traction. The procedures were performed without a microscope, under direct visual observation, with surgical loupes used by an observer. The devices for testing were attached to an external light source (iLumen Fiberoptic Illuminator, Ellex iScience). The light output of the cannulas of the devices were measured using a Thorlabs Optical Power meter (PM100D with S140C/S120-FC sensor), demonstrating a light output range of 165 to 700 mW.

Approaching at a 45 degree angle to the ocular surface, the needle tip was inserted into the eye at the pars plana region. With the illuminated cannula providing a "headlight" through the needle and illuminating the tissue surface directly ahead of the needle, the needle was advanced in the tissue until the headlight disappeared, providing visual indication that the needle bevel was in scleral tissue. The trigger button on the device was activated and then the device slowly and steadily advanced until the cannula deployed automatically. Observations of the trans-scleral illumination from the cannula shaft and tip were observed to determine the location of the cannula and the configuration of the cannula in-situ.

The devices were tested in 28 sites in the eyes resulting in 27 cases of the cannula observed through the overlying sclera and conjunctiva to be located in the suprachoroidal space as an illuminated line beginning near the needle insertion site at the supraciliary space or the anterior portion of the suprachoroidal space and extending posteriorly to a bright distal tip in the suprachoroidal space. The illumination from the cannula shaft clearly identified that the cannula was directed posteriorly from the insertion site of the needle. Tests were performed to deliberately place the cannula into the vitreous cavity resulting in no illumination visible through the sclera but light visible through the pupillary aperture, indicating that the device was not located in the suprachoroidal or supraciliary space but was instead located in the intraocular space.

A device was prepared with a 0.25 ml syringe filled with a semi-solid microsphere formulation of Example 10 (25 mM sodium phosphate, 4 wt mannitol, 1 wt trehalose, 0.75 wt % high molecular weight sodium hyaluronate). After insertion of the needle of the device into the sclera and deployment of the cannula into the suprachoroidal space observed by the trans-scleral illumination, 100 microliters of the formulation was injected into the suprachoroidal space. Due to the large volume of injection into the eye, a small amount of the injection material was observed at the needle injection site during removal of the cannula. Indirect ophthalmoscopy was performed with no observation of injection material in the vitreous, indicating successful suprachoroidal administration of the injection material.

Example 14. Pharmacokinetics of Semi-Solid Drug Composition with Controlled Drug Release Microspheres A microsphere formulation with 9.7 micron mean diameter and dexamethasone acetate drug load of 35 weight % was prepared from PLGA polymer of 75:25 L to G stoichiometry and intrinsic viscosity of 0.75 dL/g as described in Example 10. The microspheres were prepared to a concentration of 70 mg/ml in an injection material formulation of Example 11. A second microsphere formulation with 9.7 micron mean diameter and dexamethasone acetate drug load of 35 weight % was prepared from PLGA polymer of 85:15 L to G stoichiometry and intrinsic viscosity of 0.78 dL/g as described in Example 10. The microspheres were prepared to a concentration of 70 mg/ml in an injection material formulation of Example 11.

The two injection materials formulations were test articles administered to the suprachoroidal space of New Zealand White rabbits to determine their ocular pharmacokinetic characteristics. The animals were anesthetized, placed on their side and the head draped with an opening for the eye. An eyelid speculum was placed in the eyes. The test articles were swirled and withdrawn into a microliter calibrated syringe. A site on the eye between the rectus muscles was used for the introduction of the cannula portion of the cannula of Example 12 that was attached to a female Luer connector. A 5-0 Vicryl bridle suture was placed near the site to prevent excessive motion of the eye. A fiber optic was fabricated on a male Luer fitting to fit within the female Luer connector. When the Luer fittings were connected together, the distal end of the fiber optic abutted the proximal end of the cannula, providing a light path from the light source to the cannula. The proximal end of the fiber optic terminated in an optical connector which was attached to the light source of Example 12. The conjunctival and underlying sclera was dissected at the pars plana with a 2 to 3 mm radial incision to expose the suprachoroidal space and underlying choroid. The illuminated cannula was placed in the incision, directing the cannula posteriorly 4 to 5 mm. The location of the cannula in the suprachoroidal space was confirmed by the location of the trans-scleral illumination. The fiber optic was disconnected from the cannula and the syringe containing the material for injection connected to the cannula female Luer connector. The incision was sutured using a horizontal mattress suture around the cannula to stabilize the site. The injection material was administered through the cannula by depressing the syringe plunger to deliver 40 microliters of the injection material to the suprachoroidal space. The cannula was removed and the conjunctiva repositioned. An ophthalmoscopic examination of the eye was performed to confirm that the drug test article was not injected into the vitreous. The bridle suture and speculum were removed, the eye irrigated and antibiotic ointment applied per care guidelines. Six eyes were administered with each of the test articles.

Figure 19:
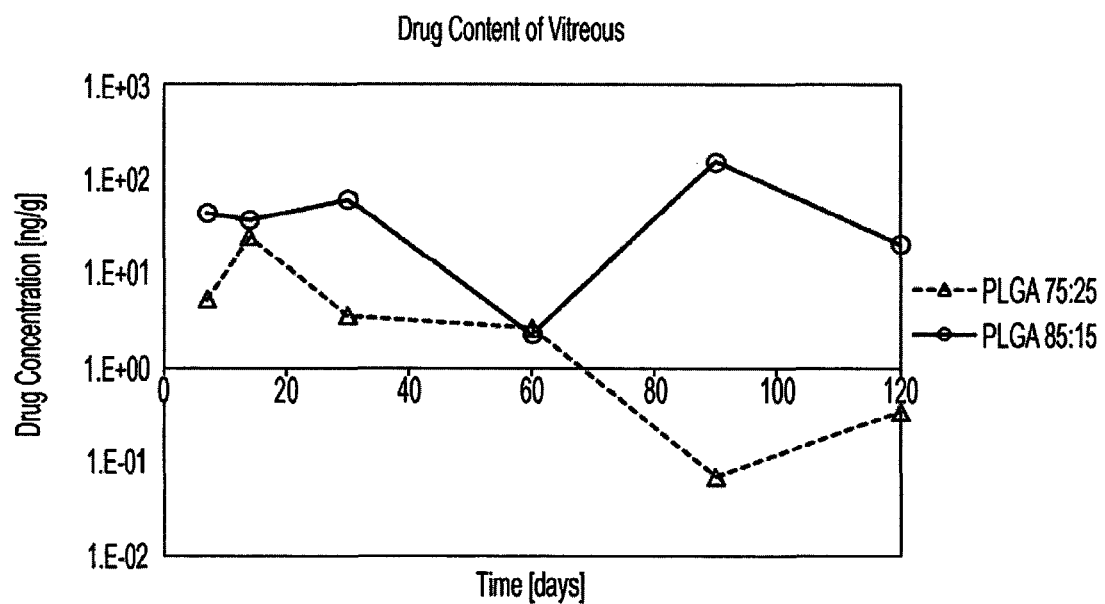
FIG. 19 is a graph of vitreous drug content.
Figure 20:
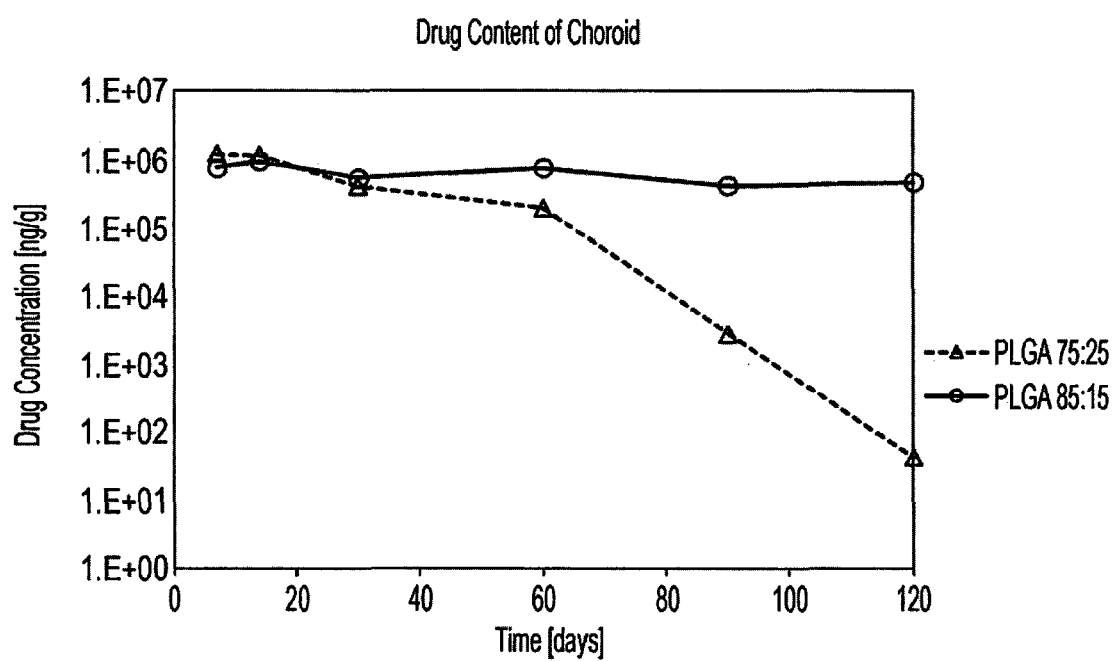
FIG. 20 is a graph of choroid drug content.
Figure 21:
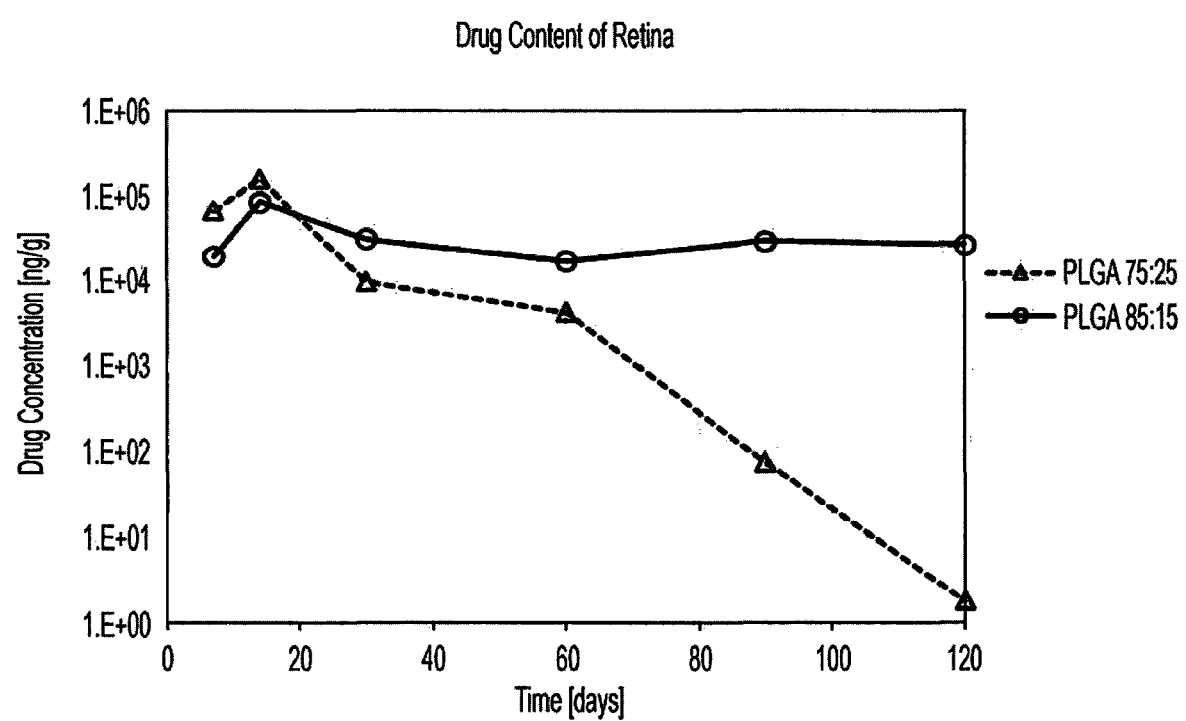
FIG. 21 is a graph of retina drug content.

The eyes were harvested at 7, 14, 30, 60, 90 and 120 days after administration of each test article. The eyes were dissected to separate the choroid, retina, and vitreous tissues. The tissues were assayed for drug concentration by LC-MS. The assay results showed dexamethasone acetate concentrations and the concentration of dexamethasone formed from hydrolysis of dexamethasone acetate in-vivo. The total of both forms of dexamethasone at the test time periods are depicted in the pharmacokinetic profile charts in FIG. 19, FIG. 20 and FIG. 21. FIG. 19 depicts the vitreous tissue drug concentration resulting from administration of both test articles. Both test articles demonstrated low total drug concentrations in the vitreous, resulting from the suprachoroidal administration and the slow sustained release properties of the test article formulations. FIG. 20 depicts the choroidal tissue drug concentration resulting from administration of both test articles. FIG. 21 depicts the retinal tissue drug concentration resulting from administration of both test articles. The 85:15 PLGA microsphere formulation demonstrated high sustained levels of total dexamethasone in both the retina and choroid over 120 days. The 75:25 PLGA microsphere formulation demonstrated high levels of total dexamethasone in both the retina and choroid over 60 days, with decreasing tissue drug concentration evident at 90 and 120 days.

The invention claimed is:

1. A sterile aqueous drug composition comprising:
   i) microspheres of biodegradable polymer and a drug, wherein the drug comprises 0.5 wt % to 70.0 wt % of the weight of the microspheres, wherein the microspheres have a mean diameter of 1 micron to 100 microns;
   ii) sodium hyaluronate at a concentration of 0.3 to 90.0 wt %; and
   iii) an excipient selected from the group consisting of mannitol, maltitol, sorbitol, maltose, lactose, glucose, fructose, galactose, sucrose, and dextran, or combinations thereof present in an amount from 5.0 wt % to 50.0 wt %;
   wherein the composition forms a suspension of microspheres in a concentration range of 70 to 200 mg per ml in an aqueous vehicle.

2. The drug composition of claim 1, additionally comprising a surfactant present in an amount from 0.1 wt % to 45.0 wt %.

3. The drug composition of claim 1, additionally comprising trehalose present in an amount from 0.1 wt % to 45.0 wt %.

4. The drug composition of claim 1, wherein the biodegradable polymer is selected from the group consisting of polyhydroxybutyrate, polydioxanone, polyorthoester, polycaprolactone, a polycaprolactone copolymer, a polycaprolactone-polyethylene glycol copolymer, polylactic acid, polyglycolic acid, polylactic-glycolic acid copolymer, and polylactic-glycolic acid-ethylene oxide copolymer.

5. The drug composition of claim 1, wherein the sodium hyaluronate has a molecular weight from 0.5 million daltons to 1.7 million daltons.

6. The drug composition of claim 1, further comprising a salt.

7. The drug composition of claim 4, wherein the composition is reconstituted to a semi-solid with an osmolality in range of 250 mOsM to 450 mOsM.

8. The drug composition of claim 5, wherein the salt is selected from the group consisting of sodium phosphate, potassium phosphate, sodium chloride, sodium carbonate, potassium carbonate, sodium acetate, and potassium acetate, or any combination thereof.

9. The drug composition of claim 6, wherein the drug is in the form of microspheres and the microspheres have a mean size of 2 to 50 microns to facilitate injection through a small gauge needle or small diameter cannula.

10. The drug composition of claim 1, wherein the small diameter needle or cannula is 27 gauge or smaller.

11. The drug composition of claim 1, wherein the biodegradable polymer comprises polylactic acid or polylactic-glycolic acid copolymer.

12. The drug composition of claim 1, wherein the microspheres comprise 10% to 45% by weight of the drug.

13. The drug composition of claim 1, wherein the drug is in the form of an amorphous solid dispersion.

14. The drug composition of claim 1, wherein the microspheres comprise a core of drug with an external surface barrier coating.

15. The drug composition of claim 14, wherein the barrier coating has a lower partition coefficient than the drug or greater water solubility than the drug.

16. The drug composition of claim 15, wherein the surface barrier coating comprises a non-toxic water soluble polymer, a biodegradable polymer, and/or a biological material.

17. The drug composition of claim 16, wherein the barrier coating comprises a non-toxic water soluble polymer selected from the group consisting of polyvinylpyrollidone, polyvinylpyrollidone co-vinyl acetate, polyvinyl alcohol, polyethylene glycol, and polyethylene oxide, or any combination thereof.

18. The drug composition of claim 16, wherein the surface barrier coating comprises a biodegradable polymer selected from the group consisting of polyhydroxybutyrate, polydioxanone, polyorthoester, polycaprolactone, polycaprolactone copolymer, polycaprolactone-polyethylene glycol copolymer, polylactic acid, polyglycolic acid, polylactic-glycolic acid copolymer, acid terminated polylactic-glycolic acid copolymer, and polylactic-glycolic acid-ethylene oxide copolymer, or any combination thereof.

19. The drug composition of claim 16, wherein the surface barrier coating comprises a biological material selected from the group consisting of gelatin, collagen, glycosaminoglycan, cellulose, chemically modified cellulose, dextran, alginate, chitin, chemically modified chitin, lipid, fatty acid, and sterol.

20. The drug composition of claim 14, wherein the barrier coating has a higher partition coefficient than the drug or less water solubility than the drug.

21. The drug composition of claim 20, where the barrier coating comprises a hydrophobic polymer, fatty acid, lipid, and/or sterol.

22. The drug composition of claim 21, where the lipid or fatty acid comprises capric acid, erucic acid, 1,2-dinervonoyl-sn-glycero-3-phosphocholine, 1,2-dimyristoyl-sn-glycero-3-phosphocholine, or 1,2-dipentadecanoyl-sn-glycero-3-phosphocholine, or any combination thereof.

23. The drug composition of claim 1, wherein the drug comprises a steroid, non-steroidal anti-inflammatory agent, an anti-histamine agent, an oncology agent, a VEGF inhibitor, a PDGF inhibitor, an anti-TNF alpha agent, an mTOR inhibitor, a cell therapy inhibitor, a nucleic acid based therapeutic, and/or a neuroprotectant agent.

24. The drug composition of claim 23, wherein:
the steroid comprises dexamethasone, dexamethasone acetate, fluocinolone, loteprednol, difluprednate, fluorometholone, prednisolone, medrysone, triamcinolone, betamethasone, rimexolone, beclomethasone dipropionate, budesenide, fluticasone dipropionate, mometasone furoate, or ciclesonide;
the non-steroidal anti-inflammatory agent comprises bromfenac, diclofenac, flurbiprofen, ketorolac tromethamine, or nepafenac;
the anti-histamine agent comprises cetirizine, loratadine, Fexofenadine HCl, olopatadine, alcaftadine, epinastine, or ketotifen;
the oncology agent comprises melphalan, topotecan, methotrexate, rituximab, carboplatin, or 5-FU;
the VEGF inhibitor comprises a tyrosine kinase inhibitor, an antibody to VEGF, an antibody fragment to VEGF, a VEGF binding fusion protein, or the PDGF inhibitor comprises an antibody to PDGF, an antibody fragment to PDGF, or a PDGF binding fusion protein;
the anti-TNF alpha agent comprises infliximab, etanercept, adalimumab, certolizumab, or golimumab;
the mTOR inhibitor comprises sirolimus, Everolimus, Temsirolimus, or an mTOR kinase inhibitor;
the cell therapy inhibitor comprises mesenchymal cells or cells transfected to produce a therapeutic agent;
the neuroprotectant agent comprises an antioxidant, calcineurin inhibitor, NOS inhibitor, sigma-1 modulator, AMPA antagonist, calcium channel blocker, DNA gyrase inhibitor, DNA polymerase inhibitor, RNA polymerase inhibitor, or histone-deacetylases inhibitor; or
the nucleic acid based therapeutic comprises a gene vector, gene editing therapeutic agent, plasmid, guide RNA, or siRNA.

25. A unit dosage form comprising the pharmaceutical formulation of claim 1.

26. A kit comprising the drug composition of claim 1 and a cannulation device.

* * * * *